(12) United States Patent
Neumann

(10) Patent No.: US 11,581,094 B2
(45) Date of Patent: Feb. 14, 2023

(54) METHODS AND SYSTEMS FOR GENERATING A DESCRIPTOR TRAIL USING ARTIFICIAL INTELLIGENCE

(71) Applicant: Kenneth Neumann, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 681 days.

(21) Appl. No.: 16/659,777

(22) Filed: Oct. 22, 2019

(65) Prior Publication Data

US 2021/0057100 A1    Feb. 25, 2021

Related U.S. Application Data

(63) Continuation-in-part of application No. 16/548,256, filed on Aug. 22, 2019.

(51) Int. Cl.
| | |
|---|---|
| *G16H 50/20* | (2018.01) |
| *G06N 20/00* | (2019.01) |
| *G06F 9/451* | (2018.01) |
| *G16B 5/00* | (2019.01) |
| *G16B 40/30* | (2019.01) |
| *G16B 20/00* | (2019.01) |
| *G16B 40/20* | (2019.01) |

(52) U.S. Cl.
CPC ............ *G16H 50/20* (2018.01); *G06F 9/451* (2018.02); *G06N 20/00* (2019.01); *G16B 5/00* (2019.02); *G16B 20/00* (2019.02); *G16B 40/20* (2019.02); *G16B 40/30* (2019.02)

(58) Field of Classification Search
None
See application file for complete search history.

(56) References Cited

U.S. PATENT DOCUMENTS

| | | | |
|---|---|---|---|
| 2014/0095204 A1* | 4/2014 | Fung ..................... | G16H 50/20 705/3 |
| 2019/0180870 A1* | 6/2019 | Kartoun ................. | G16H 20/00 |
| 2020/0005901 A1* | 1/2020 | Cohen .................... | G16B 20/00 |
| 2020/0350072 A1* | 11/2020 | McEwing .............. | G16H 50/70 |

* cited by examiner

*Primary Examiner* — Leon Viet Q Nguyen
(74) *Attorney, Agent, or Firm* — Caldwell Intellectual Property Law

(57) ABSTRACT

A system for updating a descriptor trail using artificial intelligence. The system is configured to display on a graphical user interface operating on a processor connected to a memory an element of diagnostic data. The system is configured to receive from a user client device an element of user constitutional data. The system is configured to display on a graphical user interface the element of user constitutional data. The system is configured to prompt an advisor input on a graphical user interface. The system is configured to receive from an advisor client device an advisor input containing an element of advisory data. The system is configured to generate an updated descriptor trail as a function of the advisor input. The system is configured to display the updated descriptor trail on a graphical user interface.

18 Claims, 20 Drawing Sheets

METHODS AND SYSTEMS FOR GENERATING A DESCRIPTOR TRAIL USING ARTIFICIAL INTELLIGENCE

RELATED APPLICATION DATA

This application is a continuation in part of U.S. Non-provisional patent application Ser. No. 16/548,256, filed on Aug. 22, 2019, and titled "METHODS AND SYSTEMS FOR GENERATING A DESCRIPTOR TRAIL USING ARTIFICIAL INTELLIGENCE," the entirety of which is incorporated herein by reference.

FIELD OF THE INVENTION

The present invention generally relates to the field of artificial intelligence. In particular, the present invention is directed to methods and systems for generating a descriptor trail using artificial intelligence.

BACKGROUND

Acquiring trust in computing proves to be challenging. Analyzing large quantities of data and ensuring accurate utilization of data can be difficult. Incorrect analysis and utilization can frustrate users and cause a lack of trustworthiness.

SUMMARY OF THE DISCLOSURE

In an aspect, a system for updating a descriptor trail using artificial intelligence the system comprising a processor connected to a memory, wherein the processor is designed and configured to display on a graphical user interface a descriptor trail wherein the descriptor trail includes an element of diagnostic data pertaining to a user including a prognostic output and a correlated ameliorative output and an element of machine-learning data. The system is configured to receive from a user client device an element of user constitutional data. The system is configured to display on the graphical user interface the element of user constitutional data. The system is configured to prompt an advisor input on the graphical user interface. The system is configured to receive from an advisor client device an advisor input containing an element of advisory data wherein the advisory data is generated as a function of the user constitutional data. The system is configured to generate an updated descriptor trail as a function of the advisor input. The system is configured to display the updated descriptor trail on the graphical user interface.

In an aspect, a method of updating a descriptor trail using artificial intelligence the method comprising displaying by a processor connected to a memory on a graphical user interface a descriptor trail wherein the descriptor trail includes an element of diagnostic data pertaining to a user including a prognostic output and a correlated ameliorative output and an element of machine-learning data. The method includes receiving by the processor from a user client device an element of user constitutional data. The method includes displaying by the processor on the graphical user interface the element of user constitutional data. The method includes prompting by the processor an advisor input on the graphical user interface. The method includes receiving by the processor from an advisor client device an advisor input containing an element of advisory data wherein the advisory data is generated as a function of the user constitutional data. The method includes generating by the processor an updated descriptor trail as a function of the advisor input. The method includes displaying by the processor the updated descriptor trail on the graphical user interface.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a descriptor trail using artificial intelligence. In an embodiment, at least a server receives at least a biological extraction. At least a server generates a prognostic output as a function of at least a biological extraction. At least a server generates an ameliorative output as a function of a prognostic output. At least a server records descriptor trail data such as a prognostic machine-learning process or an ameliorative machine-learning process in a descriptor trail data structure. At least a server generates at least a descriptor trail wherein the at least a descriptor trail includes at least an element of diagnostic data. At least a server filters a descriptor trail as a function of an advisory input.

Figure 1:
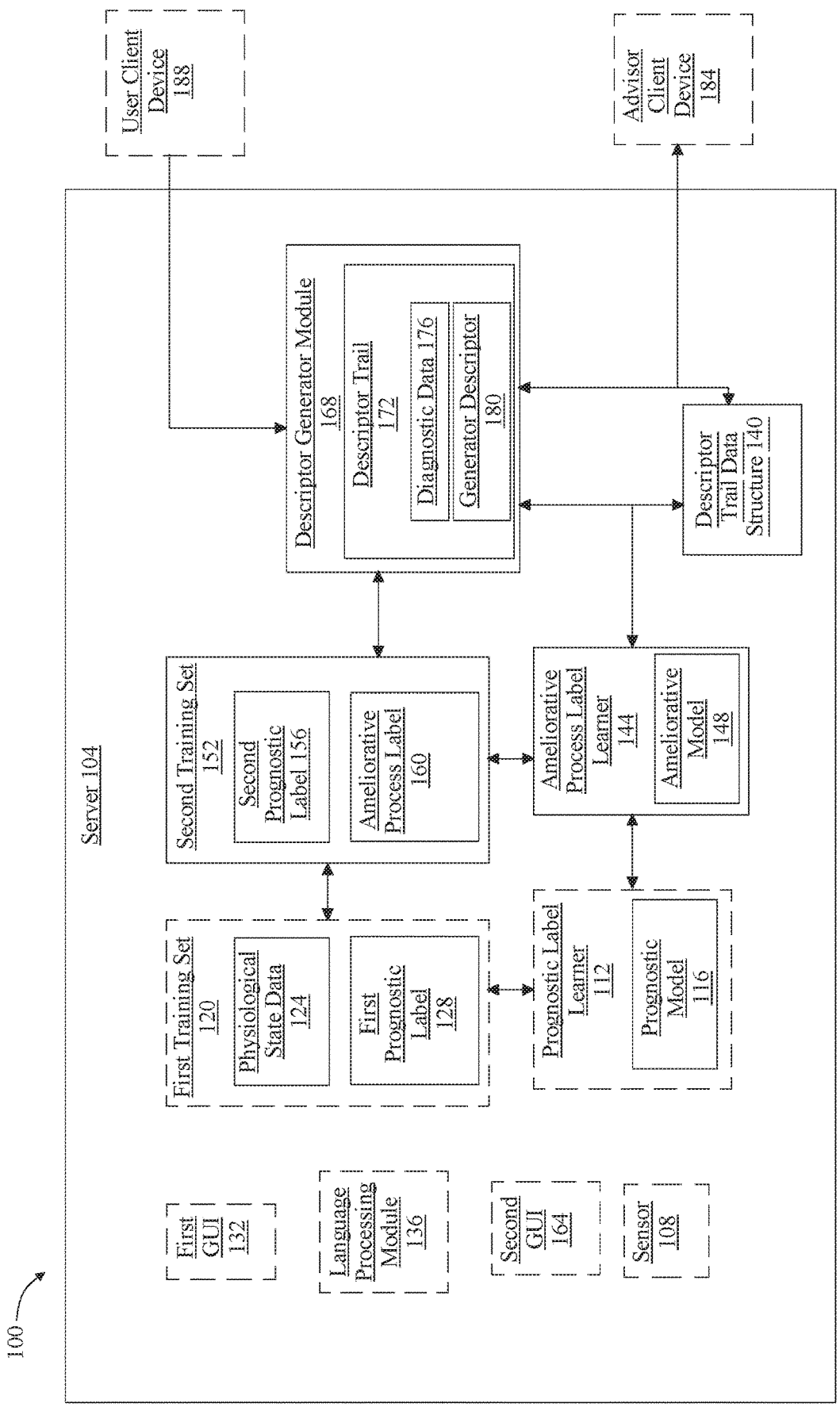
FIG. 1 is a block diagram illustrating an exemplary embodiment of a system for generating a descriptor trail using artificial intelligence.

Referring now to the drawings, FIG. 1 illustrates an exemplary embodiment of a system 100 for generating a descriptor trail using artificial intelligence. System 100 includes at least a server 104. At least a server 104 may include any computing device as described herein, including without limitation a microcontroller, microprocessor, digital signal processor (DSP) and/or system on a chip (SoC) as described below. At least a server 104 may be housed with, may be incorporated in, or may incorporate one or more sensor of at least a sensor. Computing device may include, be included in, and/or communicate with a mobile device such as a mobile telephone or smartphone. At least a server 104 may include a single computing device operating independently, or may include two or more computing device operating in concert, in parallel, sequentially or the like; two or more computing devices may be included together in a single computing device or in two or more computing devices. At least a server 104 may include one or more additional devices as described below in further detail via a network interface device. Network interface device may be utilized for connecting a at least a server 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. At least a server 104 may include but is not limited to, for example, at least a server 104 or cluster of computing devices in a first location and a second computing device or cluster of computing devices in a second location. At least a server 104 may include one or more computing devices dedicated to data storage, security, distribution of traffic for load balancing, and the like. At least a server 104 may distribute one or more computing tasks as described below across a plurality of computing devices, which may operate in parallel, in series, redundantly, or in any other manner used for distribution of tasks or memory between computing devices. At least a server 104 may be implemented using a "shared nothing" architecture in which data is cached at the worker, in an embodiment, this may enable scalability of system 100 and/or computing device.

With continued reference to FIG. 1, at least a server 104 and/or one or more modules operating thereon may be designed and/or configured to perform any method, method step, or sequence of method steps in any embodiment described in this disclosure, in any order and with any degree of repetition. For instance, at least a server 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a server 104 and/or one or more modules operating thereon may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, at least a server 104 is configured to receive at least a biological extraction. At least a biological extraction may include any element and/or elements of data suitable for use as at least an element of physiological state data 124 as described in more detail below. At least a biological extraction may include a physically extracted sample, which as used herein, includes a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, at least a biological extraction may include at least a genetic sample. At least a genetic sample may include a complete genome of a person or any portion thereof. At least a genetic sample may include a DNA sample and/or an RNA sample. At least a biological extraction may include an epigenetic sample, a proteomic sample, a tissue sample, a biopsy, and/or any other physically extracted sample. At least a biological extraction may include an endocrine sample. As a further non-limiting example, the at least a biological extraction may include a signal from at least a sensor 108 configured to detect physiological data of a user and recording the at least a biological extraction as a function of the signal. At least a sensor 108 may include any medical sensor 108 and/or medical device configured to capture sensor 108 data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. At least a sensor 108 may include any electromagnetic sensor 108, including without limitation electroencephalographic sensor 108, magnetoencephalographic sensor 108, electrocardiographic sensor 108, electromyographic sensor 108, or the like. At least a sensor 108 may include a temperature sensor 108. At least a sensor 108 may include any sensor 108 that may be included in a mobile device and/or wearable device, including without limitation a motion sensor 108 such as an inertial measurement unit (IMU), one or more accelerometers, one or more gyroscopes, one or more magnetometers, or the like. At least a wearable and/or mobile device sensor 108 may capture step, gait, and/or other mobility data, as well as data describing activity levels and/or physical fitness. At least a wearable and/or mobile device sensor 108 may detect heart rate or the like. At least a sensor 108 may detect any hematological parameter including blood oxygen level, pulse rate, heart rate, pulse rhythm, blood sugar, and/or blood pressure. At least a sensor 108 may be configured to detect internal and/or external biomarkers and/or readings. At least a sensor 108 may be a part of system 100 or may be a separate device in communication with system 100.

Still referring to FIG. 1, at least a biological extraction may include any data suitable for use as physiological state data 124 as described below, including without limitation any result of any medical test, physiological assessment, cognitive assessment, psychological assessment, or the like. System 100 may receive at least a biological extraction from one or more other devices after performance; system 100 may alternatively or additionally perform one or more assessments and/or tests to obtain at least a biological extraction, and/or one or more portions thereof, on system 100. For instance, at least biological extraction may include or more entries by a user in a form or similar graphical user interface object; one or more entries may include, without limitation, user responses to questions on a psychological, behavioral, personality, or cognitive test. For instance, at least a server 104 may present to user a set of assessment questions designed or intended to evaluate a current state of mind of the user, a current psychological state of the user, a personality trait of the user, or the like; at least a server 104 may provide user-entered responses to such questions directly as at least a biological extraction and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, at least a biological extraction may include assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor.

Still referring to FIG. 1, at least a biological extraction may include data describing one or more test results, including results of mobility tests, stress tests, dexterity tests, endocrinal tests, genetic tests, and/or electromyographic tests, biopsies, radiological tests, genetic tests, and/or sensor 108 tests. Persons skilled in the art, upon reviewing the entirety of this disclosure, will be aware of various additional examples of at least a physiological sample consistent with this disclosure.

With continued reference to FIG. 1, at least a server 104 may be configured to receive at least a biological extraction wherein the at least a biological extraction further comprises a fluid sample and classify the at least a biological extraction. Fluid sample may include any of the fluid samples as described above. Fluid sample may include for example, a blood sample, a urine sample, a semen sample, a sweat sample, a cerebrospinal fluid sample, a pleural fluid sample, a saliva sample, a synovial fluid sample, a pleural fluid sample, a pericardial fluid sample, a peritoneal fluid sample, and the like. Classifying the at least a biological extraction may include comparing the at least a biological extraction to at least a biological standard level and generating at least a biological extraction classifier label. A biological standard level, as used herein, includes any reference range for a given fluid sample that may include values utilized to interpret the results of a fluid sample. Reference range may include a set of values that approximately ninety five percent of the population may fall within. In an embodiment, biological standard level may include any reference range and/or control data for any biological extraction, including for example an image such as an x-ray, a user described behavior such as a response to a questionnaire about mental health of a user, and/or a genetic sample. Reference ranges may be reported by concentration such as by mass, by molarity, by units, by enzyme activity, by white blood cell count, by absence, by presence, and the like. Reference ranges may be created and/or endorsed in practice by particular medical groups and associations such as for example THE AMERICAN MEDICAL ASSOCIATION of Chicago, Ill., THE AMERICAN ASSOCIATION OF CLINICAL ENDOCRINOLOGISTS of Jacksonville, Fla., THE INSTITUTE FOR FUNCTIONAL MEDICINE of Federal Way, Wash., THE AMERICAN ACADEMY OF ANTI-AGING MEDICINE of Chicago, Ill. and the like. For example, a fluid sample such as a blood fluid sample analyzed for blood calcium levels may be associated with a reference range between 8.6 to 10.3 mg/dL (milligrams per deciliter). In yet another non-limiting example, a fluid sample such as a urine sample analyzed for glucose levels may be associated with a reference range between 0 to 0.8 mmol/L (millimoles per liter). In an embodiment, reference range may consist of control data that may indicate whether a particular biological extraction contains abnormal findings such as whether a particular x-ray contains a broken bone or whether a particular answer on a questionnaire indicates a possibility of depression.

With continued reference to FIG. 1 at least a biological extraction may be compared to at least a biological standard level and a biological extraction classifier label may be generated. A biological extraction classifier label, as used herein, is a datum generated by comparing at least a biological extraction to at least a biological standard level. Biological extraction classifier label may indicate how far or how close to any given reference range a particular biological extraction is by classifying a particular biological extraction as compared to a reference range. Classifications may include a biological extraction classifier label of "normal" when a biological extraction falls within a given reference range. Classifications may include a biological extraction classifier label of "elevated" when a biological extraction falls above a given reference range. Classifications may include a biological extraction classifier label of "low" when a biological extraction falls below a given reference range.

Classifications may include a biological extraction classifier label of "abnormal" when a biological extraction falls above and/or below a given reference range. For example, at least a biological extraction such as a blood sample containing a thyroid stimulating hormone (TSH) level of 12.5 milli-international units per liter may contain a biological extraction classifier label of "elevated" as compared to a reference range between 0.4 to 4.0 milli-international units per liter. In yet another non-limiting example, at least a biological extraction such as a urine sample containing a urea nitrogen level of 11.2 milligrams per deciliter (mg/dL) may contain a biological extraction classifier label of "normal" as compared to a reference range between 7 to 20 mg/dL. In an embodiment, at least a biological extraction may contain a plurality of biological extraction classifier labels. For instance and without limitation, at least a biological extraction such as a cerebrospinal fluid sample containing a protein level of 6.0 milligrams per 100 milters may contain biological extraction classifier labels of "low" and "abnormal" as compared to a reference range between 15 to 60 milligrams per 100 milliliters.

With continued reference to FIG. 1, generating at least a biological extraction classifier label may include matching at least a biological extraction with at least a category of physiological state data received from at least an expert. For instance and without limitation, contents of at least a biological extraction may be analyzed to determine particular fluid sample and analysis to match a given category of physiological data, and/or a given reference range of physiological data. For example, at least a biological extraction containing a blood sample containing a chem-7 basic metabolic panel may be matched to a given category of physiological data that relates to metabolic panels. In yet another non-limiting example, at least a biological extraction containing a urinalysis examining urine glucose levels may be matched to a given category of physiological data that relates to diagnosis of diabetes based on urine glucose levels. In such an instance, urine glucose levels may be matched to a given category of physiological data that may aid in evaluating urine glucose levels against reference ranges. Categories of physiological data received from at least an expert may include any of the categories of physiological data and expert input as described in more detail below.

With continued reference to FIG. 1, at least a server is configured to generate a prognostic output as a function of a biological extraction. Generating a prognostic output includes selecting a prognostic machine-learning process as a function of a biological extraction, recording the selected prognostic machine-learning process in a descriptor trail data structure and generating the prognostic output using the selected prognostic machine-learning process as a function of the biological extraction.

With continued reference to FIG. 1, generating a prognostic output may be performed by a prognostic label learner operating on at least a server 104. With continued reference to FIG. 1, at least a server 104 includes a prognostic label learner 112 operating on the at least a server, the prognostic label learner 112 designed and configured to generate at least a prognostic output wherein generating the at least a prognostic output further comprises creating at least a prognostic machine-learning model 116 relating physiological state data 124 to prognostic labels using at least a first training set 120 and generating the at least a prognostic output using the at least a biological extraction, the at least a first training set, and the at least a prognostic machine-learning model. Prognostic label learner 112 may include any hardware and/or software module. Prognostic label learner 112 is designed and configured to generate at least a prognostic output using machine-learning processes. A machine-learning process is a process that automatedly uses a body of data known as "training data" and/or a "training set" to generate an algorithm that will be performed by a computing device and/or module to produce outputs given data provided as inputs; this is in contrast to a non-machine-learning software program where the commands to be executed are determined in advance by a user and written in a programming language.

Still referring to FIG. 1, prognostic label learner 112 may be designed and configured to generate at least a prognostic output by creating at least a prognostic machine-learning model 116 relating physiological state data 124 to prognostic labels using a first training set and generating the at least a prognostic output using the prognostic machine-learning model 116; at least a prognostic machine-learning model 116 may include one or more models that determine a mathematical relationship between physiological state data 124 and prognostic labels. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

With continued reference to FIG. 1, at least a server 104 and/or prognostic label learner 112 may select a prognostic machine-learning algorithm as a function of the at least a biological extraction. For example, a biological extraction such as a hair sample may be best suited for a particular machine-learning algorithm such as a hierarchical clustering model while a biological extraction such as a blood sample may be best suited for a particular machine-learning model such as a supervised machine-learning model. In an embodiment, biological extractions may be matched to machine-learning algorithms. In an embodiment, a first training set selected as a function of at least a biological extraction may be best suited for a particular machine-learning algorithm. For instance and without limitation, a biological extraction such as a tissue sample analysis that is utilized to select a first training set that contains a plurality of three data entries may be best suited for a supervised machine-learning algorithm while a biological extraction such as a blood sample analysis that is utilized to select a first training set that contains a plurality of three hundred data entries may be best suited for an unsupervised machine-learning clustering algorithm whereby clusters generated from the unsupervised machine-learning algorithm may then be utilized in a supervised machine-learning algorithm. In an embodiment, at least a server 104 and/or prognostic label learner 112 may select a machine-learning model that relates particular inputs to outputs. For example, at least a server 104 and/or prognostic label learner 112 may select a machine-learning model as a function of the sample contained within at least a biological extraction whereby a blood sample may be utilized to select a particular machine-learning model and a urine sample may be utilized to select a separate machine-learning model.

With continued reference to FIG. 1, machine-learning algorithms may generate prognostic output as a function of a classification of at least a prognostic label. Classification as used herein includes pairing or grouping prognostic labels as a function of a shared commonality. Classification may include for example, groupings, pairings, and/or trends between physiological data and current prognostic label, future prognostic label, and the like. In an embodiment, machine-learning algorithms may examine relationships between a future propensity of a user to develop a condition based on current user physiological data. Machine-learning algorithms may include any and all algorithms as performed by any modules, described herein for prognostic label learner 112. For example, machine-learning algorithms may relate fasting blood glucose readings of a user to user's future propensity to develop diabetes. Machine-learning algorithms may examine precursor condition and future propensity to develop a subsequent disorder. For example, machine-learning algorithms may examine a user diagnosed with chicken pox and user's future propensity to subsequently develop shingles. In yet another non-limiting example, machine-learning algorithms may examine infection with human papillomavirus (HPV) and subsequent cancer diagnosis. Machine-learning algorithms may examine a user's propensity to have recurring attacks of a disease or condition, for example a user with elevated uric acid levels and repeated attacks of gout. Machine-learning algorithms may examine user's genetic predisposition to develop a certain condition or disease. For example, machine-learning algorithms may examine presence of hereditary non-polyposis colorectal cancer (HNPCC) commonly known as lynch syndrome, and subsequent diagnosis of colorectal cancer. In yet another non-limiting example, machine-learning algorithms may examine presence of abnormal squamous cells and/or abnormal glandular cells in the cervix and subsequent development of cervical cancer. Machine-learning algorithms may examine progression of disease state, for example progression of human immunodeficiency virus (HIV) is marked by decline of CD4+T-Cells, with a count below 200 leading to a diagnosis of acquired immunodeficiency syndrome (AIDS). In yet another non-limiting example, progression of diabetes may be marked by increases of hemoglobin A1C levels with a level of 6.5% indicating a diagnosis of diabetes. Machine-learning algorithms may examine progression of disease by certain age groups. For example, progression of Multiple Sclerosis in users between the age of 20-30 as compared to progression of Multiple Sclerosis in users between the age of 70-80. Machine-learning algorithms may be examining progression of aging such as measurements of telomere length and/or oxidative stress levels and chance mortality risk. Machine-learning algorithms may examine development of co-morbid conditions when a disease or conditions is already present. For example, machine-learning algorithms may examine a user diagnosed with depression and subsequent diagnosis of a co-morbid condition such as migraines, generalized anxiety disorder, antisocial personality disorder, agoraphobia, obsessive-compulsive disorder, drug dependence alcohol dependence, and/or panic disorder. Machine-learning algorithms may examine a user's lifetime chance of developing a certain disease or condition, such as a user's lifetime risk of heart disease, Alzheimer's disease, diabetes and the like. Machine-learning algorithms may be grouped and implemented according to any of the methodologies as described below.

Continuing to refer to FIG. 1, machine-learning algorithm used to generate prognostic machine-learning model 116 may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, prognostic label learner 112 may generate prognostic output using alternatively or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using a first training set; the trained network may then be used to apply detected relationships between elements of physiological state data 124 and prognostic labels.

With continued reference to FIG. 1, prognostic label learner 112 may be configured to generate a plurality of prognostic outputs each containing a ranked prognostic probability score. Prognostic probability score may be generated as a function of at least a biological extraction, at least a first training set, and at least a prognostic machine-learning model. A prognostic probability score, as used herein, is a mathematical representation indicating a likelihood of a particular prognostic output associated with at least a biological extraction. Prognostic probability score may include predictive values indicating a likelihood of a given prognostic output. In an embodiment, prognostic label learner 112 may generate a plurality of prognostic outputs which may each be ranked such as for example based on a decreasing likelihood of having a particular prognostic output. For instance and without limitation, at least a biological extraction such as a blood sample showing an elevated fasting blood glucose level may be utilized by prognostic label learner 112 in combination with at least a first training set 120 and at least a prognostic machine-learning model to generate a plurality of prognostic outputs that include diabetes mellitus type 2, pancreatitis, and Cushing's syndrome, with each prognostic output including a prognostic probability score and ranked in deceasing order of likelihood. In an embodiment, prognostic probability score may be calculated based on prevalence and predictive values. Prevalence indicates the probability of having a particular prognosis, and may also be known as the prior probability of having a particular prognosis. Predictive value indicates the probability of a prognosis in an individual with a biological extraction outside of normal limits and which contains a biological extraction classifier label of "low," "elevated" and/or "abnormal." Negative predictive value indicates the probability of not having a prognosis, such as when at least a biological extraction contains a biological extraction classifier label of "normal." In an embodiment, prognostic probability score may be calculated using machine-learning methods which may include any of the machine-learning methods as described herein. For example, in an embodiment prognostic label learner 112 may generate a plurality of prognostic outputs each containing a ranked prognostic probability score generated as a function of at least a biological extraction, at least a first training set, and at least a prognostic machine-learning model. In an embodiment, generating prognostic output may include selecting a lazy-learning process as a function of at least a biological extraction, recording the lazy-learning process in the descriptor trail data structure, and generating the prognostic output using the lazy-learning process as a function of the at least a biological extraction.

With continued reference to FIG. 1, at least a server 104 and/or prognostic label learner 112 may be configured to select training data to generate prognostic output using a selected machine-learning process. Training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

With continued reference to FIG. 1, at least a server 104 and/or prognostic label learner 112 may be configured to select a first training set 120 including a plurality of first data entries, each first data entry of the first training set 120 including at least an element of physiological state data 124 and at least a correlated first prognostic label 128. At least an element of physiological state data 124 may include any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. Physiological state data 124 may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data 124 may include, without limitation, immune function data such as Interleukine-6 (IL-6), TNF-alpha, systemic inflammatory cytokines, and the like.

Continuing to refer to FIG. 1, physiological state data 124 may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data 124 may include measures of glucose metabolism such as fasting glucose levels and/or hemoglobin A1-C(HbA1c) levels. Physiological state data 124 may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data 124 may include measures of estimated glomerular filtration rate (eGFR). Physiological state data 124 may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data 124 may include antinuclear antibody levels. Physiological state data 124 may include aluminum levels. Physiological state data 124 may include arsenic levels. Physiological state data 124 may include levels of fibrinogen, plasma cystatin C, and/or brain natriuretic peptide.

Continuing to refer to FIG. 1, physiological state data 124 may include measures of lung function such as forced expiratory volume, one second (FEV-1) which measures how much air can be exhaled in one second following a deep inhalation, forced vital capacity (FVC), which measures the volume of air that may be contained in the lungs. Physiological state data 124 may include a measurement blood pressure, including without limitation systolic and diastolic blood pressure. Physiological state data 124 may include a measure of waist circumference. Physiological state data 124 may include body mass index (BMI). Physiological state data 124 may include one or more measures of bone mass and/or density such as dual-energy x-ray absorptiometry. Physiological state data 124 may include one or more measures of muscle mass. Physiological state data 124 may include one or more measures of physical capability such as without limitation measures of grip strength, evaluations of standing balance, evaluations of gait speed, pegboard tests, timed up and go tests, and/or chair rising tests.

Still viewing FIG. 1, physiological state data 124 may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data 124 may include one or more measures of psychological function or state, such as without limitation clinical interviews, assessments of intellectual functioning and/or intelligence quotient (IQ) tests, personality assessments, and/or behavioral assessments. Physiological state data 124 may include one or more psychological self-assessments, which may include any self-administered and/or automatedly computer-administered assessments, whether administered within system 100 and/or via a third-party service or platform.

Continuing to refer to FIG. 1, physiological state data 124 may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chatrooms or the like, any textual, image, video, and/or data produced by the subject, any textual image, video and/or other data depicting and/or describing the subject, or the like. Any psychological data and/or data used to generate psychological data may be analyzed using machine-learning and/or language processing modules as described in this disclosure.

With continued reference to FIG. 1, physiological state data 124 may include one or more evaluations of sensor 108, including measures of audition, vision, olfaction, gustation, vestibular function and pain. Physiological state data 124 may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data 124 may include proteomic data, which as used herein, is data describing all proteins produced and/or modified by an organism, colony of organisms, or system of organisms, and/or a subset thereof. Physiological state data 124 may include data concerning a microbiome of a person, which as used herein, includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data 124 of a person, and/or on prognostic labels and/or ameliorative processes as described in further detail below. Physiological state data 124 may include any physiological state data 124, as described above, describing any multicellular organism living in or on a person including any parasitic and/or symbiotic organisms living in or on the persons; non-limiting examples may include mites, nematodes, flatworms, or the like.

With continuing reference to FIG. 1, physiological state data 124 may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Examples of physiological state data 124 described in this disclosure are presented for illustrative purposes only and are not meant to be exhaustive. Persons skilled in the art, upon reviewing the entirety of this disclosure, will be aware of various additional examples of physiological state data 124 that may be used consistently with descriptions of systems and methods as provided in this disclosure.

Continuing to refer to FIG. 1, each element of first training set 120 includes at least a first prognostic label 128. A prognostic label, as described herein, is an element of data identifying and/or describing a current, incipient, or probable future medical condition affecting a person; medical condition may include a particular disease, one or more symptoms associated with a syndrome, a syndrome, and/or any other measure of current or future health and/or heathy aging. At least a prognostic label may be associated with a physical and/or somatic condition, a mental condition such as a mental illness, neurosis, or the like, or any other condition affecting human health that may be associated with one or more elements of physiological state data 124 as described in further detail below. Conditions associated with prognostic labels may include, without limitation one or more diseases, defined for purposes herein as conditions that negatively affect structure and/or function of part or all of an organism. Conditions associated with prognostic labels may include, without limitation, acute or chronic infections, including without limitation infections by bacteria, archaea, viruses, viroids, prions, single-celled eukaryotic organisms such as amoeba, paramecia, trypanosomes, plasmodia, leishmania, and/or fungi, and/or multicellular parasites such as nematodes, arthropods, fungi, or the like. Prognostic labels may be associated with one or more immune disorders, including without limitation immunodeficiencies and/or auto-immune conditions. Prognostic labels may be associated with one or more metabolic disorders. Prognostic labels may be associated with one or more endocrine disorders. Prognostic labels may be associated with one or more cardiovascular disorders. Prognostic labels may be associated with one or more respiratory disorders. Prognostic labels may be associated with one or more disorders affecting connective tissue. Prognostic labels may be associated with one or more digestive disorders. Prognostic labels may be associated with one or more neurological disorders such as neuromuscular disorders, dementia, or the like. Prognostic labels may be associated with one or more disorders of the excretory system, including without limitation nephrological disorders. Prognostic labels may be associated with one or more liver disorders. Prognostic labels may be associated with one or more disorders of the bones such as osteoporosis. Prognostic labels may be associated with one or more disorders affecting joints, such as osteoarthritis, gout, and/or rheumatoid arthritis. Prognostic labels be associated with one or more cancers, including without limitation carcinomas, lymphomas, leukemias, germ cell tumor cancers, blastomas, and/or sarcomas. Prognostic labels may include descriptors of latent, dormant, and/or apparent disorders, diseases, and/or conditions. Prognostic labels may include descriptors of conditions for which a person may have a higher than average probability of development, such as a condition for which a person may have a "risk factor"; for instance, a person currently suffering from abdominal obesity may have a higher than average probability of developing type II diabetes. The above-described examples are presented for illustrative purposes only and are not intended to be exhaustive. Persons skilled in the art, upon reviewing the entirety of this disclosure, will be aware of various additional examples of conditions that may be associated with prognostic labels as described in this disclosure.

Still referring to FIG. 1, at least a prognostic label may be stored in any suitable data and/or data type. For instance, and without limitation, at least a prognostic label may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as at least a prognostic label may take; persons skilled in the art, upon reviewing the entirety of this disclosure, will be aware of various forms which may be suitable for use as at least a prognostic label consistently with this disclosure.

With continued reference to FIG. 1, at least a first training set 120 may be selected as a function of at least a biological extraction classifier label. For instance and without limitation, at least a biological extraction classifier label that is marked as "elevated" may be utilized to select at least a first training set 120 that includes a plurality of first data entries where at least a first data entry includes at least an element of physiological data that includes an element of "elevated" physiological data and at least a correlated first prognostic label. For example, at least a biological extraction such as a fasting blood glucose level that contains at least a biological extraction classifier label of "elevated" may be utilized to select at least a first training set 120 that includes at least an element of physiological data that includes at least an "elevated" fasting blood glucose level and at least a correlated first prognostic label. In yet another non-limiting example, at least a biological extraction such as a high density lipoprotein level (HDL) that contains at least a biological classifier label of "low" may be utilized to select at least a first training set 120 that includes at least an element of physiological data that includes at least a "low" high density lipoprotein level and at least a correlated first prognostic label.

With continued reference to FIG. 1, in each first data element of first training set 120, at least a first prognostic label of the data element is correlated with at least an element of physiological state data 124 of the data element. In an embodiment, an element of physiological data is correlated with a prognostic label where the element of physiological data is located in the same data element and/or portion of data element as the prognostic label; for example, and without limitation, an element of physiological data is correlated with a prognostic element where both element of physiological data and prognostic element are contained within the same first data element of the first training set 120. As a further example, an element of physiological data is correlated with a prognostic element where both share a category label as described in further detail below, where each is within a certain distance of the other within an ordered collection of data in data element, or the like. Still further, an element of physiological data may be correlated with a prognostic label where the element of physiological data and the prognostic label share an origin, such as being data that was collected with regard to a single person or the like. In an embodiment, a first datum may be more closely correlated with a second datum in the same data element than with a third datum contained in the same data element; for instance, the first element and the second element may be closer to each other in an ordered set of data than either is to the third element, the first element and second element may be contained in the same subdivision and/or section of data while the third element is in a different subdivision and/or section of data, or the like. Persons skilled in the art, upon reviewing the entirety of this disclosure, will be aware of various forms and/or degrees of correlation between physiological data and prognostic labels that may exist in first training set 120 and/or first data element consistently with this disclosure.

In an embodiment, and still referring to FIG. 1, at least a server 104 may be designed and configured to associate at least an element of physiological state data 124 with at least a category from a list of significant categories of physiological state data 124. Significant categories of physiological state data 124 may include labels and/or descriptors describing types of physiological state data 124 that are identified as being of high relevance in identifying prognostic labels. As a non-limiting example, one or more categories may identify significant categories of physiological state data 124 based on degree of diagnostic relevance to one or more impactful conditions and/or within one or more medical or public health fields. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. As an additional example, hemoglobin levels may be useful for identifying elevated testosterone, poor oxygen deliverability, thiamin deficiency, insulin resistance, anemia, liver disease, hypothyroidism, arginine deficiency, protein deficiency, inflammation, and/or nutrient deficiencies. In a further non-limiting example, hematocrit may be useful for identifying dehydration, elevated testosterone, poor oxygen deliverability, thiamin deficiency, insulin resistance, anemia, liver disease, hypothyroidism, arginine deficiency, protein deficiency, inflammation, and/or nutrient deficiencies. Similarly, measures of lipid levels in blood, such as total cholesterol, HDL, LDL, VLDL, triglycerides, LDL-C and/or HDL-C may be recognized as useful in identifying conditions such as poor thyroid function, insulin resistance, blood glucose dysregulation, magnesium deficiency, dehydration, kidney disease, familial hypercholesterolemia, liver dysfunction, oxidative stress, inflammation, malabsorption, anemia, alcohol abuse, diabetes, hypercholesterolemia, coronary artery disease, atherosclerosis, or the like. Persons skilled in the art, upon reviewing the entirety of this disclosure, will be aware of various additional categories of physiological data that may be used consistently with this disclosure.

Still referring to FIG. 1, at least a server 104 may receive the list of significant categories according to any suitable process; for instance, and without limitation, at least a server 104 may receive the list of significant categories from at least an expert. In an embodiment, at least a server 104 and/or a user device connected to at least a server 104 may provide a first graphical user interface 132, which may include without limitation a form or other graphical element having data entry fields, wherein one or more experts, including without limitation clinical and/or scientific experts, may enter information describing one or more categories of physiological data that the experts consider to be significant or useful for detection of conditions; fields in graphical user interface may provide options describing previously identified categories, which may include a comprehensive or near-comprehensive list of types of physiological data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. First graphical user interface 132 or the like may include fields corresponding to prognostic labels, where experts may enter data describing prognostic labels and/or categories of prognostic labels the experts consider related to entered categories of physiological data; for instance, such fields may include drop-down lists or other pre-populated data entry fields listing currently recorded prognostic labels, and which may be comprehensive, permitting each expert to select a prognostic label and/or a plurality of prognostic labels the expert believes to be predicted and/or associated with each category of physiological data selected by the expert. Fields for entry of prognostic labels and/or categories of prognostic labels may include free-form data entry fields such as text entry fields; as described above, examiners may enter data not presented in pre-populated data fields in the free-form data entry fields. Alternatively or additionally, fields for entry of prognostic labels may enable an expert to select and/or enter information describing or linked to a category of prognostic label that the expert considers significant, where significance may indicate likely impact on longevity, mortality, quality of life, or the like as described in further detail below. Graphical user interface may provide an expert with a field in which to indicate a reference to a document describing significant categories of physiological data, relationships of such categories to prognostic labels, and/or significant categories of prognostic labels. Any data described above may alternatively or additionally be received from experts similarly organized in paper form, which may be captured and entered into data in a similar way, or in a textual form such as a portable document file (PDF) with examiner entries, or the like With continued reference to FIG. 1, data information describing significant categories of physiological data, relationships of such categories to prognostic labels, and/or significant categories of prognostic labels may alternatively or additionally be extracted from one or more documents using a language processing module 136. Language processing module 136 may include any hardware and/or software module. Language processing module 136 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module 136 may compare extracted words to categories of physiological data recorded at least a server 104, one or more prognostic labels recorded at least a server 104, and/or one or more categories of prognostic labels recorded at least a server 104; such data for comparison may be entered on at least a server 104 as described above using expert data inputs or the like. In an embodiment, one or more categories may be enumerated, to find total count of mentions in such documents. Alternatively or additionally, language processing module 136 may operate to produce a language processing model. Language processing model may include a program automatically generated by at least a server 104 and/or language processing module 136 to produce associations between one or more words extracted from at least a document and detect associations, including without limitation mathematical associations, between such words, and/or associations of extracted words with categories of physiological data, relationships of such categories to prognostic labels, and/or categories of prognostic labels. Associations between language elements, where language elements include for purposes herein extracted words, categories of physiological data, relationships of such categories to prognostic labels, and/or categories of prognostic labels may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given category of physiological data, a given relationship of such categories to prognostic labels, and/or a given category of prognostic labels; positive or negative indication may include an indication that a given document is or is not indicating a category of physiological data, relationship of such category to prognostic labels, and/or category of prognostic labels is or is not significant. For instance, and without limitation, a negative indication may be determined from a phrase such as "telomere length was not found to be an accurate predictor of overall longevity," whereas a positive indication may be determined from a phrase such as "telomere length was found to be an accurate predictor of dementia," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at least a server 104, or the like.

Still referring to FIG. 1, language processing module 136 and/or at least a server 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein, are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module 136 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 136 may use a corpus of documents to generate associations between language elements in a language processing module 136, and at least a server 104 may then use such associations to analyze words extracted from one or more documents and determine that the one or more documents indicate significance of a category of physiological data, a given relationship of such categories to prognostic labels, and/or a given category of prognostic labels. In an embodiment, at least a server 104 may perform this analysis using a selected set of significant documents, such as documents identified by one or more experts as representing good science, good clinical analysis, or the like; experts may identify or enter such documents via graphical user interface as described above in reference to FIG. 9, or may communicate identities of significant documents according to any other suitable method of electronic communication, or by providing such identity to other persons who may enter such identifications into at least a server 104. Documents may be entered into at least a server 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, at least a server 104 may automatically obtain the document using such an identifier, for instance by submitting a request to a database or compendium of documents such as JSTOR as provided by Ithaka Harbors, Inc. of New York.

Continuing to refer to FIG. 1, whether an entry indicating significance of a category of physiological data, a given relationship of such categories to prognostic labels, and/or a given category of prognostic labels is entered via graphical user interface, alternative submission means, and/or extracted from a document or body of documents as described above, an entry or entries may be aggregated to indicate an overall degree of significance. For instance, each category of physiological data, relationship of such categories to prognostic labels, and/or category of prognostic labels may be given an overall significance score; overall significance score may, for instance, be incremented each time an expert submission and/or paper indicates significance as described above. Persons skilled in the art, upon reviewing the entirety of this disclosure will be aware of other ways in which scores may be generated using a plurality of entries, including averaging, weighted averaging, normalization, and the like. Significance scores may be ranked; that is, all categories of physiological data, relationships of such categories to prognostic labels, and/or categories of prognostic labels may be ranked according significance scores, for instance by ranking categories of physiological data, relationships of such categories to prognostic labels, and/or categories of prognostic labels higher according to higher significance scores and lower according to lower significance scores. Categories of physiological data, relationships of such categories to prognostic labels, and/or categories of prognostic labels may be eliminated from current use if they fail a threshold comparison, which may include a comparison of significance score to a threshold number, a requirement that significance score belong to a given portion of ranking such as a threshold percentile, quartile, or number of top-ranked scores. Significance scores may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated. Alternatively or additionally, significance scores may be calculated per sample type; for instance, entries by experts, documents, and/or descriptions of purposes of a given type of physiological test or sample collection as described above may indicate that for that type of physiological test or sample collection a first category of physiological data, relationship of such category to prognostic labels, and/or category of prognostic labels is significant with regard to that test, while a second category of physiological data, relationship of such category to prognostic labels, and/or category of prognostic labels is not significant; such indications may be used to perform a significance score for each category of physiological data, relationship of such category to prognostic labels, and/or category of prognostic labels is or is not significant per type of physiological sample, which then may be subjected to ranking, comparison to thresholds and/or elimination as described above.

Still referring to FIG. 1, at least a server 104 may detect further significant categories of physiological data, relationships of such categories to prognostic labels, and/or categories of prognostic labels using machine-learning processes, including without limitation unsupervised machine-learning processes as described in further detail below; such newly identified categories, as well as categories entered by experts in free-form fields as described above, may be added to pre-populated lists of categories, lists used to identify language elements for language learning module, and/or lists used to identify and/or score categories detected in documents, as described above.

Continuing to refer to FIG. 1, in an embodiment, at least a server 104 may be configured, for instance as part of receiving the first training set 120, to associate at least correlated first prognostic label 128 with at least a category from a list of significant categories of prognostic labels. Significant categories of prognostic labels may be acquired, determined, and/or ranked as described above. As a non-limiting example, prognostic labels may be organized according to relevance to and/or association with a list of significant conditions. A list of significant conditions may include, without limitation, conditions having generally acknowledged impact on longevity and/or quality of life; this may be determined, as a non-limiting example, by a product of relative frequency of a condition within the population with years of life and/or years of able-bodied existence lost, on average, as a result of the condition. A list of conditions may be modified for a given person to reflect a family history of the person; for instance, a person with a significant family history of a particular condition or set of conditions, or a genetic profile having a similarly significant association therewith, may have a higher probability of developing such conditions than a typical person from the general population, and as a result at least a server 104 may modify list of significant categories to reflect this difference.

With continued reference to FIG. 1, system 100 includes descriptor trail data structure 140. Descriptor trail data structure may be implemented, without limitation, as a relational database, a key-value retrieval datastore such as a NOSQL database, or any other format or structure for use as a datastore that a person skilled in the art would recognize as suitable upon review of the entirety of this disclosure. Descriptor trail data structure may contain data tables that may store diagnostic data as described in more detail below. Descriptor trail data structure may include any data structure capable of storing diagnostic detail including, for example and without limitation, linked lists, hash tables, vectors, and the like.

With continued reference to FIG. 1, at least a server 104 is configured to generate an ameliorative output as a function of a prognostic output. Generating an ameliorative output includes selecting at least an ameliorative machine-learning process as a function of a prognostic label, recording the selected ameliorative machine-learning process in the descriptor trail data structure, and generating the ameliorative output using the selected ameliorative machine-learning process as a function of the prognostic output.

With continued reference to FIG. 1, generating an ameliorative output may be performed by an ameliorative label learner operating on at least a server 104. Ameliorative process label learner 144 may include any hardware or software module suitable for use as a prognostic label learner 112 as described above. Ameliorative process label learner 144 is a machine-learning module as described above; ameliorative process label learner 144 may perform any machine-learning process or combination of processes suitable for use by a prognostic label learner 112 as described above. For instance, and without limitation, and ameliorative process label learner 144 may be configured to create a ameliorative machine-learning model 148 relating prognostic labels to ameliorative labels using the second training set 152 and generate the at least an ameliorative output using the ameliorative machine-learning model 148; ameliorative machine-learning model 148 may be generated according to any process, process steps, or combination of processes and/or process steps suitable for creation of prognostic machine-learning model. In an embodiment, ameliorative process label learner 144 may use data from first training set 120 as well as data from second training set 152; for instance, ameliorative process label learner 144 may use lazy learning and/or model generation to determine relationships between elements of physiological data, in combination with or instead of prognostic labels, and ameliorative labels. Where ameliorative process label learner 144 determines relationships between elements of physiological data and ameliorative labels directly, this may determine relationships between prognostic labels and ameliorative labels as well owing to the existence of relationships determined by prognostic label learner 112. In an embodiment, generating an ameliorative output may include selecting a lazy-learning process as a function of at least a biological extraction, recording the lazy-learning process in a descriptor trail data structure, and generating the prognostic output using the lazy-learning process as a function of the at least a biological extraction.

With continued reference to FIG. 1, ameliorative process label learner 144 may be configured to generate a plurality of ameliorative outputs each containing a prognostic improvement score correlated to at least a prognostic output. A prognostic improvement score, as used herein, includes a mathematical representation indicating a likelihood of a particular ameliorative output treating, preventing, and/or reversing a given prognostic output. Prognostic improvement score may be generated as a function of at least a prognostic output, at least a second training set, and at least an ameliorative machine-learning model. Ameliorative process label learner 144 may generate a plurality of ameliorative outputs each containing a prognostic improvement score. In an embodiment, plurality of ameliorative outputs may be ranked in descending order of improve ent. For example, a prognostic output such as diabetes may be utilized by ameliorative process label learner 144 in combination with second training set, and ameliorative machine-learning models to generate a plurality of ameliorative process labels that include intensive exercise therapy, an oral glucose controlling medication, and a blood sugar controlling supplement which may, each contain a prognostic improvement score indicating ability of each particular ameliorative output to treat, and/or reverse prognostic label of diabetes. In such an instance, plurality of ameliorative outputs generated by ameliorative process label learner 144 may be ranked in descending order of prognostic improvement score whereby intensive exercise may have the highest prognostic improvement score, oral glucose controlling medication may have the next highest prognostic improvement score, and blood sugar controlling supplement may have the lowest prognostic improvement score.

With continued reference to FIG. 1, selecting an ameliorative machine-learning process to generate ameliorative output may include selecting a second training set by at least a server 104 and/or ameliorative label learner. Second training set 152 including a plurality of second data entries. Each second data entry of the second training set 152 includes at least a second prognostic label; at least a second prognostic label 136 may include any label suitable for use as at least a first prognostic label 128 as described above. Each second data entry of the second training set 152 includes at least an ameliorative process label 160 correlated with the at least a second prognostic label, where correlation may include any correlation suitable for correlation of at least a first prognostic label 128 to at least an element of physiological data as described above. As used herein, an ameliorative process label 160 is an identifier, which may include any form of identifier suitable for use as a prognostic label as described above, identifying a process that tends to improve a physical condition of a user, where a physical condition of a user may include, without limitation, any physical condition identifiable using a prognostic label. Ameliorative processes may include, without limitation, exercise programs, including amount, intensity, and/or types of exercise recommended. Ameliorative processes may include, without limitation, dietary or nutritional recommendations based on data including nutritional content, digestibility, or the like. Ameliorative processes may include one or more medical procedures. Ameliorative processes may include one or more physical, psychological, or other therapies. Ameliorative processes may include one or more medications. Persons skilled in the art, upon reviewing the entirety of this disclosure, will be aware of various processes that may be used as ameliorative processes consistently with this disclosure.

With continued reference to FIG. 1, ameliorative process label learner 144 and/or at least a server 104 may be configured to select an ameliorative machine-learning algorithm as a function of the prognostic label. Selecting an ameliorative machine-learning algorithm may include selecting a machine-learning algorithm to generate ameliorative model. For instance and without limitation, a first training set utilized to generate a prognostic output may be correlated to a second training set that may be utilized to generate ameliorative output which may be utilized to select an ameliorative machine-learning process. In yet another non-limiting example, a plurality of prognostic labels generated by prognostic label learner 112 may be utilized to select a particular machine-learning algorithm that will utilize the plurality of prognostic labels to generate a particular ameliorative output. In yet another non-limiting example, a prognostic output that contains very few ameliorative outputs such as a rare form of cancer may be utilized to select an unsupervised machine-learning algorithm which may be best suited such as a k-nearest neighbors algorithm to find potential ameliorative treatment options. In yet another non-limiting example, a prognostic output that may be associated with numerous treatment options such as diabetes may be best suited for a supervised machine-learning algorithm. Ameliorative process label learner 144 and/or at least a server 104 may select at least a machine-learning model as a function of inputs and outputs utilized by ameliorative process label to generate ameliorative model 148. For example, a particular prognostic output utilized as an input by ameliorative process label learner 144 may be best suited for a particular machine-learning model. In yet another non-limiting example, a particular desired ameliorative output that will be generated by ameliorative process label learner 144 may be best suited for a different particular machine-learning model.

Continuing to refer to FIG. 1, in an embodiment at least a server 104 may be configured, for instance as part of selecting second training set 152, to associate the at least second prognostic label 156 with at least a category from a list of significant categories of prognostic labels. This may be performed as described above for use of lists of significant categories with regard to at least a first prognostic label. Significance may be determined, and/or association with at least a category, may be performed for prognostic labels in first training set 120 according to a first process as described above and for prognostic labels in second training set 152 according to a second process as described above.

Still referring to FIG. 1, at least a server 104 may be configured, for instance as part of selecting second training set 152, to associate at least a correlated ameliorative process label 160 with at least a category from a list of significant categories of ameliorative process labels 120. In an embodiment, at least a server 104 and/or a user device connected to at least a server 104 may provide a second graphical user interface 164 which may include without limitation a form or other graphical element having data entry fields, wherein one or more experts, including without limitation clinical and/or scientific experts, may enter information describing one or more categories of prognostic labels that the experts consider to be significant as described above; fields in graphical user interface may provide options describing previously identified categories, which may include a comprehensive or near-comprehensive list of types of prognostic labels, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to ameliorative labels, where experts may enter data describing ameliorative labels and/or categories of ameliorative labels the experts consider related to entered categories of prognostic labels; for instance, such fields may include drop-down lists or other pre-populated data entry fields listing currently recorded ameliorative labels, and which may be comprehensive, permitting each expert to select an ameliorative label and/or a plurality of ameliorative labels the expert believes to be predicted and/or associated with each category of prognostic labels selected by the expert. Fields for entry of ameliorative labels and/or categories of ameliorative labels may include free-form data entry fields such as text entry fields; as described above, examiners may enter data not presented in pre-populated data fields in the free-form data entry fields. Alternatively or additionally, fields for entry of ameliorative labels may enable an expert to select and/or enter information describing or linked to a category of ameliorative label that the expert considers significant, where significance may indicate likely impact on longevity, mortality, quality of life, or the like as described in further detail below. Graphical user interface may provide an expert with a field in which to indicate a reference to a document describing significant categories of prognostic labels, relationships of such categories to ameliorative labels, and/or significant categories of ameliorative labels. Such information may alternatively be entered according to any other suitable means for entry of expert data as described above. Data concerning significant categories of prognostic labels, relationships of such categories to ameliorative labels, and/or significant categories of ameliorative labels may be entered using analysis of documents using language processing module 136 or the like as described above.

In an embodiment, and still referring to FIG. 1, at least a server 104 may extract at least a second data entry from one or more documents; extraction may be performed using any language processing method as described above. At least a server 104 may be configured, for instance as part of receiving second training set 152, to receive at least a document describing at least a medical history and extract at least a second data entry of plurality of second data entries from the at least a document. A medical history document may include, for instance, a document received from an expert and/or medical practitioner describing treatment of a patient; document may be anonymized by removal of one or more patient-identifying features from document. A medical history document may include a case study, such as a case study published in a medical journal or written up by an expert. A medical history document may contain data describing and/or described by a prognostic label; for instance, the medical history document may list a diagnosis that a medical practitioner made concerning the patient, a finding that the patient is at risk for a given condition and/or evinces some precursor state for the condition, or the like. A medical history document may contain data describing and/or described by an ameliorative process label; for instance, the medical history document may list a therapy, recommendation, or other ameliorative process that a medical practitioner described or recommended to a patient. A medical history document may describe an outcome; for instance, medical history document may describe an improvement in a condition describing or described by a prognostic label, and/or may describe that the condition did not improve. Prognostic labels, ameliorative process labels 120, and/or efficacy of ameliorative process labels 120 may be extracted from and/or determined from one or more medical history documents using any processes for language processing as described above; for instance, language processing module 136 may perform such processes. As a non-limiting example, positive and/or negative indications regarding ameliorative processes identified in medical history documents may be determined in a manner described above for determination of positive and/or negative indications regarding categories of physiological data, relationships of such categories to prognostic labels, and/or categories of prognostic labels.

With continued reference to FIG. 1, at least a server 104 may be configured, for instance as part of receiving second training set 152, to receive at least a second data entry of the plurality of second data entries from at least an expert. This may be performed, without limitation using second graphical user interface 164 as described above.

With continued reference to FIG. 1, at least a server 104 is configured to select training data including at least a first training set 120 and at least a second training set 152. At least a server 104 may be configured to select at least a first training set 120 as a function of at least a biological extraction classifier label. At least a server 104 may be configured to select at least a first training set 120 as a function of at least a physically extracted sample contained within at least a biological extraction. For example, at least a biological extraction containing a stool sample may be utilized to select at least a first training set 120 that includes physiological state data 124 that includes a stool sample. In yet another non-limiting example, at least a biological extraction containing a urine sample may be utilized to select at least a first training set 120 that includes physiological state data 124 that includes a urine sample. Training data may be organized according to physiological categories and contained within a training set database as described in more detail below.

With continued reference to FIG. 1, at least a server 104 may be configured to generate a prognostic output and/or ameliorative output based on the at least a biological extraction, the prognostic output and/or ameliorative output including at least a prognostic output and at least an ameliorative output using the at least a first training set, the at least a second training set, and the at least a biological extraction.

With continued reference to FIG. 1, system 100 includes a descriptor generator module 168 operating on the at least a server wherein the descriptor generator module 168 is designed and configured to generate at least a descriptor trail 172 wherein the at least a descriptor trail 172 includes at least an element of diagnostic data 176. Descriptor generator module 168 may include any hardware and/or software module. A descriptor trail 172, as used herein, includes a datum containing at least an element of diagnostic data and at least a generator descriptor containing data describing processes utilized and selected to generate and/or calculate a prognostic output and/or ameliorative output. Descriptor trail 172 includes at least an element of diagnostic data 176. Diagnostic data 176, as used herein, includes any data and/or data element used to generate a prognostic output and/or ameliorative output. Diagnostic data 176 may include at least a biological extraction, biological extraction classifier label, training data, a first training set, a second training set, a prognostic output, an ameliorative output, a prognostic output and/or ameliorative output, any machine-learning model utilized to generate a prognostic output and/or ameliorative output, a plurality of prognostic outputs, a plurality of ameliorative outputs, any regression models, weighted variables, confidence levels, error functions, datasets, models, and/or calculations utilized to generate a prognostic output and/or ameliorative output. For example, diagnostic data 176 may include a plurality of prognostic outputs and further calculations utilized to select a particular prognostic output from the plurality of prognostic outputs to be included in the prognostic output and/or ameliorative output. In yet another non-limiting example, diagnostic data 176 may include a first training set 120 that is utilized to generate a prognostic output, or a biological extraction utilized to select at least a first training set. In an embodiment, diagnostic data 176 may include an element of diagnostic data 176 such as a segment of a second training set 152 which does not include the entire second training set. In an embodiment, diagnostic data 176 may include a plurality of training sets utilized to generate an ameliorative output or a confidence interval associated with a particular prognostic output. In an embodiment, diagnostic data 176 may include a supervised machine-learning algorithm utilized to generate a prognostic output. In an embodiment, diagnostic data 176 may include a lazy-learning process utilized to generate an ameliorative output. Descriptor trail 172 includes generator descriptor 180. Generator descriptor 180, as used herein, includes any datum describing generation and/or calculation of a prognostic output and/or ameliorative output, and/or any process therefor. For example, generator descriptor 180 may include a description of a particular supervised machine-learning model selected to generate a prognostic output including for example a description of particular training sets utilized to generate the supervised machine-learning model in addition to particular training sets that were not selected and not utilized to generate the supervised machine-learning model. In yet another non-limiting example, generator descriptor 180 may include a description of a particular hierarchical clustering model utilized to generate an ameliorative output that may include a description of certain data clusters generated and utilized in the hierarchical clustering model as well as a description of which data clusters were discarded and not utilized. Generator descriptor 180 does not contain diagnostic data 176.

With continued reference to FIG. 1, descriptor generator module 168 may be configured to receive at least an advisor filter input containing at least a diagnostic data 176 selection, generate at least a descriptor trail 172 as a function of the at least an advisor filter, and transmit the at least a descriptor trail 172 to at least an advisor client device. An advisor filter input, as used herein is an input datum received from at least an informed advisor containing a specification for a particular element and/or element of diagnostic data 176. Informed advisor is defined for the purposes of this disclosure as any person besides the user who has access to information useable to aid user in interaction with artificial intelligence advisory system. An informed advisor may include, without limitation, a medical professional such as a doctor, nurse, nurse practitioner, functional medicine practitioner, any professional with a career in medicine, nutrition, genetics, fitness, life sciences, insurance, and/or any other applicable industry that may contribute information and data to system 100 regarding medical needs. An informed advisor may include a spiritual or philosophical advisor, such as a religious leader, pastor, imam, rabbi, or the like. An informed advisor may include a physical fitness advisor, such as without limitation a personal trainer, instructor in yoga or martial arts, sports coach, or the like. Informed advisor may generate an advisor filter input at an advisor client device as described in more detail below. For instance and without limitation, advisor filter input may include a request for a particular machine-learning model utilized to generate a prognostic output. In yet another non-limiting example, advisor filter input may include a request for a plurality of prognostic outputs generated by prognostic label leaner and calculated confidence levels utilized to select a prognostic output from the plurality of prognostic outputs utilized to generate a prognostic output and/or ameliorative output. In yet another non-limiting example, advisor filter input may include a request for all machine-learning algorithms utilized to generate prognostic output and/or ameliorative output. In an embodiment, advisor filter input may not include any preference of diagnostic data 176 whereby all diagnostic data 176 may be transmitted to at least an informed advisor which may include for example and illustrative purposes only a biological extraction, training data, first training set, second trainings set, prognostic output and/or ameliorative output, prognostic output, ameliorative output, prognostic machine-learning model, ameliorative machine-learning model, regression models, lazy-learning models, confidence intervals, biological extraction classifier label, and the like.

With continued reference to FIG. 1, system 100 may include at least an advisor client device. Advisor client device 184 may include, without limitation, a display in communication with at least a server, display may include any display as described here. Advisor client device 184 may include an additional computing device, such as a mobile device, laptop, desktop computer, or the like; as a non-limiting example, advisor client device 184 may be a computer and/or workstation operated by a medical professional. Output may be displayed on at least an advisor client device 184 using an output graphical user interface.

With continued reference to FIG. 1, system 100 may include at least a user client device 188. User client device 188 may include any device suitable for use as an advisor client device 184 as described above. User client device 188 may operate on system 100 and may receive an output such as prognostic output and/or ameliorative output. In an embodiment, user client device 188 may communicate with advisor client device 184 and/or system 100 over a network, including any of the networks as described herein.

Figure 2:
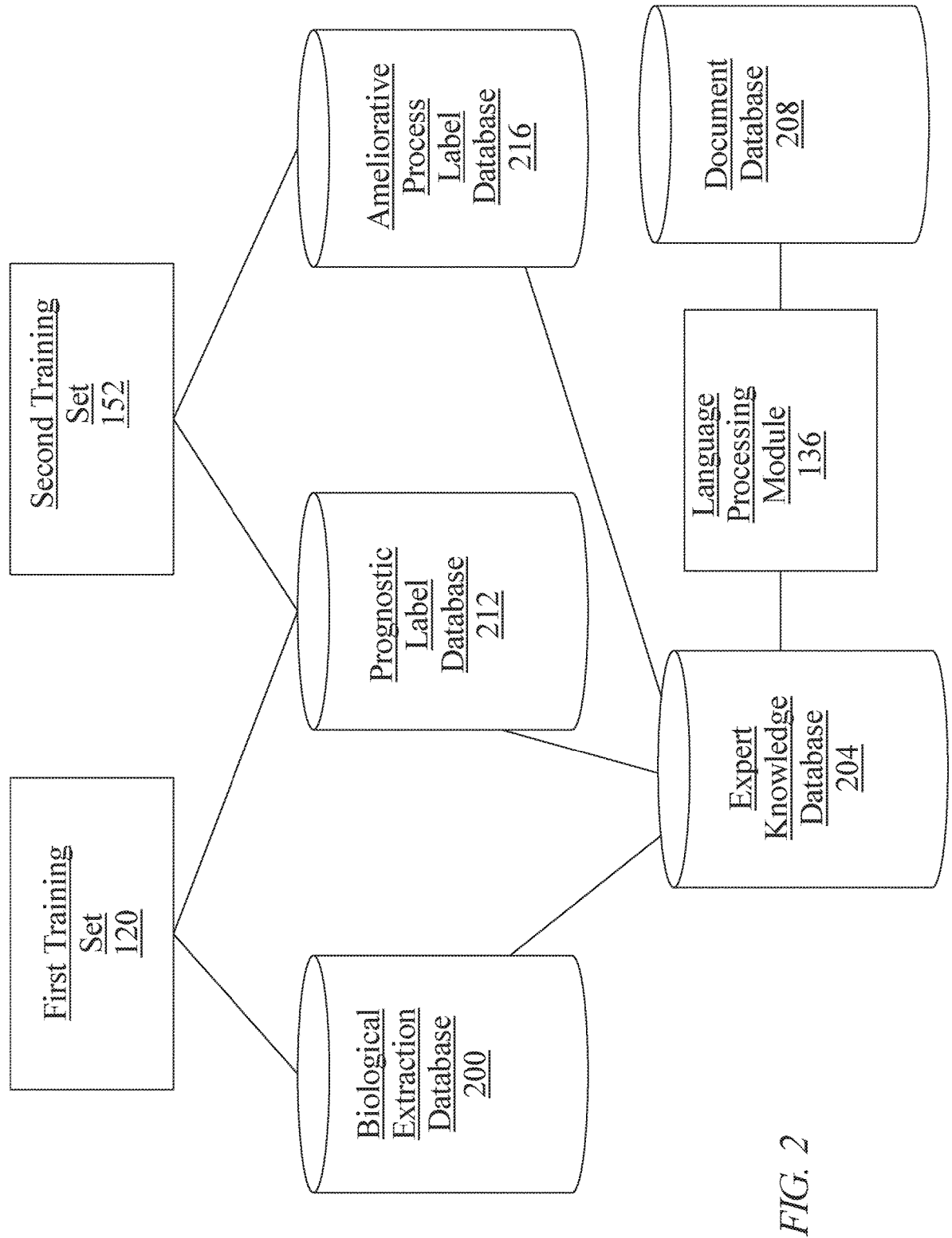
FIG. 2 is a block diagram illustrating embodiments of data storage facilities for use in disclosed systems and methods.

Referring now to FIG. 2, data incorporated in first training set 120 and/or second training set 152 may be incorporated in one or more databases. As a non-limiting example, one or elements of physiological state data 124 may be stored in and/or retrieved from a biological extraction database 200. A biological extraction database 200 may include any data structure for ordered storage and retrieval of data, which may be implemented as a hardware or software module. A biological extraction database 200 may be implemented, without limitation, as a relational database, a key-value retrieval datastore such as a NOSQL database, or any other format or structure for use as a datastore that a person skilled in the art would recognize as suitable upon review of the entirety of this disclosure. A biological extraction database 200 may include a plurality of data entries and/or records corresponding to elements of physiological data as described above. Data entries and/or records may describe, without limitation, data concerning particular physiological samples that have been collected; entries may describe reasons for collection of samples, such as without limitation one or more conditions being tested for, which may be listed with related prognostic labels. Data entries may include prognostic labels and/or other descriptive entries describing results of evaluation of past physiological samples, including diagnoses that were associated with such samples, prognoses and/or conclusions regarding likelihood of future diagnoses that were associated with such samples, and/or other medical or diagnostic conclusions that were derived. Such conclusions may have been generated by system 100 in previous iterations of methods, with or without validation of correctness by medical professionals. Data entries in a biological extraction database 200 may be flagged with or linked to one or more additional elements of information, which may be reflected in data entry cells and/or in linked tables such as tables related by one or more indices in a relational database; one or more additional elements of information may include data associating a physiological sample and/or a person from whom a physiological sample was extracted or received with one or more cohorts, including demographic groupings such as ethnicity, sex, age, income, geographical region, or the like, one or more common diagnoses or physiological attributes shared with other persons having physiological samples reflected in other data entries, or the like. Additional elements of information may include one or more categories of physiological data as described above. Additional elements of information may include descriptions of particular methods used to obtain physiological samples, such as without limitation physical extraction of blood samples or the like, capture of data with one or more sensor 108, and/or any other information concerning provenance and/or history of data acquisition. Persons skilled in the art, upon reviewing the entirety of this disclosure, will be aware of various ways in which data entries in a biological extraction database 200 may reflect categories, cohorts, and/or populations of data consistently with this disclosure.

With continued reference to FIG. 2, at least a server 104 and/or another device in system 100 may populate one or more fields in biological extraction database 200 using expert information, which may be extracted or retrieved from an expert knowledge database 204. An expert knowledge database 204 may include any data structure and/or data store suitable for use as a biological extraction database 200 as described below. Expert knowledge database 204 may include data entries reflecting one or more expert submissions of data such as may have been submitted according to any process described above in reference to FIG. 1, including without limitation by using first graphical user interface 132 and/or second graphical user interface 164. Expert knowledge database may include one or more fields generated by language processing module 136, such as without limitation fields extracted from one or more documents as described above. For instance, and without limitation, one or more categories of physiological data and/or related prognostic labels and/or categories of prognostic labels associated with an element of physiological state data 124 as described above may be stored in generalized from in an expert knowledge database 204 and linked to, entered in, or associated with entries in a biological extraction database 200. Documents may be stored and/or retrieved by at least a server 104 and/or language processing module 136 in and/or from a document database 208; document database 208 may include any data structure and/or data store suitable for use as biological extraction database 200 as described above. Documents in document database 208 may be linked to and/or retrieved using document identifiers such as URI and/or URL data, citation data, or the like; persons skilled in the art, upon reviewing the entirety of this disclosure, will be aware of various ways in which documents may be indexed and retrieved according to citation, subject matter, author, date, or the like as consistent with this disclosure.

With continued reference to FIG. 2, a prognostic label database 212, which may be implemented in any manner suitable for implementation of biological extraction database 200, may be used to store prognostic labels used in system 100, including any prognostic labels correlated with elements of physiological data in first training set 120 as described above; prognostic labels may be linked to or refer to entries in biological extraction database 200 to which prognostic labels correspond. Linking may be performed by reference to historical data concerning physiological samples, such as diagnoses, prognoses, and/or other medical conclusions derived from physiological samples in the past; alternatively or additionally, a relationship between a prognostic label and a data entry in biological extraction database 200 may be determined by reference to a record in an expert knowledge database 204 linking a given prognostic label to a given category of physiological sample as described above. Entries in prognostic label database 212 may be associated with one or more categories of prognostic labels as described above, for instance using data stored in and/or extracted from an expert knowledge database 204.

With continued reference to FIG. 2, first training set 120 may be populated by retrieval of one or more records from biological extraction database 200 and/or prognostic label database 212; in an embodiment, entries retrieved from biological extraction database 200 and/or prognostic label database 212 may be filtered and or select via query to match one or more additional elements of information as described above, so as to retrieve a first training set 120 including data belonging to a given cohort, demographic population, or other set, so as to generate outputs as described below that are tailored to a person or persons with regard to whom system 100 classifies physiological samples to prognostic labels as set forth in further detail below. Persons skilled in the art, upon reviewing the entirety of this disclosure, will be aware of various ways in which records may be retrieved from biological extraction database 200 and/or prognostic label database to generate a first training set 120 to reflect individualized group data pertaining to a person of interest in operation of system and/or method, including without limitation a person with regard to whom at least a physiological sample is being evaluated as described in further detail below. At least a server 104 may alternatively or additionally receive a first training set 120 and store one or more entries in biological extraction database 200 and/or prognostic label database 212 as extracted from elements of first training set.

With continued reference to FIG. 2, system 100 may include or communicate with an ameliorative process label database 216; an ameliorative process label database 216 may include any data structure and/or datastore suitable for use as a biological extraction database 200 as described above. An ameliorative process label database 216 may include one or more entries listing labels associated with one or more ameliorative processes as described above, including any ameliorative labels correlated with prognostic labels in second training set 152 as described above; ameliorative process labels may be linked to or refer to entries in prognostic label database 212 to which ameliorative process labels correspond. Linking may be performed by reference to historical data concerning prognostic labels, such as therapies, treatments, and/or lifestyle or dietary choices chosen to alleviate conditions associated with prognostic labels in the past; alternatively or additionally, a relationship between an ameliorative process label 160 and a data entry in prognostic label database 212 may be determined by reference to a record in an expert knowledge database 204 linking a given ameliorative process label 160 to a given category of prognostic label as described above. Entries in ameliorative process label database 216 may be associated with one or more categories of prognostic labels as described above, for instance using data stored in and/or extracted from an expert knowledge database 204.

With continued reference to FIG. 2, second training set 152 may be populated by retrieval of one or more records from prognostic label database 212 and/or ameliorative process label database 216; in an embodiment, entries retrieved from prognostic label database 212 and/or ameliorative process label database 216 may be filtered and or select via query to match one or more additional elements of information as described above, so as to retrieve a second training set 152 including data belonging to a given cohort, demographic population, or other set, so as to generate outputs as described below that are tailored to a person or persons with regard to whom system 100 classifies prognostic labels to ameliorative process labels as set forth in further detail below. Persons skilled in the art, upon reviewing the entirety of this disclosure, will be aware of various ways in which records may be retrieved from prognostic label database 212 and/or ameliorative process label database 216 to generate a second training set 152 to reflect individualized group data pertaining to a person of interest in operation of system and/or method, including without limitation a person with regard to whom at least a physiological sample is being evaluated as described in further detail below. At least a server 104 may alternatively or additionally receive a second training set 152 and store one or more entries in prognostic label database 212 and/or ameliorative process label database 216 as extracted from elements of second training set.

With continued reference to FIG. 2, at least a server 104 may receive an update to one or more elements of data represented in first training set 120 and/or second training set, and may perform one or more modifications to first training set 120 and/or second training set, or to biological extraction database 200, expert knowledge database 204, prognostic label database 212, and/or ameliorative process label database 216 as a result. For instance, a physiological sample may turn out to have been erroneously recorded; at least a server 104 may remove it from first training set, second training set, biological extraction database 200, expert knowledge database 204, prognostic label database 212, and/or ameliorative process label database 216 as a result. As a further example, a medical and/or academic paper, or a study on which it was based, may be revoked; at least a server 104 may remove it from first training set, second training set, biological extraction database 200, expert knowledge database 204, prognostic label database 212, and/or ameliorative process label database 216 as a result. Information provided by an expert may likewise be removed if the expert loses credentials or is revealed to have acted fraudulently.

Continuing to refer to FIG. 2, elements of data first training set, second training set, biological extraction database 200, expert knowledge database 204, prognostic label database 212, and/or ameliorative process label database 216 may have temporal attributes, such as timestamps; at least a server 104 may order such elements according to recency, select only elements more recently entered for first training set 120 and/or second training set, or otherwise bias training sets, database entries, and/or machine-learning models as described in further detail below toward more recent or less recent entries. Persons skilled in the art, upon reviewing the entirety of this disclosure, will be aware of various ways in which temporal attributes of data entries may be used to affect results of methods and/or systems as described herein.

Figure 3:
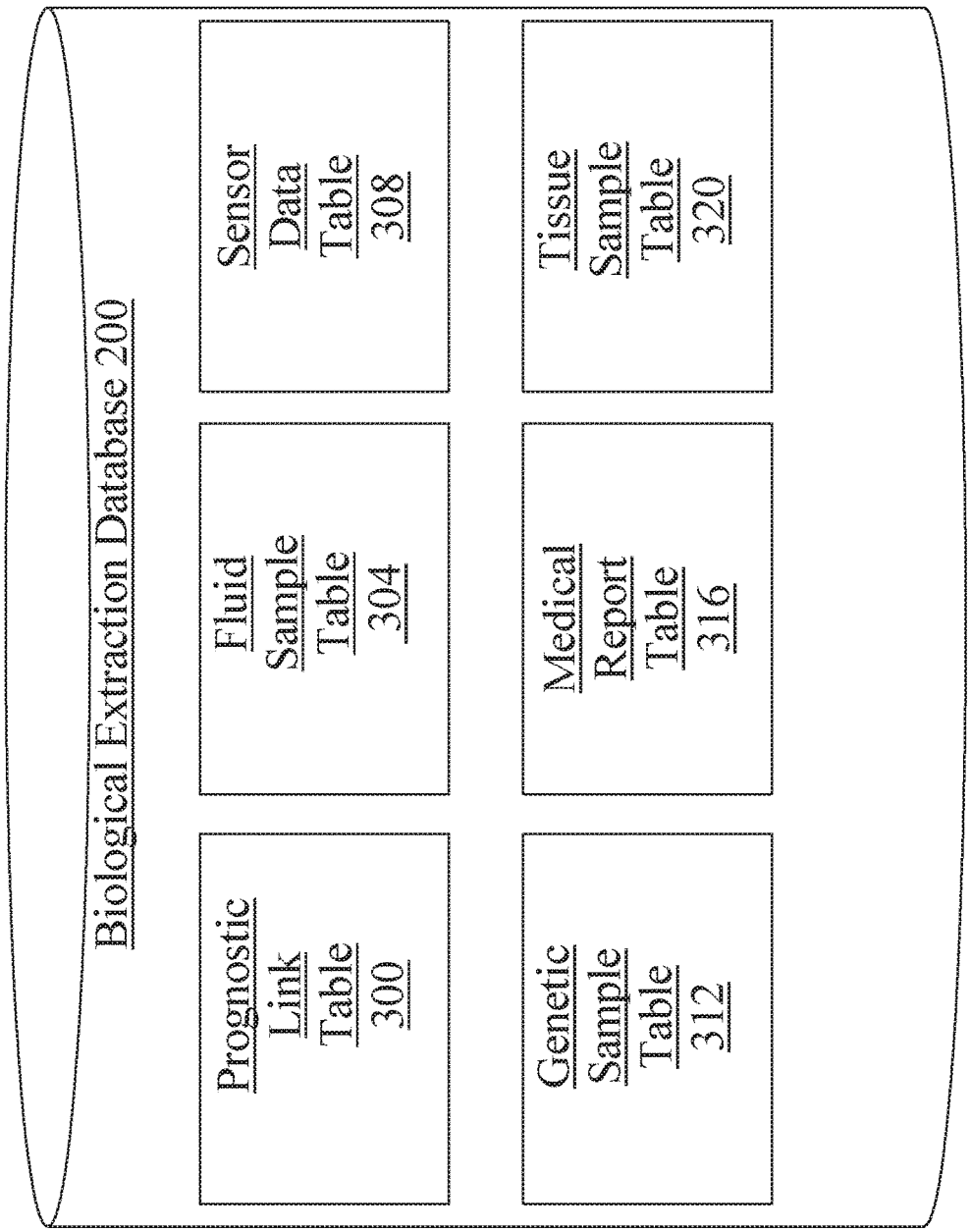
FIG. 3 is a block diagram illustrating an exemplary embodiment of a biological extraction database.

Referring now to FIG. 3, an exemplary embedment of biological extraction database 200 is illustrated, which may be implemented, without limitation, as a hardware or software module. Biological extraction database 200 may be implemented, without limitation, as a relational database, a key-value retrieval datastore such as a NOSQL database, or any other format or structure for use as a datastore that a person skilled in the art would recognize as suitable upon review of the entirety of this disclosure. One or more database tables in biological extraction database 200 may include, as a non-limiting example, a prognostic link table 300. Prognostic link table 300 may be a table relating physiological sample data as described above to prognostic labels; for instance, where an expert has entered data relating a prognostic label to a category of physiological sample data and/or to an element of physiological sample data via first graphical user interface 132 as described above, one or more rows recording such an entry may be inserted in prognostic link table 300. Alternatively or additionally, linking of prognostic labels to physiological sample data may be performed entirely in a prognostic label database as described below.

With continued reference to FIG. 3, biological extraction database 200 may include tables listing one or more samples according to sample source. For instance, and without limitation, biological extraction database 200 may include a fluid sample table 304 listing samples acquired from a person by extraction of fluids, such as without limitation blood, lymph cerebrospinal fluid, or the like. As another non-limiting example, biological extraction database 200 may include a sensor 108 data table 308, which may list samples acquired using one or more sensor 108, for instance as described in further detail below. As a further non-limiting example, biological extraction database 200 may include a genetic sample table 312, which may list partial or entire sequences of genetic material. Genetic material may be extracted and amplified, as a non-limiting example, using polymerase chain reactions (PCR) or the like. As a further example, also non-limiting, biological extraction database 200 may include a medical report table 316, which may list textual descriptions of medical tests, including without limitation radiological tests or tests of strength and/or dexterity or the like. Data in medical report table may be sorted and/or categorized using a language processing module 136, for instance, translating a textual description into a numerical value and a label corresponding to a category of physiological data; this may be performed using any language processing algorithm or algorithms as referred to in this disclosure. As another non-limiting example, biological extraction database 200 may include a tissue sample table 320, which may record physiological samples obtained using tissue samples. Tables presented above are presented for exemplary purposes only; persons skilled in the art will be aware of various ways in which data may be organized in biological extraction database 200 consistently with this disclosure.

Figure 4:
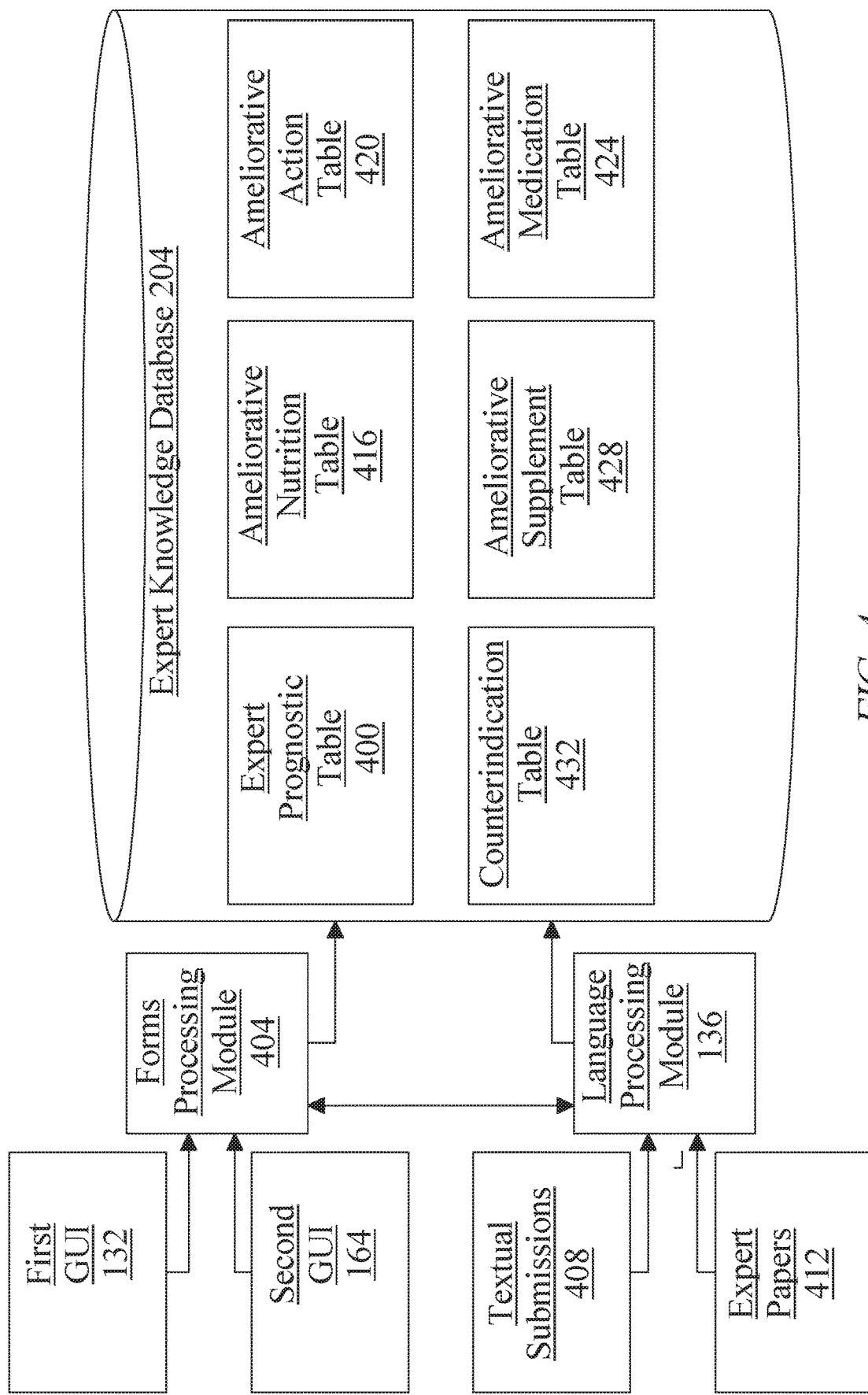
FIG. 4 is a block diagram illustrating an exemplary embodiment of an expert knowledge database.

Referring now to FIG. 4, an exemplary embodiment of an expert knowledge database 204 is illustrated. Expert knowledge database 204 may, as a non-limiting example, organize data stored in the expert knowledge database 204 according to one or more database tables. One or more database tables may be linked to one another by, for instance, common column values. For instance, a common column between two tables of expert knowledge database 200 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 4, one or more database tables in expert knowledge database 204 may include, as a non-limiting example, an expert prognostic table 400. Expert prognostic table 400 may be a table relating physiological sample data as described above to prognostic labels; for instance, where an expert has entered data relating a prognostic label to a category of physiological sample data and/or to an element of physiological sample data via first graphical user interface 132 as described above, one or more rows recording such an entry may be inserted in expert prognostic table 400. In an embodiment, a forms processing module 404 may sort data entered in a submission via first graphical user interface 132 by, for instance, sorting data from entries in the first graphical user interface 132 to related categories of data; for instance, data entered in an entry relating in the first graphical user interface 132 to a prognostic label may be sorted into variables and/or data structures for storage of prognostic labels, while data entered in an entry relating to a category of physiological data and/or an element thereof may be sorted into variables and/or data structures for the storage of, respectively, categories of physiological data or elements of physiological data. Where data is chosen by an expert from pre-selected entries such as drop-down lists, data may be stored directly; where data is entered in textual form, language processing module 136 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module 136 may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 408, such as accomplished by filling out a paper or PDF form and/or submitting narrative information, may likewise be processed using language processing module 136. Data may be extracted from expert papers 412, which may include without limitation publications in medical and/or scientific journals, by language processing module 136 via any suitable process as described herein. Persons skilled in the art, upon reviewing the entirety of this disclosure, will be aware of various additional methods whereby novel terms may be separated from already-classified terms and/or synonyms therefore, as consistent with this disclosure. Expert prognostic table 400 may include a single table and/or a plurality of tables; plurality of tables may include tables for particular categories of prognostic labels such as a current diagnosis table, a future prognosis table, a genetic tendency table, a metabolic tendency table, and/or an endocrinal tendency table (not shown), to name a few non-limiting examples presented for illustrative purposes only.

With continued reference to FIG. 4, one or more database tables in expert knowledge database 204 may include, as a further non-limiting example tables listing one or more ameliorative process labels; expert data populating such tables may be provided, without limitation, using any process described above, including entry of data from second graphical user interface 164 via forms processing module 404 and/or language processing module 136, processing of textual submissions 408, or processing of expert papers 412. For instance, and without limitation, an ameliorative nutrition table 416 may list one or more ameliorative processes based on nutritional instructions, and/or links of such one or more ameliorative processes to prognostic labels, as provided by experts according to any method of processing and/or entering expert data as described above. As a further example an ameliorative action table 420 may list one or more ameliorative processes based on instructions for actions a user should take, including without limitation exercise, meditation, and/or cessation of harmful eating, substance abuse, or other habits, and/or links of such one or more ameliorative processes to prognostic labels, as provided by experts according to any method of processing and/or entering expert data as described above. As an additional example, an ameliorative supplement table 424 may list one or more ameliorative processes based on nutritional supplements, such as vitamin pills or the like, and/or links of such one or more ameliorative processes to prognostic labels, as provided by experts according to any method of processing and/or entering expert data as described above. As a further non-limiting example, an ameliorative medication table 428 may list one or more ameliorative processes based on medications, including without limitation over-the-counter and prescription pharmaceutical drugs, and/or links of such one or more ameliorative processes to prognostic labels, as provided by experts according to any method of processing and/or entering expert data as described above. As an additional example, a counterindication table 432 may list one or more counterindications for one or more ameliorative processes; counterindications may include, without limitation allergies to one or more foods, medications, and/or supplements, side-effects of one or more medications and/or supplements, interactions between medications, foods, and/or supplements, exercises that should not be used given one or more medical conditions, injuries, disabilities, and/or demographic categories, or the like. Tables presented above are presented for exemplary purposes only; persons skilled in the art will be aware of various ways in which data may be organized in expert knowledge database 204 consistently with this disclosure.

Figure 5:
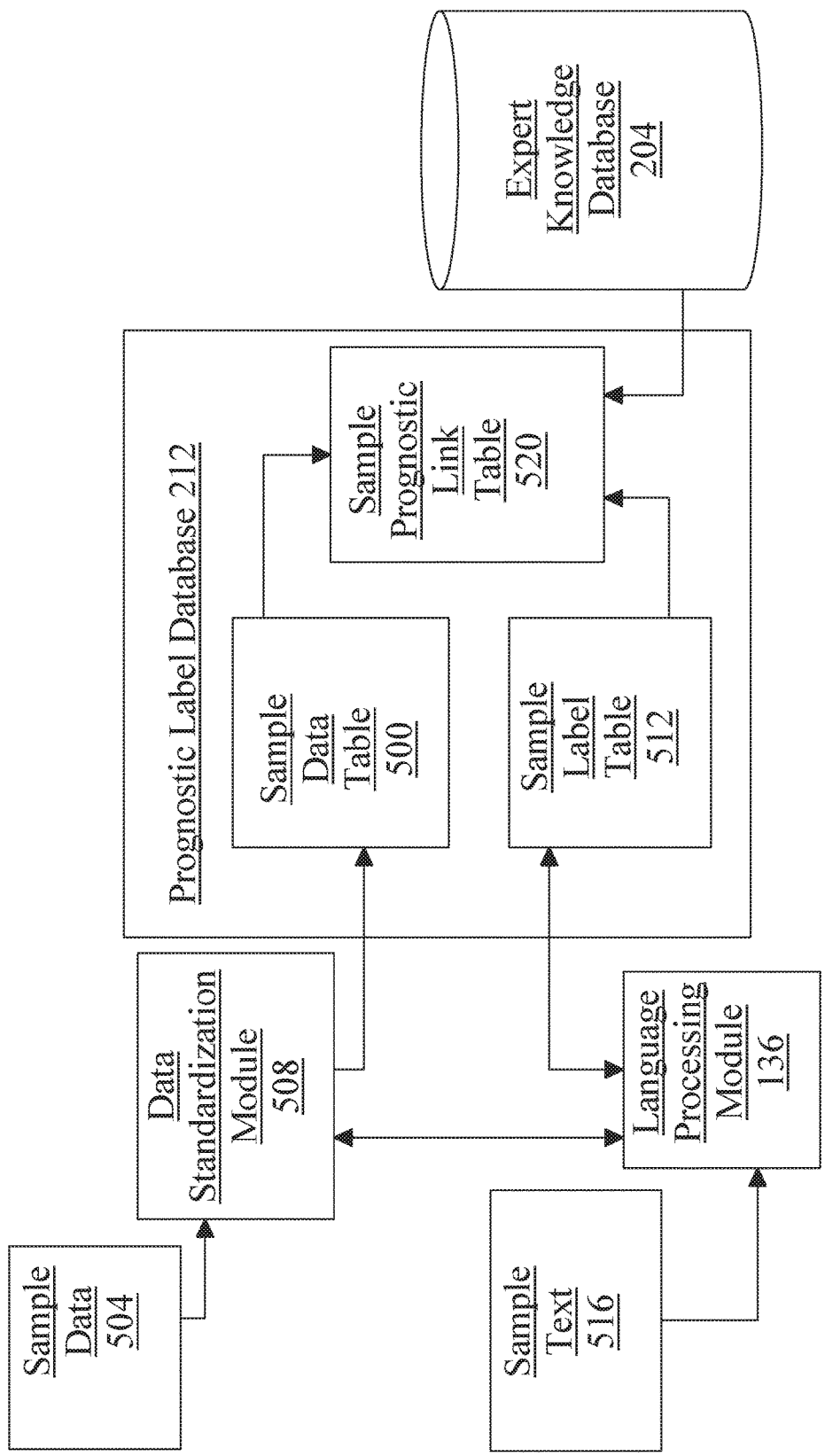
FIG. 5 is a block diagram illustrating an exemplary embodiment of a prognostic label database.

Referring now to FIG. 5, an exemplary embodiment of a prognostic label database 212 is illustrated. Prognostic label database 212 may, as a non-limiting example, organize data stored in the prognostic label database 212 according to one or more database tables. One or more database tables may be linked to one another by, for instance, common column values. For instance, a common column between two tables of prognostic label database 212 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 5, one or more database tables in prognostic label database 212 may include, as a non-limiting example, a sample data table 500. Sample data table 500 may be a table listing sample data, along with, for instance, one or more linking columns to link such data to other information stored in prognostic label database 212. In an embodiment, sample data 504 may be acquired, for instance from biological extraction database 200, in a raw or unsorted form, and may be translated into standard forms, such as standard units of measurement, labels associated with particular physiological data values, or the like; this may be accomplished using a data standardization module 508, which may perform unit conversions. Data standardization module 508 may alternatively or additionally map textual information, such as labels describing values tested for or the like, using language processing module 136 or equivalent components and/or algorithms thereto.

Continuing to refer to FIG. 5, prognostic label database 212 may include a sample label table 512; sample label table 512 may list prognostic labels received with and/or extracted from physiological samples, for instance as received in the form of sample text 516. A language processing module 136 may compare textual information so received to prognostic labels and/or form new prognostic labels according to any suitable process as described above. Sample prognostic link table may combine samples with prognostic labels, as acquired from sample label table and/or expert knowledge database 204; combination may be performed by listing together in rows or by relating indices or common columns of two or more tables to each other. Tables presented above are presented for exemplary purposes only; persons skilled in the art will be aware of various ways in which data may be organized in expert knowledge database 204 consistently with this disclosure.

Figure 6:
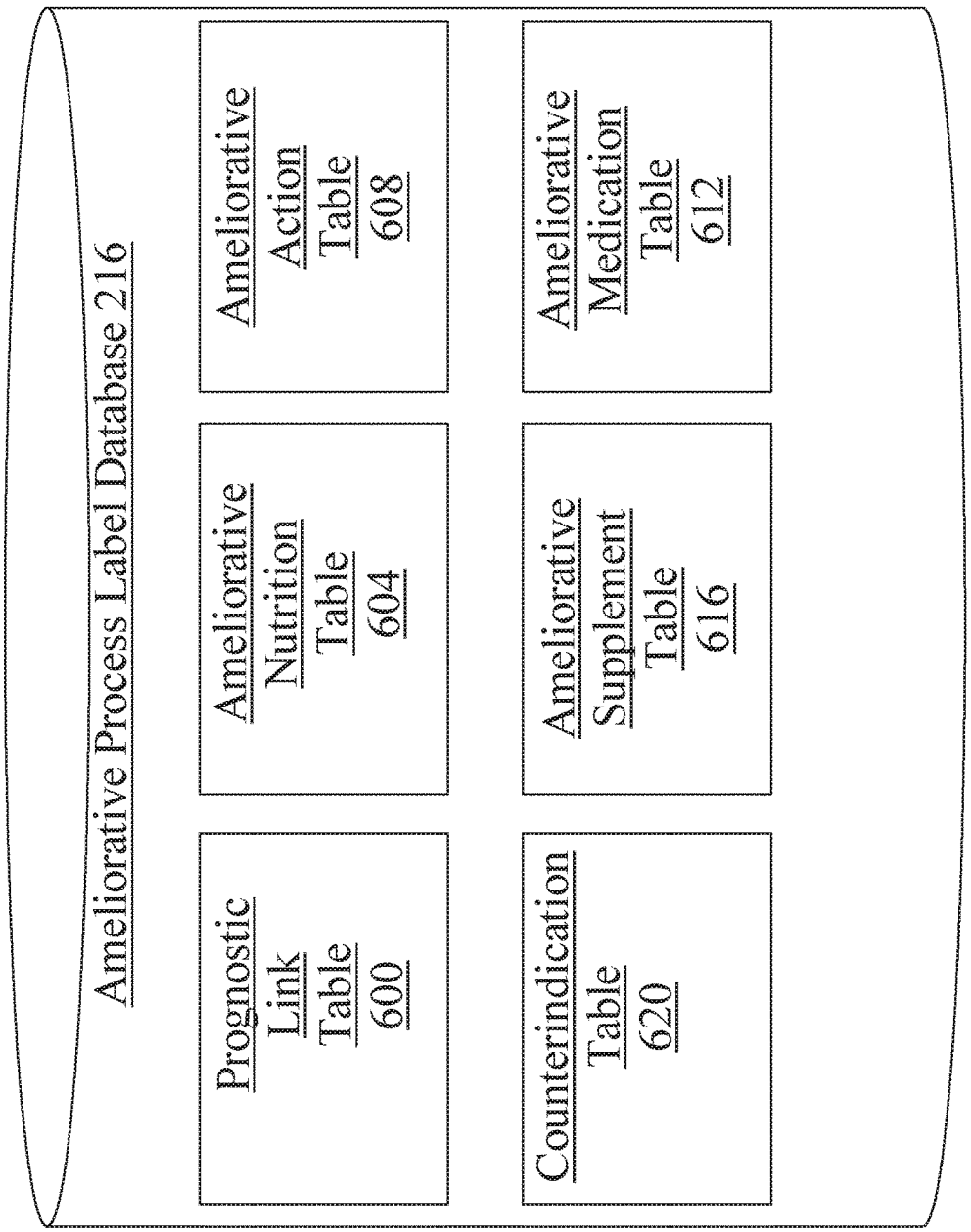
FIG. 6 is a block diagram illustrating an exemplary embodiment of an ameliorative process label database.

Referring now to FIG. 6, an exemplary embodiment of an ameliorative process label database 216 is illustrated. Ameliorative process label database 216 may, as a non-limiting example, organize data stored in the ameliorative process label database 216 according to one or more database tables. One or more database tables may be linked to one another by, for instance, common column values. For instance, a common column between two tables of ameliorative process label database 216 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 6, ameliorative process label database 216 may include a prognostic link table 600; prognostic link table may link ameliorative process data to prognostic label data, using any suitable method for linking data in two or more tables as described above. Ameliorative process label database 216 may include an ameliorative nutrition table 604, which may list one or more ameliorative processes based on nutritional instructions, and/or links of such one or more ameliorative processes to prognostic labels, for instance as provided by experts according to any method of processing and/or entering expert data as described above, and/or using one or more machine-learning processes as set forth in further detail below. As a further example an ameliorative action table 608 may list one or more ameliorative processes based on instructions for actions a user should take, including without limitation exercise, meditation, and/or cessation of harmful eating, substance abuse, or other habits, and/or links of such one or more ameliorative processes to prognostic labels, as provided by experts according to any method of processing and/or entering expert data as described above and/or using one or more machine-learning processes as set forth in further detail below. As an additional example, an ameliorative supplement table 612 may list one or more ameliorative processes based on nutritional supplements, such as vitamin pills or the like, and/or links of such one or more ameliorative processes to prognostic labels, as provided by experts according to any method of processing and/or entering expert data as described above and/or using one or more machine-learning processes as set forth in further detail below. As a further non-limiting example, an ameliorative medication table 616 may list one or more ameliorative processes based on medications, including without limitation over-the-counter and prescription pharmaceutical drugs, and/or links of such one or more ameliorative processes to prognostic labels, as provided by experts according to any method of processing and/or entering expert data as described above and/or using one or more machine-learning processes as set forth in further detail below. As an additional example, a counter-indication table 620 may list one or more counter-indications for one or more ameliorative processes; counterindications may include, without limitation allergies to one or more foods, medications, and/or supplements, side-effects of one or more medications and/or supplements, interactions between medications, foods, and/or supplements, exercises that should not be used given one or more medical conditions, injuries, disabilities, and/or demographic categories, or the like; this may be acquired using expert submission as described above and/or using one or more machine-learning processes as set forth in further detail below. Tables presented above are presented for exemplary purposes only; persons skilled in the art will be aware of various ways in which data may be organized in ameliorative process database 216 consistently with this disclosure.

Figure 7:
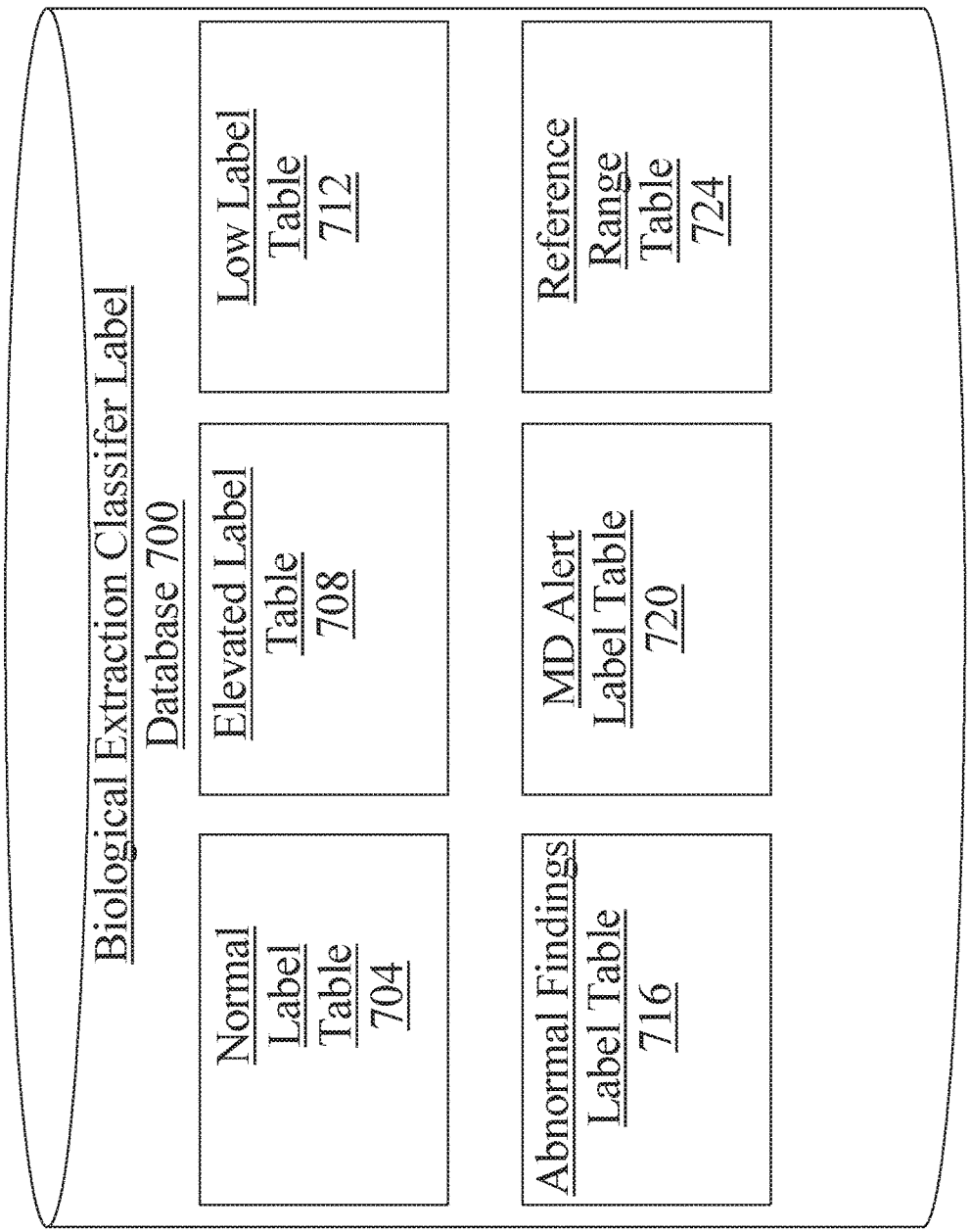
FIG. 7 is a block diagram illustrating an exemplary embodiment of a biological extraction classifier label database.

Referring now to FIG. 7, an exemplary embodiment of biological extraction classifier label database 700 is illustrated. Biological extraction classifier label database 700 may, as a non-limiting example, organize data stored in the biological extraction classifier label database 700 according to one or more database tables. One or more database tables may be linked to one another by, for instance, common column values. For instance, a common column between two tables of biological extraction classifier label database 700 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

With continued reference to FIG. 7, biological extraction classifier label database 700 may include any data structure for ordered storage and retrieval of data, which may be implemented as a hardware or software module, and which may be implemented as any database structure suitable for use as biological extraction database 200. Biological extraction classifier label database 700 may include normal label table 704; normal label table 704 may list one or more biological extractions containing a "normal" classifier label indicating that a given biological extraction has fallen within a given reference range. For example, normal label table 704 may include a blood hemoglobin level for a female of 14.0 grams per deciliter (g/dL) containing a normal classifier label as compared to a reference range of 13.5 to 17.5 grams per deciliter (g/dL). Biological extraction classifier label database 700 may include elevated label table 708; elevated label table 708 may list one or more biological extractions containing an "elevated" classifier label indicating a given biological extraction has fallen above a given reference range. For example, elevated label table 708 may include a urine sample containing a protein level of 37 milligrams per deciliter (mg/dL) as compared to a reference range of 0 to 20 milligrams per deciliter (mg/dL). Biological extraction classifier label database 700 may include low label table 712; low label table 712 may list one or more biological extractions containing a "low" classifier label indicating a given biological extraction has fallen below a given reference range. For example, low label table 712 may include a salivary sample containing a progesterone level of 55 nanograms per milliliter (ng/ml) as compared to a reference range of 75-250 nanograms per milliliter (ng/ml). Biological extraction classifier label database 700 may include abnormal findings label table 716; abnormal findings label table 716 may list one or more biological extractions containing an abnormal findings label indicating a given biological extraction has not fallen within a given reference range. For example, abnormal findings table 716 may include a hemoglobin A1c level OF 8% as compared to a reference range of 4-5.6%. Biological extraction classifier label database 700 may include MD alert label table 720; MD alert label table 720 may include one or more biological extractions containing an MD alert label indicating that a medical doctor needs to be consulted, which may be due to abnormally high or low levels, dangerous conditions that may be indicated as a result of a particular level, and/or an alert that time is of the essence and medical attention is warranted immediately. For example, MD alert label table 720 may include a blood serum pH of 6.5 as compared to a reference range of 7.35 to 7.45 which may indicate possible diabetic ketoacidosis and warrant medical attention immediately. Biological extraction classifier label database 700 may include reference range table 724; reference range table 724 may list one or more reference ranges for one or more biological extractions. Reference ranges may be organized and categorized by various categories and factors such as reference ranges for particular ages of individuals, gender, co-morbid conditions, menstrual phase, menstrual state, and the like.

Figure 8:
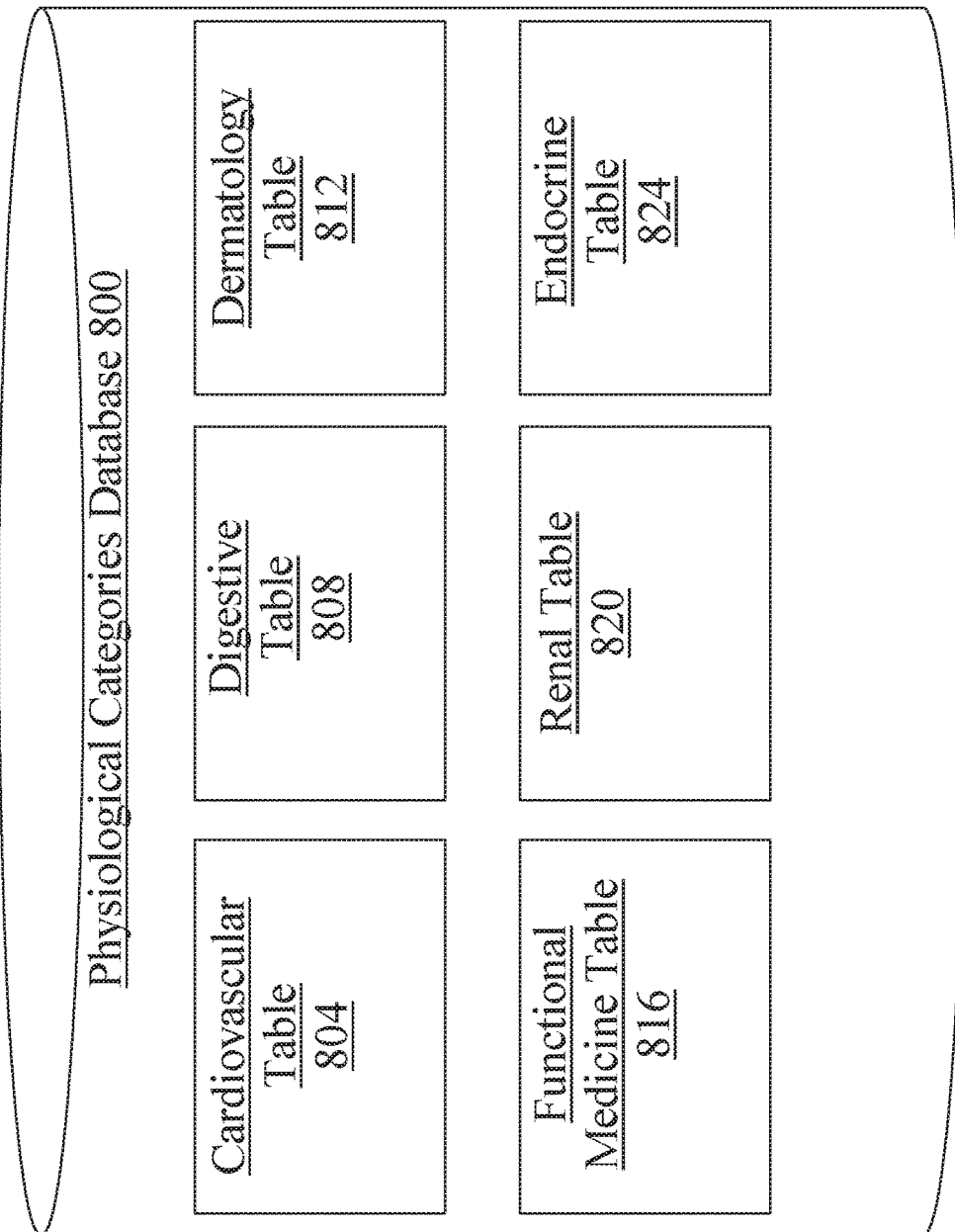
FIG. 8 is a block diagram illustrating an exemplary embodiment of a physiological categories database.

Referring now to FIG. 8, an exemplary embodiment of physiological categories database 800 is illustrated. Physiological categories database 800 may, as a non-limiting example, organize data stored in the physiological categories database 800 according to one or more database tables. One or more database tables may be linked to one another by, for instance, common column values. For instance, a common column between two tables of physiological categories database 800 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

With continued reference to FIG. 8, physiological categories database 800 include any data structure for ordered storage and retrieval of data, which may be implemented as a hardware or software module, and which may be implemented as any database structure suitable for use as biological extraction database 200. Physiological categories database 800 may include cardiovascular table 804; cardiovascular table 804 may include physiological state data 124 and/or biological extractions categorized as relating to cardiovascular system. For example, cardiovascular table 804 may include data relating to heart health such as lipid levels, troponin levels, electrocardiograms, triglycerides, myoglobin, creatine kinase, and the like. Physiological categories database 800 may include digestive table 808; digestive table 808 may include physiological state data 124 and/or biological extractions categorized as relating to digestive system. For example, digestive table 808 may include data relating to digestive health such as iron levels, ferritin levels, microbiome species within gut, *Candida Albicans* species, calprotectin levels, lactoferrin levels, neopterin levels, lysozyme levels, and the like. Physiological categories database 800 may include dermatology table 812; dermatology table 812 may include physiological state data 124 and/or biological extractions categorized as relating to dermatology. For example, dermatology table 812 may include skin biopsies, mole biopsies, immunoglobulin a (IGA) levels, cutaneous electron micrographs, immunohistochemical hybridization stains, histochemical hybridization stains, and in situ hybridization stains. Physiological categories database 800 may include functional medicine table 816; functional medicine table 816 may include physiological state data 124 and/or biological extractions categorized as relating to functional medicine. For example, functional medicine table 816 may include neurotransmitter levels, hormone levels, basal body temperature, total T4 levels, free T4 levels, free T3 levels, gut metabolic markers, digestion absorption markers, immune system hyperactivity, eosinophil protein x levels, calprotectin levels, and the like. Physiological categories database 800 may include renal table 820; renal table 820 may include physiological state data 124 and/or biological extractions categorized as relating to the renal system. For example, renal table 820 may include albumin levels, creatinine levels, glomerular filtration rate, creatinine clearance, blood urea nitrogen, urinalysis, urine protein, microalbuminuria and the like. Physiological categories database 800 may include endocrine table 824; endocrine table 824 may include physiological state data 124 and/or biological extractions categorized as relating to the endocrine system. For example, endocrine table 824 may include aldosterone levels, serum cortisol levels, hirsutism panel, adiponectin, fasting glucose level, insulin levels, hemoglobin A1C with calculated mean plasma glucose (MPG), prolactin, pituitary hormone level, and the like. In an embodiment, physiological state data 124 and/or biological extractions may be categorized to one or more tables contained within physiological categories database 800. Other tables not illustrated but which may be included in physiological categories database 800 may include for example, circulatory table, excretory table, immune table, lymphatic table, muscular table, neural table, urinary table, respiratory table, reproductive table, and the like.

Figure 9:
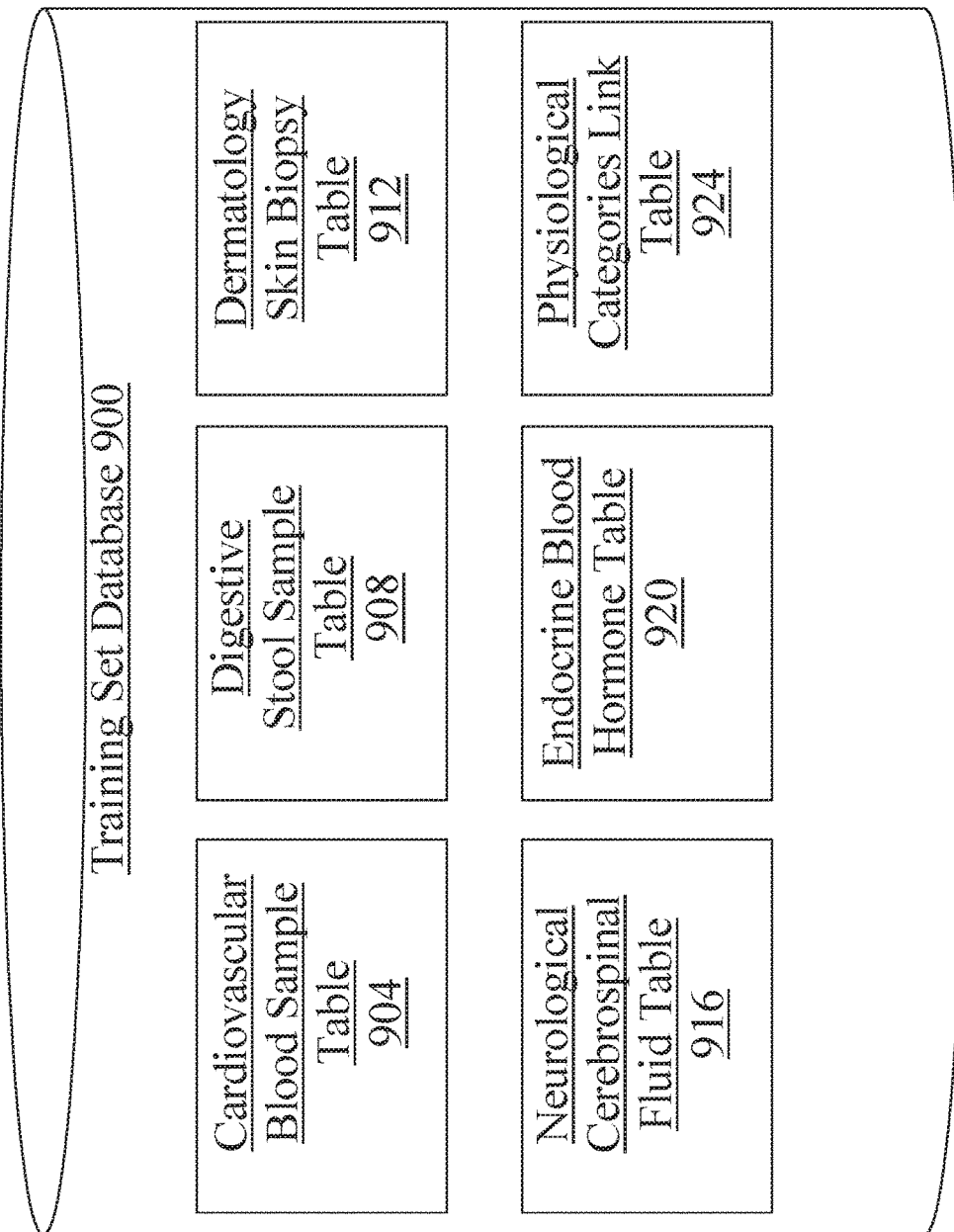
FIG. 9 is a block diagram illustrating an exemplary embodiment of a training set database.

Referring now to FIG. 9, an exemplary embodiment of training set database 900 is illustrated. Training set database 900 may, as a non-limiting example, organize data stored in the training set database 900 according to one or more database tables. One or more database tables may be linked to one another by, for instance, common column values. For instance, a common column between two tables of training set database 900 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

With continued reference to FIG. 9, training set database 900 may include any data structure for ordered storage and retrieval of data, which may be implemented as a hardware or software module, and which may be implemented as any database structure suitable for use as biological extraction database 200. Training set database 900 may include one or more tables containing training sets categorized by physiological category and sample type. Training set database 900 may include cardiovascular blood sample table 904; cardiovascular blood sample table 904 may include training sets containing physiological state data 124 categorized as relating to cardiovascular system and which include physiological data extracted from a blood sample. For example, blood sample table 904 may include training sets containing physiological state data 124 such as total cholesterol levels or total triglyceride levels. Training set database 900 may include digestive stool sample table 908; digestive stool sample table 908 may include training sets containing physiological state data 124 categorized as relating to digestive system and which include physiological data extracted from a stool sample. For example, digestive stool sample table 908 may include training sets containing physiological state data 124 such as an ova and parasite exam. Training set database 900 may include dermatology skin biopsy table 912; dermatology skin biopsy table 912 may include training sets containing physiological state data 124 categorized as relating to dermatology system and which include physiological data extracted from a skin biopsy. For example, skin biopsy table 912 may include training sets containing physiological state data 124 such as a skin sample removed from an area on the body such as the elbow or knee and the like. Training set database 900 may include neurological cerebrospinal fluid table 916; neurological cerebrospinal fluid table 916 may include training sets containing physiological state data 124 categorized as relating to neurology system and which include physiological data extracted from cerebrospinal fluid. For example, neurological cerebrospinal fluid table 916 may include for example pressure measurement, cell count, white cell differential, glucose levels, protein levels, gram stain, culture, and the like. Training set database 900 may include endocrine blood hormone table 920; endocrine blood hormone table 920 may include training sets containing physiological state data 124 categorized as relating to endocrine system and which include physiological data extracted from blood sample. For example, endocrine blood hormone table 920 may include for example estradiol levels, progesterone levels, follicle stimulating hormone, testosterone, thyroid stimulating hormone (TSH), thyroxine (T4), and the like. Training set database 900 may include physiological categories link table 924; physiological categorizes link table 924 may relate physiological state data 124 and/or biological extractions to physiological categories. For example, physiological categories link table 924 may include entries from an expert relating physiological state data 124 to a physiological category. In an embodiment, training sets contained within training set database and contained within one or more tables may include at least a data entry of a first training set 120 that includes at least an element of physiological state data 124 and at least a correlated first prognostic label. In an embodiment, first training set 120 may be correlated to a second training set 152 that includes at least a second data entry of a second training set 152 where each second data entry of the second training set 152 includes at least a second prognostic label 156 and at least a correlated ameliorative process label. In an embodiment, training sets contained within training set database 900 and/or data entries contained with each training set may be listed and contained within more than one table within training set database 900. In an embodiment, training set database 900 may include other tables not illustrated including for example cardiovascular saliva sample table, digestive blood sample table, dermatology blood sample table, neurological saliva sample, neurological amniotic sample, neurological hair sample, endocrine hair sample, and the like.

Figure 10:
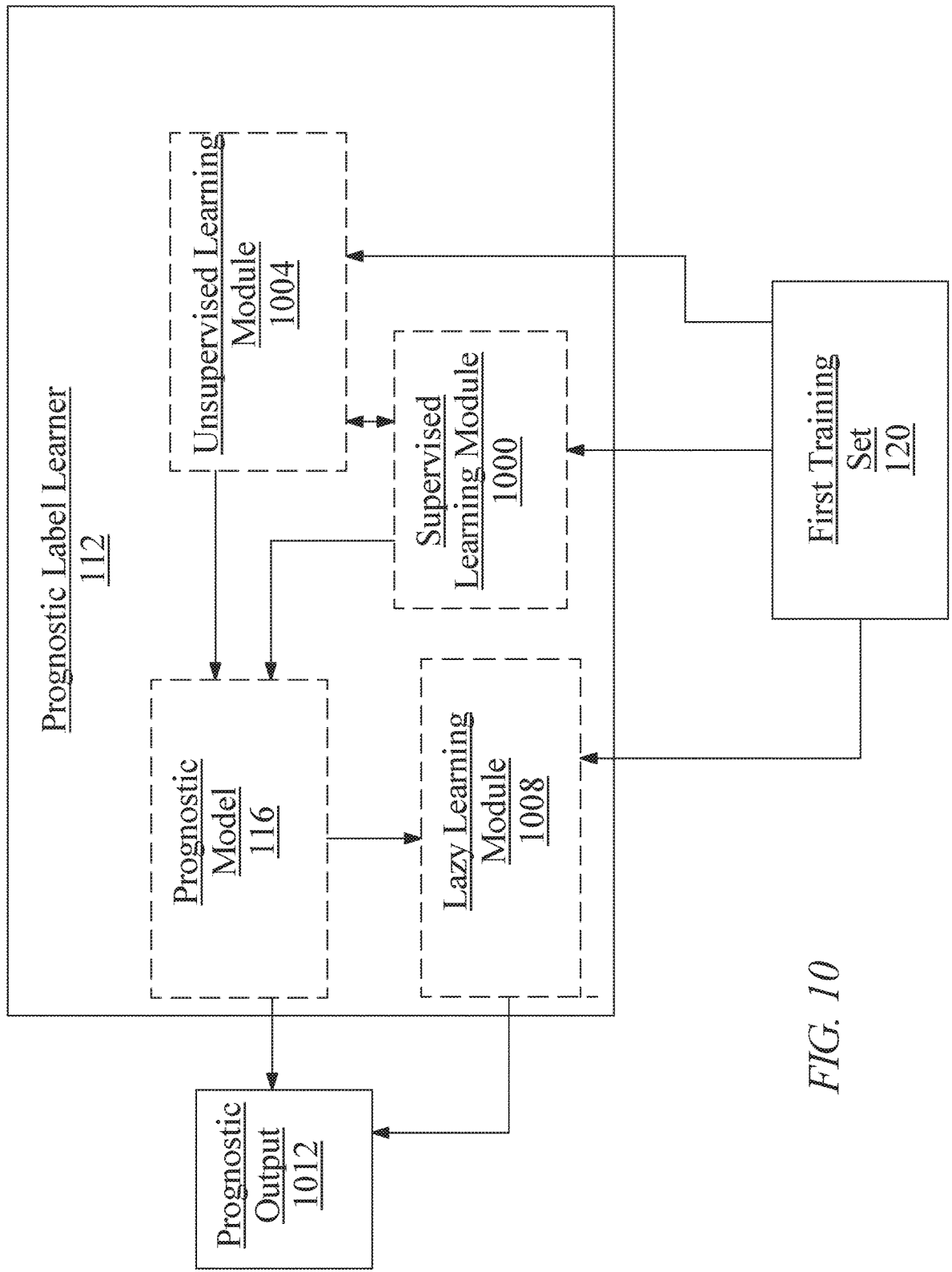
FIG. 10 is a block diagram illustrating an exemplary embodiment of a prognostic label learner.

Referring now to FIG. 10, an exemplary embodiment of prognostic label learner 112 is illustrated. Machine-learning algorithms used by prognostic label learner 112 may include supervised machine-learning algorithms, which may, as a non-limiting example be executed using a supervised learning module 1000 executing on at least a server 104 and/or on another computing device in communication with at least a server 104, which may include any hardware or software module. Supervised machine-learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of physiological data as inputs, prognostic labels as outputs, and a scoring function representing a desired form of relationship to be detected between elements of physiological data and prognostic labels; scoring function may, for instance, seek to maximize the probability that a given element of physiological state data 124 and/or combination of elements of physiological data is associated with a given prognostic label and/or combination of prognostic labels to minimize the probability that a given element of physiological state data 124 and/or combination of elements of physiological state data 124 is not associated with a given prognostic label and/or combination of prognostic labels. Scoring function may be expressed as a risk function representing an "expected loss" of an algorithm relating inputs to outputs, where loss is computed as an error function representing a degree to which a prediction generated by the relation is incorrect when compared to a given input-output pair provided in first training set. Persons skilled in the art, upon reviewing the entirety of this disclosure, will be aware of various possible variations of supervised machine-learning algorithms that may be used to determine relation between elements of physiological data and prognostic labels. In an embodiment, one or more supervised machine-learning algorithms may be restricted to a particular domain for instance, a supervised machine-learning process may be performed with respect to a given set of parameters and/or categories of parameters that have been suspected to be related to a given set of prognostic labels, and/or are specified as linked to a medical specialty and/or field of medicine covering a particular set of prognostic labels. As a non-limiting example, a particular set of blood test biomarkers and/or sensor 108 data may be typically used by cardiologists to diagnose or predict various cardiovascular conditions, and a supervised machine-learning process may be performed to relate those blood test biomarkers and/or sensor 108 data to the various cardiovascular conditions; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate prognostic labels. Additional supervised learning processes may be performed without domain restrictions to detect, for instance, previously unknown and/or unsuspected relationships between physiological data and prognostic labels.

With continued reference to FIG. 10, machine-learning algorithms may include unsupervised processes; unsupervised processes may, as a non-limiting example, be executed by an unsupervised learning module 1004 executing on at least a server 104 and/or on another computing device in communication with at least a server 104, which may include any hardware or software module. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, prognostic label learner 112 and/or at least a server 104 may perform an unsupervised machine-learning process on first training set 120, which may cluster data of first training set 120 according to detected relationships between elements of the first training set 120, including without limitation correlations of elements of physiological state data 124 to each other and correlations of prognostic labels to each other; such relations may then be combined with supervised machine-learning results to add new criteria for prognostic label learner 112 to apply in relating physiological state data 124 to prognostic labels. As a non-limiting, illustrative example, an unsupervised process may determine that a first element of physiological data acquired in a blood test correlates closely with a second element of physiological data, where the first element has been linked via supervised learning processes to a given prognostic label, but the second has not; for instance, the second element may not have been defined as an input for the supervised learning process, or may pertain to a domain outside of a domain limitation for the supervised learning process. Continuing the example a close correlation between first element of physiological state data 124 and second element of physiological state data 124 may indicate that the second element is also a good predictor for the prognostic label; second element may be included in a new supervised process to derive a relationship or may be used as a synonym or proxy for the first physiological element by prognostic label learner 112.

Still referring to FIG. 10, at least a server 104 and/or prognostic label learner 112 may detect further significant categories of physiological data, relationships of such categories to prognostic labels, and/or categories of prognostic labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to at least a server 104, prognostic label learner 112 and/or at least a server 104 may continuously or iteratively perform unsupervised machine-learning processes to detect relationships between different elements of the added and/or overall data; in an embodiment, this may enable at least a server 104 to use detected relationships to discover new correlations between known biomarkers, prognostic labels, and/or ameliorative labels and one or more elements of data in large bodies of data, such as genomic, proteomic, and/or microbiome-related data, enabling future supervised learning and/or lazy learning processes as described in further detail below to identify relationships between, e.g., particular clusters of genetic alleles and particular prognostic labels and/or suitable ameliorative labels. Use of unsupervised learning may greatly enhance the accuracy and detail with which system may detect prognostic labels and/or ameliorative labels.

With continued reference to FIG. 10, unsupervised processes may be subjected to domain limitations. For instance, and without limitation, an unsupervised process may be performed regarding a comprehensive set of data regarding one person, such as a comprehensive medical history, set of test results, and/or physiological data such as genomic, proteomic, and/or other data concerning that persons. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of physiological data, a group of people having a shared value for an element and/or category of prognostic label, and/or a group of people having a shared value and/or category of ameliorative label; as illustrative examples, cohort could include all people having a certain level or range of levels of blood triglycerides, all people diagnosed with type II diabetes, all people who regularly run between 10 and 15 miles per week, or the like. Persons skilled in the art, upon reviewing the entirety of this disclosure, will be aware of a multiplicity of ways in which cohorts and/or other sets of data may be defined and/or limited for a particular unsupervised learning process.

Still referring to FIG. 10, prognostic label learner 112 may alternatively or additionally be designed and configured to generate at least a prognostic output by executing a lazy learning process as a function of the first training set 120 and the at least a biological extraction; lazy learning processes may be performed by a lazy learning module 1008 executing on at least a server 104 and/or on another computing device in communication with at least a server 104, which may include any hardware or software module. A lazy-learning process and/or protocol, which may alternatively be referred to as a "lazy loading" or "call-when-needed" process and/or protocol, may be a process whereby machine-learning is conducted upon receipt of an input to be converted to an output, by combining the input and training set to derive the algorithm to be used to produce the output on demand. For instance, an initial set of simulations may be performed to cover a "first guess" at a prognostic label associated with biological extraction, using first training set 120. As a non-limiting example, an initial heuristic may include a ranking of prognostic labels according to relation to a test type of at least a biological extraction, one or more categories of physiological data identified in test type of at least a biological extraction, and/or one or more values detected in at least a biological extraction; ranking may include, without limitation, ranking according to significance scores of associations between elements of physiological data and prognostic labels, for instance as calculated as described above. Heuristic may include selecting some number of highest-ranking associations and/or prognostic labels. Prognostic label learner 112 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate prognostic outputs as described in this disclosure, including without limitation lazy learning applications of machine-learning algorithms as described in further detail below.

In an embodiment, and continuing to refer to FIG. 10, prognostic label learner 112 may generate a plurality of prognostic labels having different implications for a particular person. For instance, where the at least a biological extraction includes a result of a dexterity test, a low score may be consistent with amyotrophic lateral sclerosis, Parkinson's disease, multiple sclerosis, and/or any number of less sever disorders or tendencies associated with lower levels of dexterity. In such a situation, prognostic label learner 112 and/or at least a server 104 may perform additional processes to resolve ambiguity. Processes may include presenting multiple possible results to a medical practitioner, informing the medical practitioner that one or more follow-up tests and/or biological extractions are needed to further determine a more definite prognostic label. Alternatively or additionally, processes may include additional machine-learning steps; for instance, where reference to a model generated using supervised learning on a limited domain has produced multiple mutually exclusive results and/or multiple results that are unlikely all to be correct, or multiple different supervised machine-learning models in different domains may have identified mutually exclusive results and/or multiple results that are unlikely all to be correct. In such a situation, prognostic label learner 112 and/or at least a server 104 may operate a further algorithm to determine which of the multiple outputs is most likely to be correct; algorithm may include use of an additional supervised and/or unsupervised model. Alternatively or additionally, prognostic label learner 112 may perform one or more lazy learning processes using a more comprehensive set of user data to identify a more probably correct result of the multiple results. Results may be presented and/or retained with rankings, for instance to advise a medical professional of the relative probabilities of various prognostic labels being correct; alternatively or additionally, prognostic labels associated with a probability of correctness below a given threshold and/or prognostic labels contradicting results of the additional process, may be eliminated. As a non-limiting example, an endocrinal test may determine that a given person has high levels of dopamine, indicating that a poor pegboard performance is almost certainly not being caused by Parkinson's disease, which may lead to Parkinson's being eliminated from a list of prognostic labels associated with poor pegboard performance, for that person. Similarly, a genetic test may eliminate Huntington's disease, or another disease definitively linked to a given genetic profile, as a cause. Persons skilled in the art, upon reviewing the entirety of this disclosure, will be aware of various ways in which additional processing may be used to determine relative likelihoods of prognostic labels on a list of multiple prognostic labels, and/or to eliminate some labels from such a list. Prognostic output 1012 may be provided to user output device as described in further detail below.

With continued reference to FIG. 10, prognostic label learner 112 may generate a plurality of prognostic outputs each containing a ranked prognostic probability score as a function of at least a biological extraction, at least a first training set, and at least a prognostic machine-learning model. Prognostic probability score may include any of the prognostic probability scores as described above in reference to FIG. 1. In an embodiment, prognostic label learner may rank plurality of prognostic outputs in descending order of probability. In an embodiment, prognostic label learner 112 and/or at least a server may select at least a prognostic output as a function of prognostic probability score. For example, prognostic label learner 112 and/or at least a server may select at least a prognostic output having the highest prognostic probability score. For example, prognostic label learner 112 may generate a plurality of prognostic outputs for at least a biological extraction such as a skin rash whereby a first prognostic output of hives may be associated with a prognostic probability score of 92%, a second prognostic output of dermatitis may be associated with a prognostic probability score of 12%, and a third prognostic output of Leprosy may be associated with a prognostic probability score of 0.5%. In such an instance, prognostic label learner 112 may select first prognostic output of hives containing the highest prognostic probability score to be included in at least a prognostic output and/or ameliorative output.

With continued reference to FIG. 10, prognostic label learner 112 may be configured to select a prognostic machine-learning process as a function of at least a biological extraction. Selecting a prognostic machine-learning process may include selecting a machine-learning model to generate a prognostic output and/or selecting an algorithm to generate a machine-learning model. Selecting a prognostic machine-learning process may be done utilizing any of the methodologies as described above in reference to FIG. 1.

Figure 11:
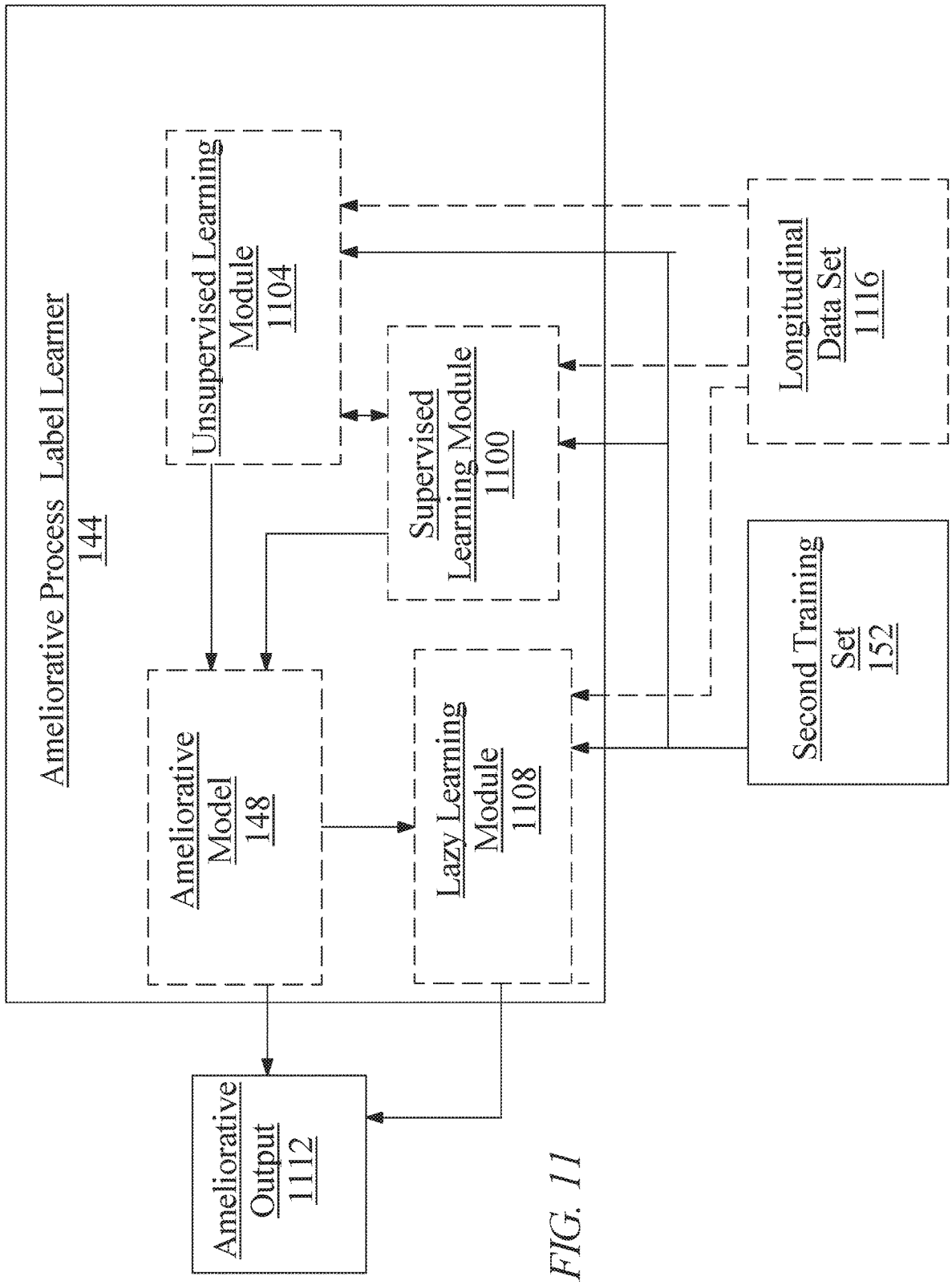
FIG. 11 is a block diagram illustrating an exemplary embodiment of an ameliorative process label learner.

Referring now to FIG. 11, an exemplary embodiment of ameliorative process label learner 144 is illustrated. Ameliorative process label learner 144 may be configured to perform one or more supervised learning processes, as described above; supervised learning processes may be performed by a supervised learning module 1100 executing on at least a server 104 and/or on another computing device in communication with at least a server 104, which may include any hardware or software module. For instance, a supervised learning algorithm may use prognostic labels as inputs, ameliorative labels as outputs, and a scoring function representing a desired form of relationship to be detected between prognostic labels and ameliorative labels; scoring function may, for instance, seek to maximize the probability that a given prognostic label and/or combination of prognostic labels is associated with a given ameliorative label and/or combination of ameliorative labels to minimize the probability that a given prognostic label and/or combination of prognostic labels is not associated with a given ameliorative label and/or combination of ameliorative labels. In an embodiment, one or more supervised machine-learning algorithms may be restricted to a particular domain; for instance, a supervised machine-learning process may be performed with respect to a given set of parameters and/or categories of prognostic labels that have been suspected to be related to a given set of ameliorative labels, for instance because the ameliorative processes corresponding to the set of ameliorative labels are hypothesized or suspected to have an ameliorative effect on conditions represented by the prognostic labels, and/or are specified as linked to a medical specialty and/or field of medicine covering a particular set of prognostic labels and/or ameliorative labels. As a non-limiting example, a particular set prognostic labels corresponding to a set of cardiovascular conditions may be typically treated by cardiologists, and a supervised machine-learning process may be performed to relate those prognostic labels to ameliorative labels associated with various treatment options, medications, and/or lifestyle changes.

With continued reference to FIG. 11, ameliorative process label learner 144 may perform one or more unsupervised machine-learning processes as described above; unsupervised processes may be performed by an unsupervised learning module 1104 executing on at least a server 104 and/or on another computing device in communication with at least a server 104, which may include any hardware or software module. For instance, and without limitation, ameliorative process label learner 144 and/or at least a server 104 may perform an unsupervised machine-learning process on second training set 152, which may cluster data of second training set 152 according to detected relationships between elements of the second training set 152, including without limitation correlations of prognostic labels to each other and correlations of ameliorative labels to each other; such relations may then be combined with supervised machine-learning results to add new criteria for ameliorative process label learner 144 to apply in relating prognostic labels to ameliorative labels. As a non-limiting, illustrative example, an unsupervised process may determine that a first prognostic label 128 correlates closely with a second prognostic label 156, where the first prognostic label 128 has been linked via supervised learning processes to a given ameliorative label, but the second has not; for instance, the second prognostic label 156 may not have been defined as an input for the supervised learning process, or may pertain to a domain outside of a domain limitation for the supervised learning process. Continuing the example, a close correlation between first prognostic label 128 and second prognostic label 156 may indicate that the second prognostic label 156 is also a good match for the ameliorative label; second prognostic label 156 may be included in a new supervised process to derive a relationship or may be used as a synonym or proxy for the first prognostic label 128 by ameliorative process label learner 144. Unsupervised processes performed by ameliorative process label learner 144 may be subjected to any domain limitations suitable for unsupervised processes performed by prognostic label learner 112 as described above.

Still referring to FIG. 11, at least a server 104 and/or ameliorative process label learner 144 may detect further significant categories of prognostic labels, relationships of such categories to ameliorative labels, and/or categories of ameliorative labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to at least a server 104, ameliorative process label learner 144 and/or at least a server 104 may continuously or iteratively perform unsupervised machine-learning processes to detect relationships between different elements of the added and/or overall data; in an embodiment, this may enable at least a server 104 to use detected relationships to discover new correlations between known biomarkers, prognostic labels, and/or ameliorative labels and one or more elements of data in large bodies of data, such as genomic, proteomic, and/or microbiome-related data, enabling future supervised learning and/or lazy learning processes to identify relationships between, e.g., particular clusters of genetic alleles and particular prognostic labels and/or suitable ameliorative labels. Use of unsupervised learning may greatly enhance the accuracy and detail with which system may detect prognostic labels and/or ameliorative labels.

Continuing to view FIG. 11, ameliorative process label learner 144 may be configured to perform a lazy learning process as a function of the second training set 152 and the at least a prognostic output to produce the at least an ameliorative output; a lazy learning process may include any lazy learning process as described above regarding prognostic label learner 112. Lazy learning processes may be performed by a lazy learning module 1108 executing on at least a server 104 and/or on another computing device in communication with at least a server 104, which may include any hardware or software module. Ameliorative output 1112 may be provided to a user client device 188 and/or an advisor client device 184 as described in further detail below.

In an embodiment, and still referring to FIG. 11, ameliorative process label learner 144 may generate a plurality of ameliorative labels having different implications for a particular person. For instance, where a prognostic label indicates that a person has a magnesium deficiency, various dietary choices may be generated as ameliorative labels associated with correcting the deficiency, such as ameliorative labels associated with consumption of almonds, spinach, and/or dark chocolate, as well as ameliorative labels associated with consumption of magnesium supplements. In such a situation, ameliorative process label learner 144 and/or at least a server 104 may perform additional processes to resolve ambiguity. Processes may include presenting multiple possible results to a medical practitioner, informing the medical practitioner of various options that may be available, and/or that follow-up tests, procedures, or counseling may be required to select an appropriate choice. Alternatively or additionally, processes may include additional machine-learning steps. For instance, ameliorative process label learner 144 may perform one or more lazy learning processes using a more comprehensive set of user data to identify a more probably correct result of the multiple results. Results may be presented and/or retained with rankings, for instance to advise a medical professional of the relative probabilities of various ameliorative labels being correct or ideal choices for a given person; alternatively or additionally, ameliorative labels associated with a probability of success or suitability below a given threshold and/or ameliorative labels contradicting results of the additional process, may be eliminated. As a non-limiting example, an additional process may reveal that a person is allergic to tree nuts, and consumption of almonds may be eliminated as an ameliorative label to be presented.

Continuing to refer to FIG. 11, ameliorative process label learner 144 may be designed and configured to generate further training data and/or to generate outputs using longitudinal data 1116. As used herein, longitudinal data 1116 may include a temporally ordered series of data concerning the same person, or the same cohort of persons; for instance, longitudinal data 1116 may describe a series of blood samples taken one day or one month apart over the course of a year. Longitudinal data 1116 may related to a series of samples tracking response of one or more elements of physiological data recorded regarding a person undergoing one or more ameliorative processes linked to one or more ameliorative process labels. Ameliorative process label learner 144 may track one or more elements of physiological data and fit, for instance, a linear, polynomial, and/or splined function to data points; linear, polynomial, or other regression across larger sets of longitudinal data, using, for instance, any regression process as described above, may be used to determine a best-fit graph or function for the effect of a given ameliorative process over time on a physiological parameter. Functions may be compared to each other to rank ameliorative processes; for instance, an ameliorative process associated with a steeper slope in curve representing improvement in a physiological data element, and/or a shallower slope in a curve representing a slower decline, may be ranked higher than an ameliorative process associated with a less steep slope for an improvement curve or a steeper slope for a curve marking a decline. Ameliorative processes associated with a curve and/or terminal data point representing a value that does not associate with a previously detected prognostic label may be ranked higher than one that is not so associated. Information obtained by analysis of longitudinal data 1116 may be added to ameliorative process database and/or second training set.

With continued reference to FIG. 11, ameliorative process label learner 144 may be configured to generate a plurality of ameliorative outputs each containing a prognostic improvement score correlated to at least a prognostic output as a function of the at least a prognostic output, at least a second training set, and at least an ameliorative machine-learning model. Prognostic improvement score includes any of the prognostic improvement scores as described above in reference to FIG. 1. In an embodiment, ameliorative process label learner 144 may rank plurality of ameliorative outputs in descending order. For instance and without limitation, ameliorative process label learner 144 may generate a plurality of ameliorative outputs for a prognostic output such as hypertension which may include a first ameliorative output such as a ubiquinol supplement containing a 67% prognostic improvement score, a second ameliorative output such as a high blood pressure medication containing a 28% prognostic improvement score, and a third ameliorative output such as a yoga meditation sequence containing a 12% prognostic improvement score. In an embodiment, ameliorative process label learner 144 may select at least an ameliorative process label containing the highest prognostic improvement score.

With continued reference to FIG. 11, ameliorative process label learner 144 may be configured to select an ameliorative machine-learning process as a function of a prognostic label. This may include for example selecting a machine-learning model and/or selecting an algorithm to generate a machine-learning model. This may be done utilizing any of the methodologies as described above in reference to FIG. 1.

Figure 12:
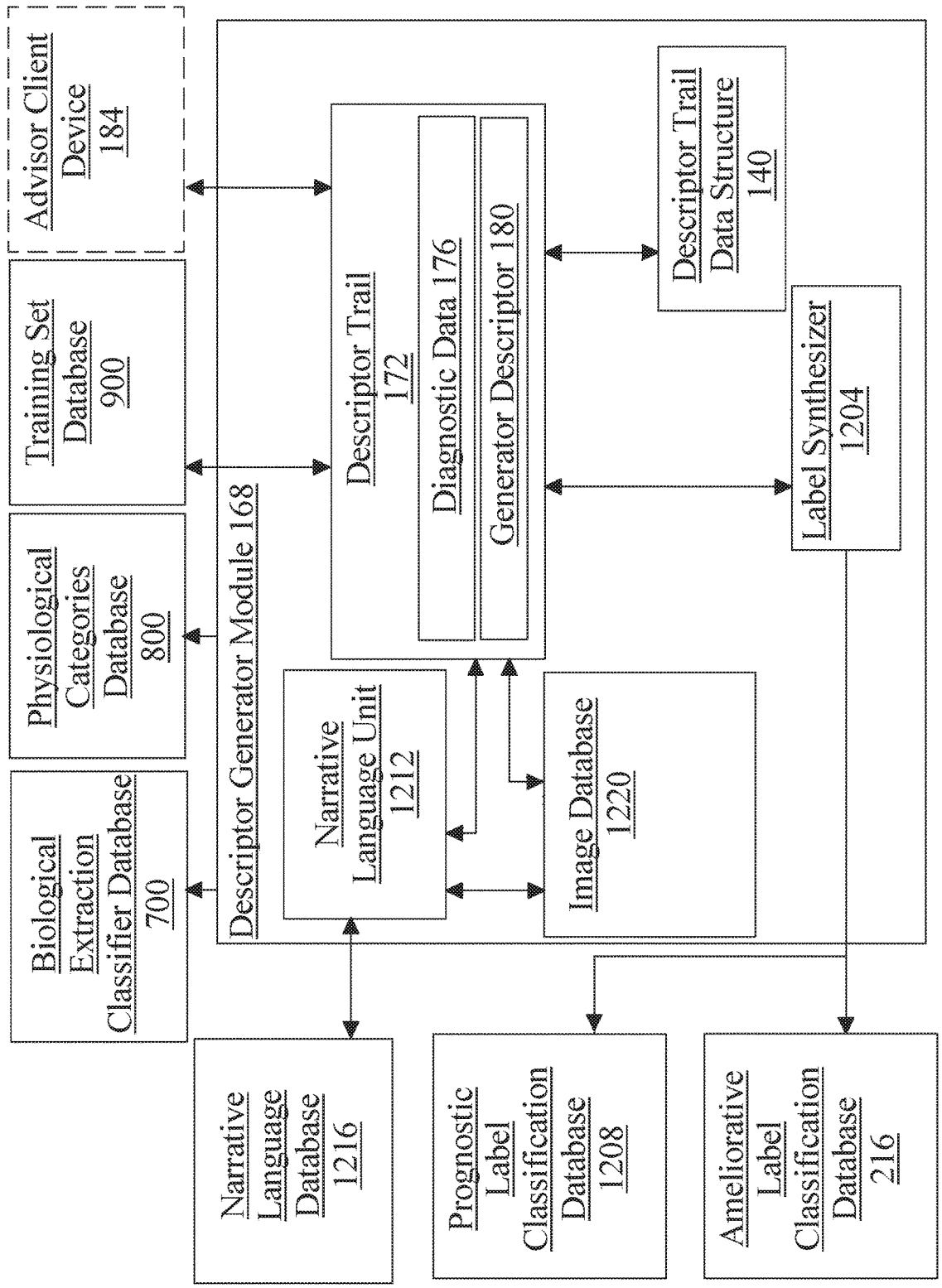
FIG. 12 is a block diagram illustrating an exemplary embodiment of a descriptor generator module.

Referring now to FIG. 12, an exemplary embodiment of descriptor generator module 168 is illustrated. Descriptor generator module 168 generates at least a descriptor trail 172 wherein the at least a descriptor trail 172 includes at least an element of diagnostic data 176. Descriptor trail 172 includes any data and/or data element describing generation and/or selection of at least a prognostic output and/or ameliorative output including at least a prognostic output and at least a correlated ameliorative output. Diagnostic data 176, includes any data and/or data element used to generate a prognostic output and/or ameliorative output. Diagnostic data 176 may include at least a biological extraction, biological extraction classifier label, training data, a first training set, a second training set, a prognostic output, an ameliorative output, a prognostic output and/or ameliorative output, any machine-learning model utilized to generate a prognostic output and/or ameliorative output, a plurality of prognostic outputs, a plurality of ameliorative outputs, any regression models, weighted variables, confidence levels, error functions, datasets, models, and/or calculations utilized to generate a prognostic output and/or ameliorative output as described above in more detail in reference to FIG. 1.

With continued reference to FIG. 12, descriptor generator module 168 may include a label synthesizer 1204. In an embodiment, label synthesizer 1204 may be designed and configured to combine a plurality of labels in at least a prognostic output together to provide maximally efficient data presentation. Combination of labels together may include elimination of duplicate information. For instance, label synthesizer 1204 and/or at least a server 104 may be designed and configured to determine a first prognostic label 128 of the at least a prognostic label is a duplicate of a second prognostic label 156 of the at least a prognostic label and eliminate the first prognostic label. Determination that a first prognostic label 128 is a duplicate of a second prognostic label 156 may include determining that the first prognostic label 128 is identical to the second prognostic label; for instance, a prognostic label generated from test data presented in one biological extraction of at least a biological extraction may be the same as a prognostic label generated from test data presented in a second biological extraction of at least a biological extraction. As a further non-limiting example, a first prognostic label 128 may be synonymous with a second prognostic label, where detection of synonymous labels may be performed, without limitation, by a language processing module 136 as described above.

Continuing to refer to FIG. 12, label synthesizer 1204 may group prognostic labels according to one or more classification systems relating the prognostic labels to each other. For instance, descriptor generator module 168 and/or label synthesizer 1204 may be configured to determine that a first prognostic label 128 of the at least a prognostic label and a second prognostic label 156 of the at least a prognostic label belong to a shared category. A shared category may be a category of conditions or tendencies toward a future condition to which each of first prognostic label 128 and second prognostic label 156 belongs; as an example, lactose intolerance and gluten sensitivity may each be examples of digestive sensitivity, for instance, which may in turn share a category with food sensitivities, food allergies, digestive disorders such as celiac disease and diverticulitis, or the like. Shared category and/or categories may be associated with prognostic labels as well. A given prognostic label may belong to a plurality of overlapping categories. Descriptor generator module 168 may be configured to add a category label associated with a shared category to prognostic output and/or ameliorative output, where addition of the label may include addition of the label and/or a datum linked to the label, such as a textual or narrative description. In an embodiment, relationships between prognostic labels and categories may be retrieved from a prognostic label classification database 1208, for instance by generating a query using one or more prognostic labels of at least a prognostic output, entering the query, and receiving one or more categories matching the query from the prognostic label classification database 1208.

With continued reference to FIG. 12, descriptor generator module 168 may be configured to generate descriptor trail 172 by converting one or more elements of diagnostic data 176 into narrative language. As a non-limiting example, descriptor generator module 168 may include a narrative language unit 1212, which may be configured to determine an element of narrative language associated with at least an element of diagnostic data 176 and include the element of narrative language in descriptor trail 172. Narrative language unit 1212 may implement this, without limitation, by using language processing module 136 to detect one or more associations between diagnostic data 176, lists of diagnostic data 176, and/or statements of narrative language. In an embodiment, descriptor generator module 168 may convert one or more elements of diagnostic data 176 into narrative language such as for example, a first training set, a plurality of prognostic outputs, at least an ameliorative output, a confidence level calculation and the like. Alternatively or additionally, narrative language unit 1212 may retrieve one or more elements of narrative language from a narrative language database 1216, which may contain one or more tables associating diagnostic data 176 and/or groups of diagnostic data 176 with words, sentences, and/or phrases of narrative language. One or more elements of narrative language may be included in descriptor trail 172, for instance to display to an informed advisor as text describing an element of training data that was selected to generate a prognostic output. Descriptor trail 172 may include one or more images, one or more images may be retrieved by descriptor generator module 168 from an image database, which may contain one or more tables associating diagnostic data 176, groups of diagnostic data 176, or the like with one or more images. For example, descriptor trail 172 may include a biological extraction that includes an x-ray image or a prognostic output and/or ameliorative output that includes a prognostic output that includes a magnetic resonance image (MRI).

With continued reference to FIG. 12, label synthesizer 1204 may group ameliorative labels according to one or more classification systems relating the ameliorative labels to each other. For instance, label synthesizer 1104 may be configured to determine that a first ameliorative label of the at least an ameliorative label and a second ameliorative label of the at least an ameliorative label belong to a shared category. A shared category may be a category of conditions or tendencies toward a future condition to which each of first ameliorative label and second ameliorative label belongs; as an example, lactose intolerance and gluten sensitivity may each be examples of digestive sensitivity, for instance, which may in turn share a category with food sensitivities, food allergies, digestive disorders such as celiac disease and diverticulitis or the like. In an embodiment, a first ameliorative label such as a yoga sequence and a second ameliorative label such as a cardiovascular exercise routine may each relate to a shared category such as fitness. In yet another non-limiting example, a first ameliorative label such as a prescription medication and a second ameliorative label such as an oral supplement may each relate to a shared category such as oral therapies. Categories of ameliorative labels and relationships between ameliorative labels may be retrieved from ameliorative label classification database 216 as described above in more detail in reference to FIG. 6. In an embodiment, descriptor generator module 168 may retrieve a category from ameliorative label classification database 216 by generating a query using one or more ameliorative labels generated by ameliorative label learner 160 and matching the query from the ameliorative label classification database 216.

With continued reference to FIG. 12, descriptor generator module 168 generate at least a descriptor trail 172 containing at least an element of diagnostic data 176 by extracting at least an element of diagnostic data 176 from descriptor trail data structure 140. Descriptor trail data structure 140 may contain one or more tables each containing different elements of diagnostic data 176 as described in more detail below. Descriptor generator module 168 may consult biological extraction classifier database 700, physiological categories database 800, and/or training set database 900 to select other elements of diagnostic data 176. In an embodiment, descriptor generator module 168 may retrieve at least an element of diagnostic data 176 from a database such as descriptor trail data structure 140 or physiological categories database by generating a query using one or more elements of prognostic output and/or ameliorative output and matching the query to at least a data entry contained within a database. Descriptor generator module 168 may be in communication with advisor client device 184 to receive at least an advisor filter input containing at least a diagnostic data 176 selection and generate at least a descriptor trail 172 as a function of the at least an advisor filter. In an embodiment, at least an advisor filter may be utilized to select at least an element of diagnostic data 176 from a database. Descriptor generator module 168 may be configured to transmit at least a descriptor trail 172 to at least an advisor client device 184. This may be performed utilizing any network methodology as described herein.

Figure 13:
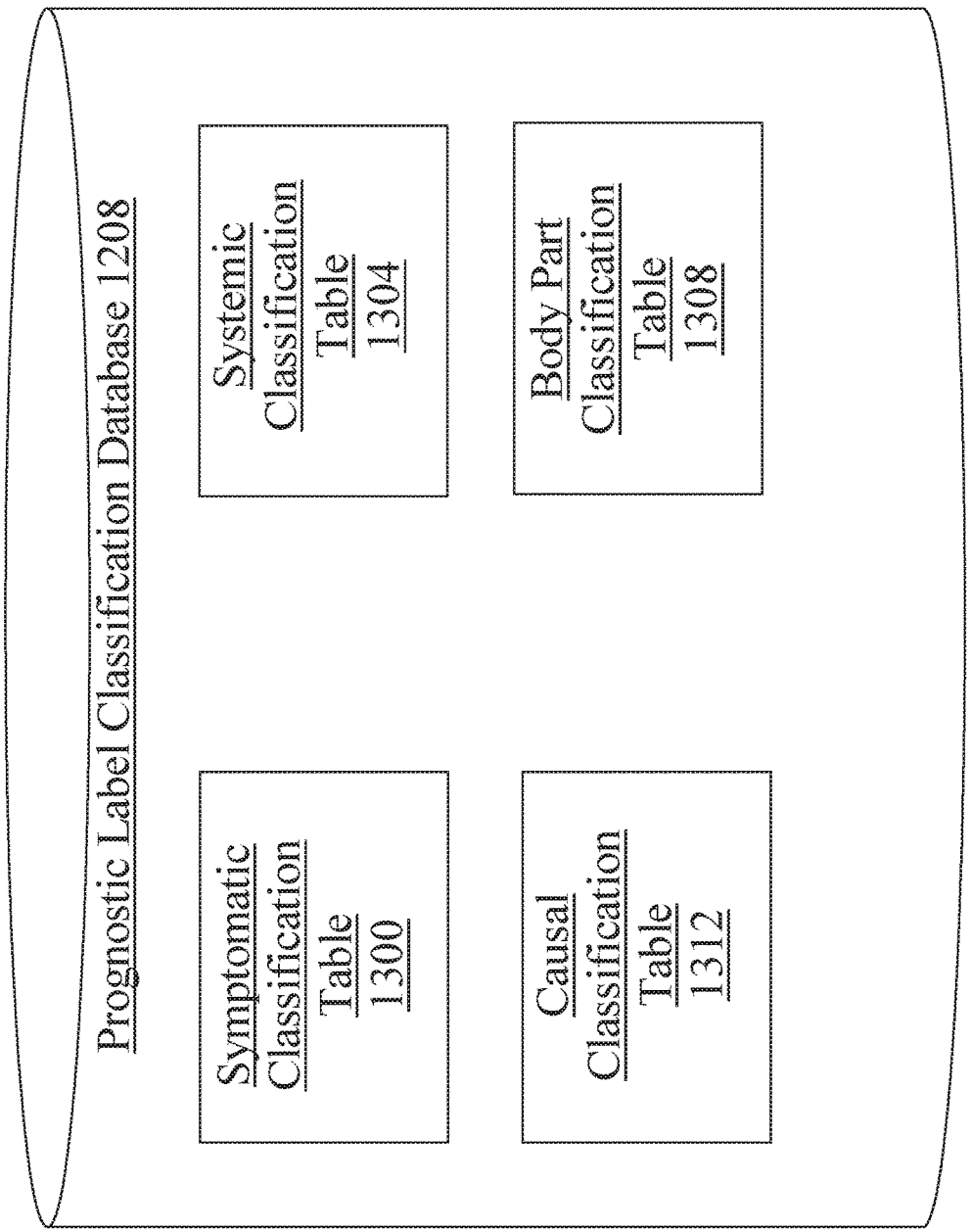
FIG. 13 is a block diagram illustrating an exemplary embodiment of a prognostic label classification database.

Referring now to FIG. 13, an exemplary embodiment of a prognostic label classification database 1208 is illustrated. Prognostic label classification database 1208 may be implemented as any database and/or datastore suitable for use as biological extraction database 200 as described above. One or more database tables in prognostic label classification database 1208 may include, without limitation, a symptomatic classification table 1300; symptomatic classification table 1300 may relate each prognostic label to one or more categories of symptoms associated with that prognostic label. As a non-limiting example, symptomatic classification table 1300 may include records indicating that each of lactose intolerance and gluten sensitivity results in symptoms including gas buildup, bloating, and abdominal pain. One or more database tables in prognostic label classification database 1208 may include, without limitation, a systemic classification table 1304; systemic classification table 1304 may relate each prognostic label to one or more systems associated with that prognostic label. As a non-limiting example, systemic classification table 1304 may include records indicating each of lactose intolerance and gluten sensitivity affects the digestive system; two digestive sensitivities linked to allergic or other immune responses may additionally be linked in systemic classification table 1304 to the immune system. One or more database tables in prognostic label classification database 1208 may include, without limitation, a body part classification table 1308; body part classification table 1308 may relate each prognostic label to one or more body parts associated with that prognostic label. As a non-limiting example, body part classification table 1308 may include records indicating each of psoriasis and rosacea affects the skin of a person. One or more database tables in prognostic label classification database 1208 may include, without limitation, a causal classification table 1312; causal classification table 1312 may relate each prognostic label to one or more causes associated with that prognostic label. As a non-limiting example, causal classification table 1312 may include records indicating each of type 2 diabetes and hypertension may have obesity as a cause. The above-described tables, and entries therein, are provided solely for exemplary purposes. Persons skilled in the art, upon reviewing the entirety of this disclosure, will be aware of various additional examples for tables and/or relationships that may be included or recorded in prognostic classification table consistently with this disclosure.

Figure 14:
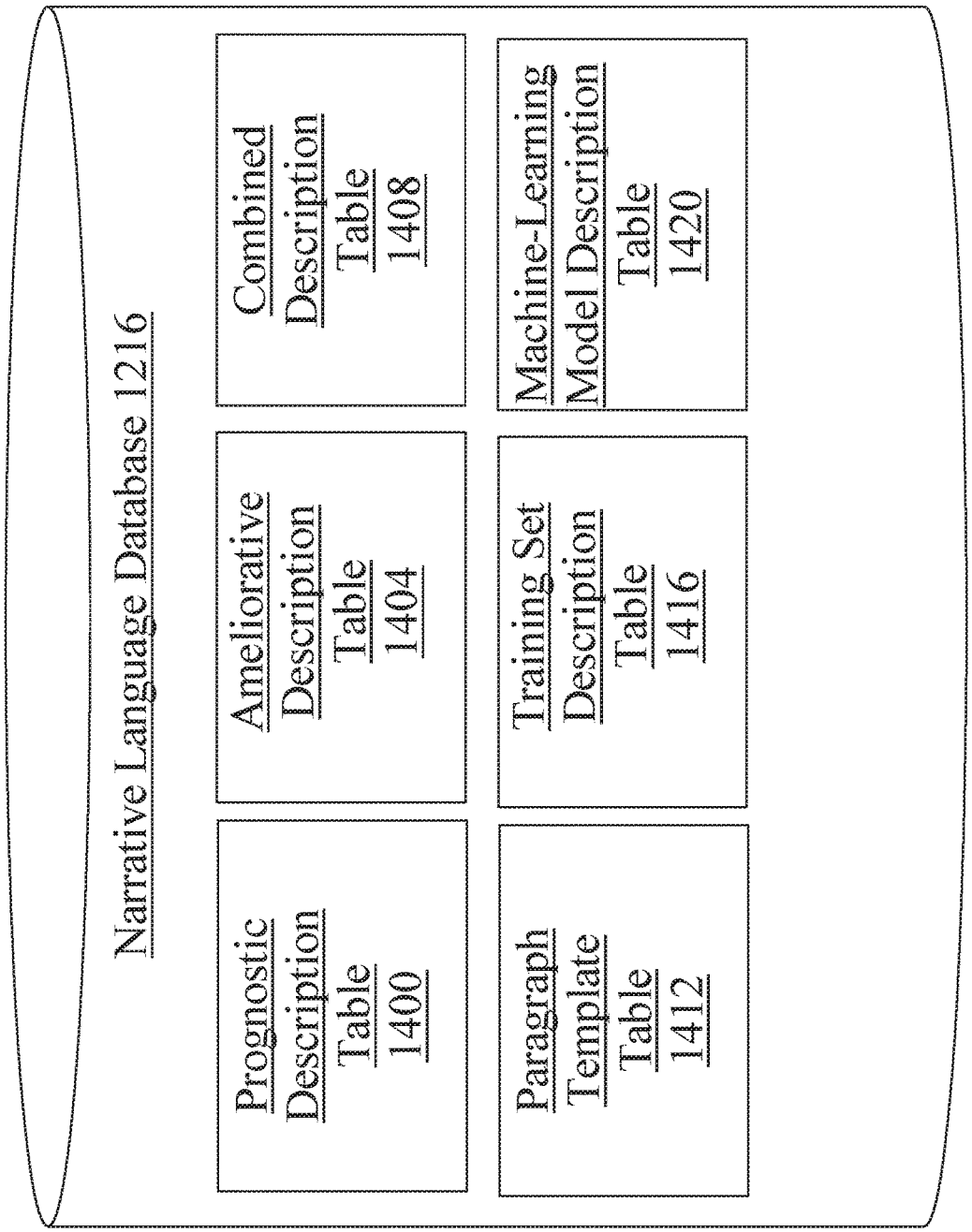
FIG. 14 is a block diagram illustrating an exemplary embodiment of a narrative language database.

Referring now to FIG. 14, and exemplary embodiment of a narrative language database 1216 is illustrated. Narrative language database 1216 may be implemented as any database and/or datastore suitable for use as biological extraction database 200 as described above. One or more database tables in narrative language database 1216 may include, without limitation, a prognostic description table 1400, which may link prognostic labels to narrative descriptions associated with prognostic labels. One or more database tables in narrative language database 1216 may include, without limitation, an ameliorative description table 1404, which may link ameliorative process labels to narrative descriptions associated with ameliorative process labels. One or more database tables in narrative language database 1216 may include, without limitation, a combined description table 1408, which may link combinations of prognostic labels and ameliorative labels to narrative descriptions associated with the combinations. One or more database tables in narrative language database 1216 may include, without limitation, a paragraph template table 1412, which may contain one or more templates of paragraphs, pages, reports, or the like into which images and text, such as images obtained from image database 1220 and text obtained from prognostic description table 1400, ameliorative description table 1404, and combined description table 1408 may be inserted. One or more database tables in narrative language database 1216 may include, without limitation, training set description table 1416, which may link training sets to narrative descriptions associated with training sets, such as physiological state data 124 used in a training set. One or more database tables in narrative language database 1216 may include, without limitation, machine-learning model description table 1420, which may link machine-learning models to narrative descriptions associated with machine-learning models, such as narrative language describing a particular hierarchical clustering model generated or a supervised machine-learning model that is generated. Other tables not illustrated in narrative language database 1216 may include for example biological extraction description table, a physiological state data description table, a prognostic output and/or ameliorative output table, and the like. Tables in narrative language database 1216 may be populated, as a non-limiting example, using submissions from experts, which may be collected according to any processes described above. Persons skilled in the art, upon reviewing the entirety of this disclosure, will be aware of various ways in which entries in narrative language database 1216 may be categorized and/or organized.

Figure 15:
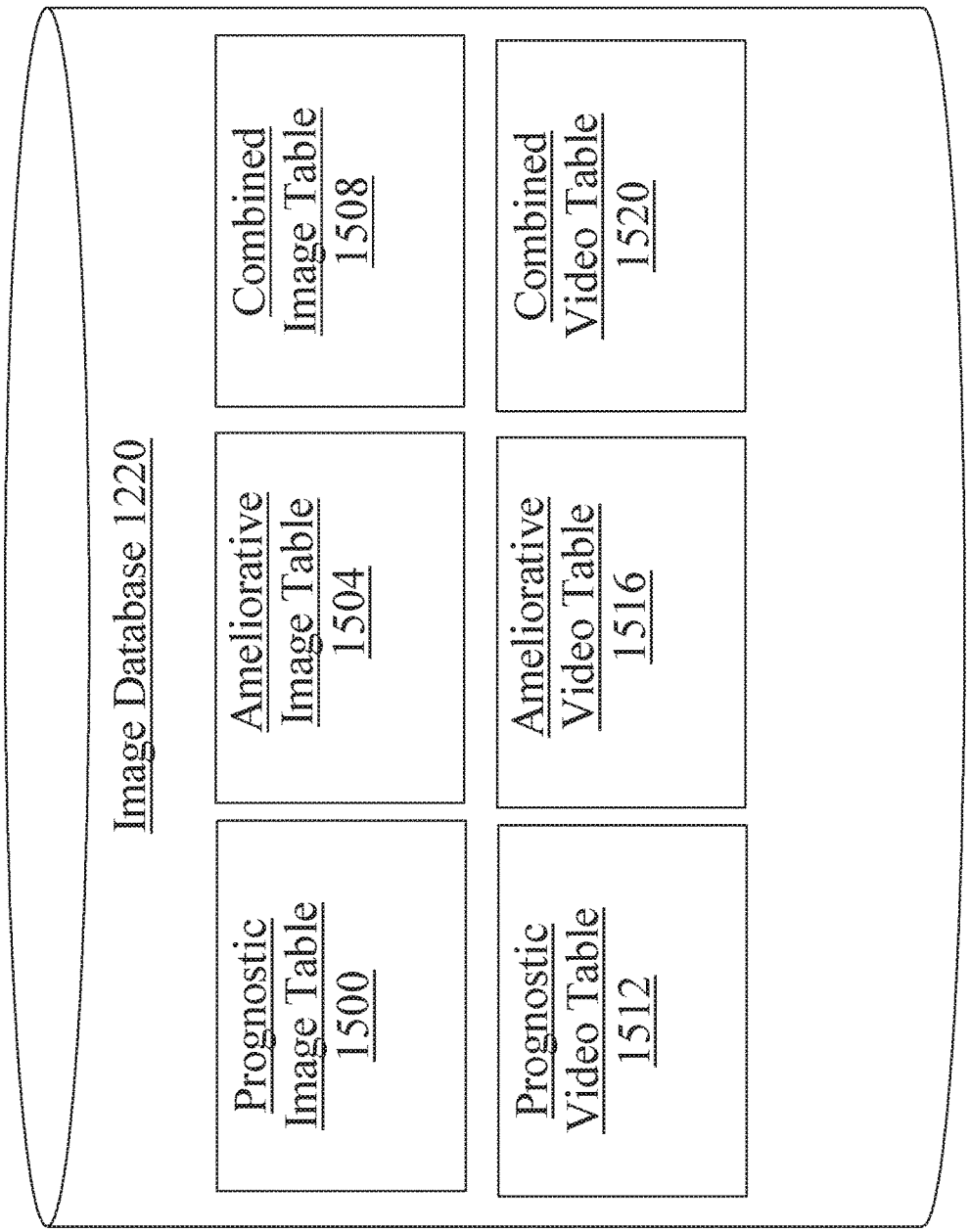
FIG. 15 is a block diagram illustrating an exemplary embodiment of an image database.

Referring now to FIG. 15, an exemplary embodiment of an image database 1220 is illustrated. Image database 1220 may be implemented as any database and/or datastore suitable for use as biological extraction database 200 as described above. One or more database tables in image database 1220 may include, without limitation, a prognostic image table 1500, which may link prognostic labels to images associated with prognostic labels. One or more database tables in image database 1220 may include, without limitation, an ameliorative image table 1504, which may link ameliorative process labels to images associated with ameliorative process labels. One or more database tables in image database 1220 may include, without limitation, a combined description table 1508, which may link combinations of prognostic labels and ameliorative labels to images associated with the combinations. One or more database tables in image database 102 may include, without limitation, a prognostic video table 1512, which may link prognostic labels to videos associated with prognostic labels. One or more database tables in image database 1220 may include, without limitation, an ameliorative video table 1516, which may link ameliorative process labels to videos associated with ameliorative process labels. One or more database tables in image database 1220 may include, without limitation, a combined video table 1520, which may link combinations of prognostic labels and ameliorative labels to videos associated with the combinations. Other tables contained within image database 1220 and not illustrated may include for example biological extraction image table, machine-learning model image table, physiological state data 124 image table, a prognostic output and/or ameliorative output image table, and the like. Tables in image database 1220 may be populated, without limitation, by submissions by experts, which may be provided according to any process or process steps described in this disclosure for collection of expert submissions.

Figure 16:
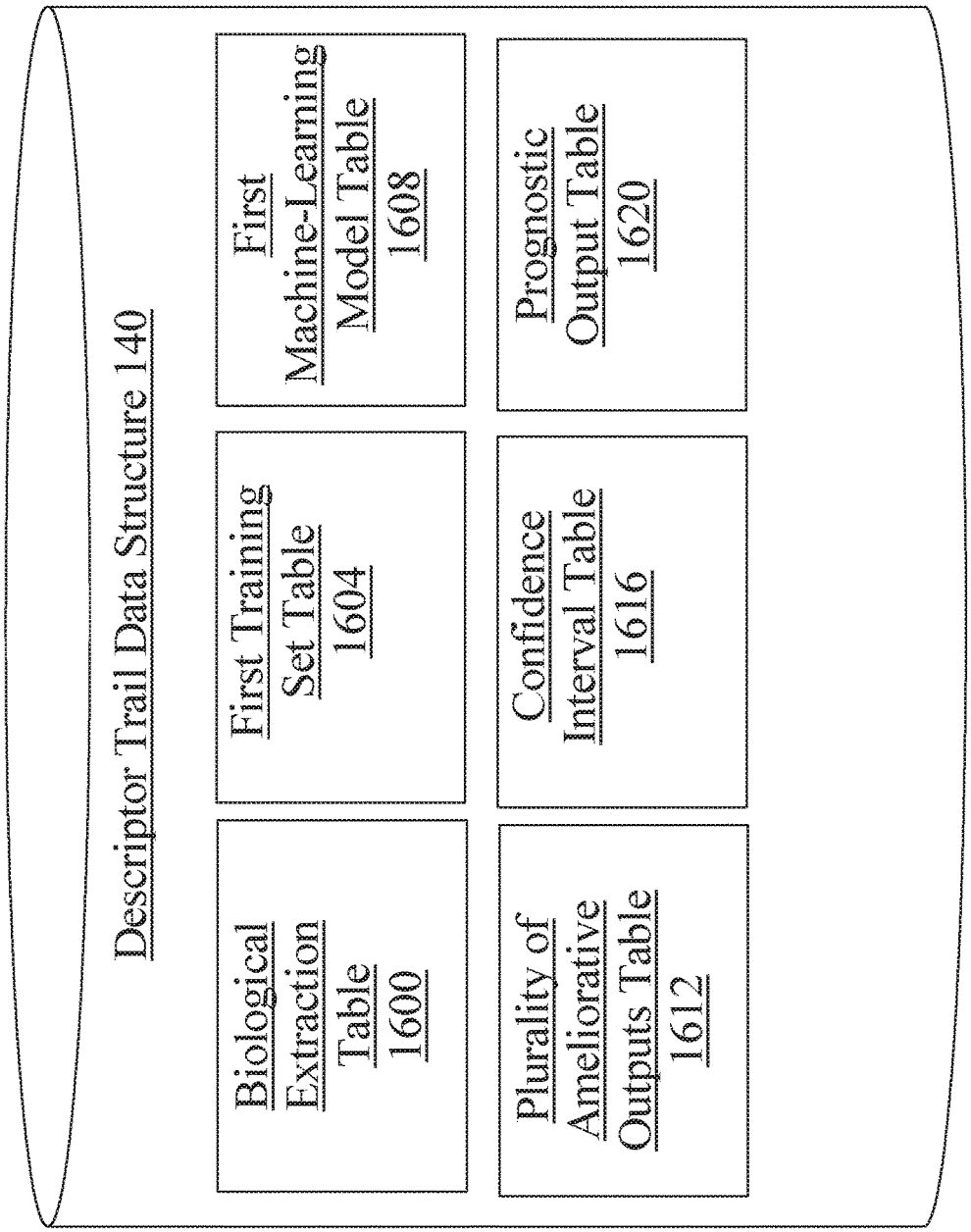
FIG. 16 is a block diagram illustrating an exemplary embodiment of a descriptor trail data structure.

Referring now to FIG. 16, an exemplary embodiment of descriptor trail data structure 140 is illustrated. Descriptor trail data structure 140 may be implemented as any database and/or datastore suitable use as biological extraction database 200 as described above. One or more database tables in descriptor trail data structure 140 may include, without limitation, biological extraction table 1600, which may include any biological extraction utilized to generate at least a prognostic output and/or ameliorative output. One or more database tables in descriptor trail data structure 140 may include, without limitation, first training set table 1604, which may include any first training set 120 utilized to generate at least a prognostic output and/or ameliorative output. One or more database tables in descriptor trail data structure 140 may include, without limitation, prognostic machine-learning model table 1608, which may include any prognostic machine-learning model utilized to generate at least a prognostic output and/or ameliorative output. One or more database tables in descriptor trail data structure 140 may include, without limitation, plurality of ameliorative outputs table 1612, which may include any plurality of ameliorative outputs generated by ameliorative label learner 160. One or more database tables in descriptor trail data structure 140 may include, without limitation, confidence interval table 1616, which may include any confidence level calculated and/or utilized to generate at least a prognostic output and/or ameliorative output. One or more database tables in descriptor trail data structure 140 may include, without limitation, prognostic output table 1620, which may include at least a prognostic output which may be included in prognostic output and/or ameliorative output and/or selected from a plurality of prognostic outputs generated by prognostic label learner 112. Tables in descriptor trail data structure 140 may be populated, without limitation, by submissions by at least a server 104, which may be designed and configured to record at least an element of diagnostic data 176.

Figure 17:
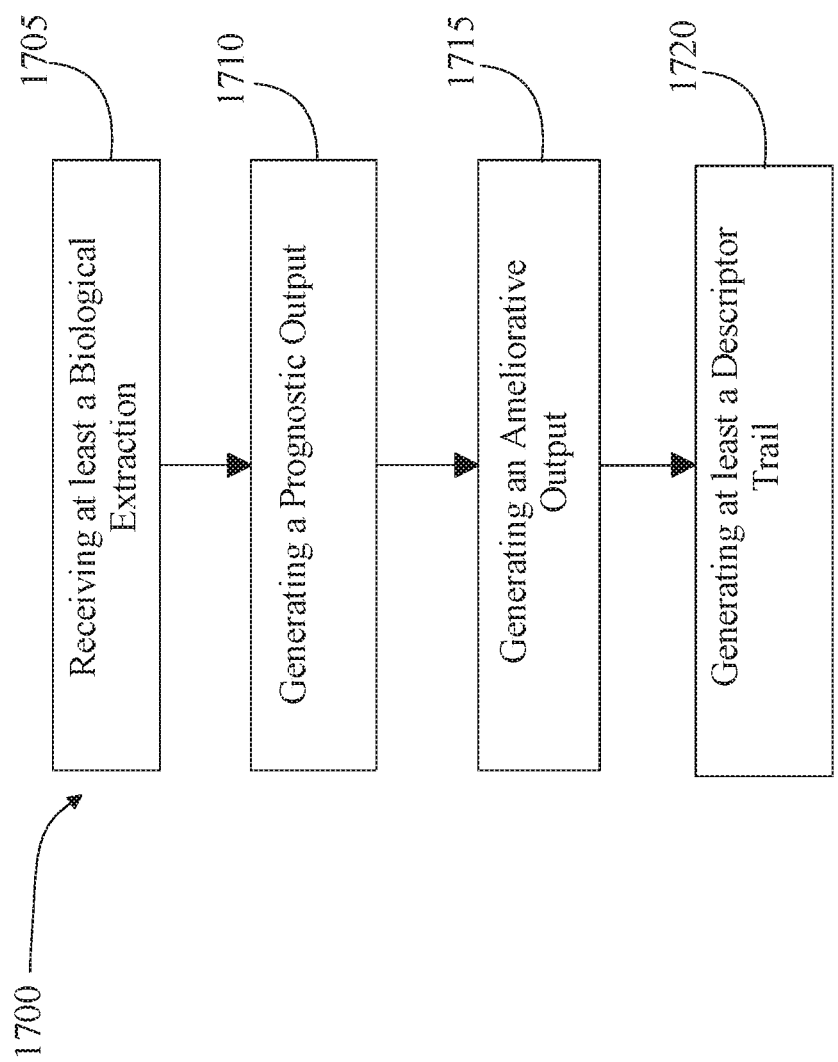
FIG. 17 is a process flow diagram illustrating an exemplary embodiment of a method for generating a descriptor trail using artificial intelligence.

Referring now to FIG. 17, an exemplary embodiment of a method 1700 of generating a descriptor trail 172 using artificial intelligence is illustrated. At step 1705 at least a server receives at least a biological extraction. Biological extraction includes any of the biological extractions as described herein. At least a biological extraction may be received utilizing any methodology as described herein. In an embodiment, at least a server 104 may be configured to receive at least a biological extraction wherein the at least a biological extraction further comprises at least a fluid sample and classify the at least a biological extraction. Classifying the at least a biological extraction may include comparing the at least a biological extraction to at least a biological standard level and generating at least a biological extraction classifier label. Biological standard level may include any of the biological standard levels as described above in reference to FIG. 1. And FIG. 7. Biological standard levels may be contained within biological extraction classifier label database 700 as described above in more detail in reference to FIG. 7. For example, at least a biological extraction such as a salivary estrone level may be compared to a biological standard level contained within biological extraction classifier label database 700 and categorized as "normal" when salivary estrone level falls within standard level range. At least a biological extraction may be categorized according to any biological extraction classification scheme, including any of the biological extraction classifying schemes as described above in reference to FIG. 7. In an embodiment, at least a biological extraction may receive a plurality of biological extraction classifiers. For instance and without limitation, at least a biological extraction such as a blood serum sample containing a troponin level of 0.5 nanograms per milliliter (ng/ml) as compared to a standard level retrieved from biological extraction classifier label database 700 of 0 to 0.004 nanograms per milliliter (ng/ml) may receive biological extraction classifier label of "elevated label," "abnormal findings label," and "MD alert table" as any troponin level above 0.40 nanograms per milliliter (ng/ml) may be indicative of a myocardial infarction or heart attack. Generating at least a biological extraction classifier label may include matching a biological extraction with at least a category of physiological state data 124 received from at least an expert. In an embodiment, categories of physiological state data 124 may be contained within physiological categories database 800. Matching at least a biological extraction to at least a physiological category received from at least an expert may include generating at least a query and matching the at least a query to an entry contained within physiological categories database 800. For instance and without limitation, generating at least a biological extraction classifier label may include matching at least a biological extraction such as a saliva sample containing a progesterone reading to a physiological category contained within physiological categories database 800 such as endocrine table 824. In yet another non-limiting example, generating at least a biological extraction classifier label may include matching at least a biological extraction such as a stool sample containing a gut species analysis of bacteria may be matched to a physiological category contained within physiological categories database 800 such as digestive table 808.

With continued reference to FIG. 17, at step 1710 at least a server 104 generates a prognostic output as a function of at least a biological extraction. Generating prognostic output includes selecting a prognostic machine-learning process as a function of at least a biological extraction, recording the selected prognostic machine-learning process in a descriptor trail data structure, and generating the prognostic output using the selected prognostic machine-learning process as a function of the at least a biological extraction. Selecting a prognostic machine-learning process may include for example selecting a training set, selecting a machine-learning algorithm, and/or selecting a machine-learning model.

With continued reference to FIG. 17, at step 1710 at least a server 104 selects training data. Selecting training data may including selecting at least a first training set 120 wherein the at least a first training set 120 includes a plurality of first data entries, each first data entry of the first training set 120 including at least an element of physiological state data 124 and at least a correlated first prognostic label. Physiological state data 124 may include any of the physiological state data 124 as described above in reference to FIGS. 1-17. First prognostic label 128 may include any of the first prognostic labels as described above in reference to FIGS. 1-17. In an embodiment, at least a server 104 may select at least at least a first training set 120 as a function of the at least a biological extraction classifier label. For example, at least a biological extraction classifier label that is marked as "low" may be utilized to select at least a first training set 120 that includes a plurality of first data entries where at least a first data entry includes at least an element of physiological data that includes an element of "low" physiological data and at least a correlated first prognostic label. In yet another non-limiting example, at least a biological extraction such as a blood sample containing a fasting blood sugar level of 160 milligrams per deciliter (mg/dL) may contain a biological extraction classifier label marked as "elevated." In such an instance, biological extraction classifier label of "elevated" may be utilized to select at least a first training set 120 that includes a plurality of first data entries where at least a data entries includes at least an element of physiological data such as a fasting blood glucose level of 185 milligrams per deciliter (mg/dL) and correlated to at least a first prognostic label 128 such as pre-diabetes. In an embodiment, at least a first training set 120 may be selected from training set database 900. At least a server 104 may select at least a first training set 120 as a function of the at least a physically extracted sample contained within the at least a biological extraction. For example, at least a server 104 may determine category of physically extracted sample contained within at least a biological extraction such as a blood sample, a stool sample, a cerebrospinal fluid sample, and the like and match the physically extracted sample to a category of training data organized by sample type contained within training set database 900. For instance and without limitation, at least a biological extraction such as a stool sample may be matched to a training set contained with digestive stool sample table 908. In yet another non-limiting example, at least a biological extraction such as a cerebrospinal fluid sample may be matched to at least a first training set 120 contained within neurological cerebrospinal fluid table 916.

With continued reference to FIG. 17, generating at least a prognostic output may include creating at least a prognostic machine-learning model relating physiological state data 124 to prognostic labels using at least a first training set 120 and generating the at least a prognostic output using the at least a biological extraction, the at least a first training set, and the at least a prognostic machine-learning model. At least a prognostic output may be generated by prognostic label learner 112. Prognostic machine-learning model includes any of the machine-learning models as described above in reference to FIGS. 1-17. Prognostic label learner 112 may include supervised learning module, unsupervised learning module, and/or lazy learning module as described above in more detail in reference to FIG. 10. Selecting a prognostic machine-learning model may include selecting any of the machine-learning models as described above in reference to FIG. 10. Prognostic label learner 112 may generate a plurality of prognostic outputs each containing a ranked prognostic probability score as a function of at least a biological extraction, at least a first training set, and at least a prognostic machine-learning model. Prognostic probability score may indicate a likelihood of a particular prognostic output associated with at least a biological extraction as described above in more detail in reference to FIG. 1. In an embodiment, at least a prognostic output selected to be included in at least a prognostic output and/or ameliorative output may contained the highest prognostic probability score indicating the highest likelihood of a particular biological extraction being associated with a particular prognosis. Prognostic label learner 112 may rank prognostic outputs whereby a plurality of prognostic outputs may be generated and listed in decreasing order of probability. For example, prognostic label learner 112 may generate a plurality of prognostic output and/or ameliorative output for at least a biological extraction such as a fever whereby a first prognostic output of flu may be associated with a prognostic probability score of 85%, a second prognostic output of ear infection may be associated with a prognostic probability score of 22%, and a third prognostic output of sepsis may be associated with a prognostic probability score of 1%. In such an instance, prognostic label learner 112 may select first prognostic output of flu containing the highest prognostic probability score to be included in at least a prognostic output and/or ameliorative output.

With continued reference to FIG. 17, at step 1715 at least a server generates an ameliorative output as a function of a prognostic output. Generating an ameliorative output includes selecting an ameliorative machine-learning process as a function of the prognostic label, recording the selected ameliorative machine-learning process in the descriptor trail data structure, and generating the ameliorative output using the selected ameliorative machine-learning process as a function of the prognostic output. Selecting a prognostic machine-learning process may include selecting a training data set, selecting a machine-learning algorithm, and/or selecting a machine-learning model.

With continued reference to FIG. 17, at least a server 104 and/or ameliorative label learner may select at least a second training set 152 as a function of the at least a first training set. At least a second training set 152 includes a plurality of second data entries, each second data entry of the second training set 152 including at least a second prognostic label 156 and at least a correlated ameliorative process label. At least a second training set 152 may be selected as a function of the at least a first training set 120 as a function of a dependency relationship between the two training sets. In an embodiment, at least a first training set 120 may be correlated to at least a second training set 152 whereby first prognostic label 128 is utilized as second prognostic label 156 to generate ameliorative process label 160. In an embodiment, at least a first training set 120 may be stored with at least a second training set 152 together in training set database 900 so that selecting at least a first training set 120 automatically triggers selection of second training set 152 correlated and stored with the first training set 120 in training set database 900. Training set selection may be recorded by at least a server in descriptor trail data structure.

With continued reference to FIG. 17, generating at least an ameliorative output may include creating at least an ameliorative machine-learning model relating prognostic labels to ameliorative labels using at least a second training set 152 and generating the at least an ameliorative output using the at least a second training set 152 and the at least a biological extraction. Ameliorative output may be generated by ameliorative label learner 160. Ameliorative machine-learning model includes any of the machine-learning models as described above in reference to FIGS. 1-17. Ameliorative label learner 160 may include supervised learning module, unsupervised learning module, and/or lazy learning module as described above in more detail in reference to FIG. 11. Ameliorative label learner may be configured to generate a plurality of ameliorative outputs each containing a prognostic improvement score correlated to at least a prognostic output as a function of the at least a prognostic output, at least a second training set 152 and at least an ameliorative machine-learning model. Prognostic improvement score indicates a likelihood of a particular ameliorative output treating, preventing, and/or reversing a given prognostic output. For example, ameliorative label learner 160 may generate a plurality of ameliorative outputs for a prognostic output such as hypercholesteremia which may include a first ameliorative output such as a statin medication containing a 52% prognostic improvement score, a second ameliorative output such as red rice yeast extract containing a 48% prognostic improvement score, and a third ameliorative output such as cardiovascular exercise three days each week containing a 22% prognostic improvement score. In an embodiment, ameliorative label learner 160 may rank ameliorative outputs in decreasing order of prognostic improvement scores and ameliorative label learner 160 may select at least an ameliorative process label 160 from plurality of ameliorative process labels to be included in prognostic output and/or ameliorative output. In an embodiment, ameliorative label learner 160 may select an ameliorative output from plurality of ameliorative outputs containing the highest prognostic improvement score.

With continued reference to FIG. 17, at least a sever 104 may record at least an element of diagnostic data 176. Diagnostic data 176 may include any of the diagnostic data 176 as described above in reference to FIGS. 1-17. For example, at least a server 104 may record in memory for example at least a first training set 120 utilized to generate at least a prognostic output contained within a prognostic output and/or ameliorative output. In yet another non-limiting example, at least a server 104 may record in memory for example at least a biological extraction received from a user. In yet another non-limiting example, at least a server 104 may record in memory a prognostic machine-learning model utilized to generate at least a prognostic output. In yet another non-limiting example, at least a server 104 may record in memory a plurality of ameliorative outputs generated by ameliorative label learner 160.

With continued reference to FIG. 17, at step 1720 at least a server 104 generates at least a descriptor trail 172 wherein the descriptor trail 172 includes at least an element of diagnostic data 176. Descriptor trail 172 includes any data and/or data element describing generation and/or selection of at least a prognostic output and/or ameliorative output including at least a prognostic output and at least a correlated ameliorative output. Descriptor trail 172 may be generated by descriptor generator module 168 as described above in more detail in reference to FIG. 1 and FIG. 12. Diagnostic data 176 contained within descriptor trail 172 may include any of the diagnostic data 176 as described above in reference to FIGS. 1-17. Generating at least a descriptor trail 172 may include receiving at least an advisor filter input containing at least a diagnostic data 176 selection, generating the at least a descriptor trail 172 as a function of the at least an advisor filter and transmitting the at least a descriptor trail 172 to at least an advisor client device. Advisor filter input as used herein includes any input datum received from at least an informed advisor containing a specification for a particular element and/or elements of diagnostic data 176. Advisor filter input includes any input datum received from at least an informed advisor containing a specification for a particular element and/or elements of diagnostic data 176 as described above in more detail in reference to FIG. 1. In an embodiment, advisor filter input may be utilized to select diagnostic data 176 to be transmitted to at least an informed advisor. Advisor filter input may be received from an advisor client device. For example, advisor filter input may include an advisory input to only receive training data utilized to generate a plurality of prognostic outputs or an advisor filter input to receive all diagnostic data 176 utilized to generate at least a prognostic output and/or ameliorative output. In an embodiment, advisor filter input may include a preference to receive confidence levels and statistical analysis utilized to generate a prognostic output and/or ameliorative output. In yet another non-limiting example, advisor filter input may include a request to receive prognostic probability scores or prognostic improvement scores.

Figure 18:
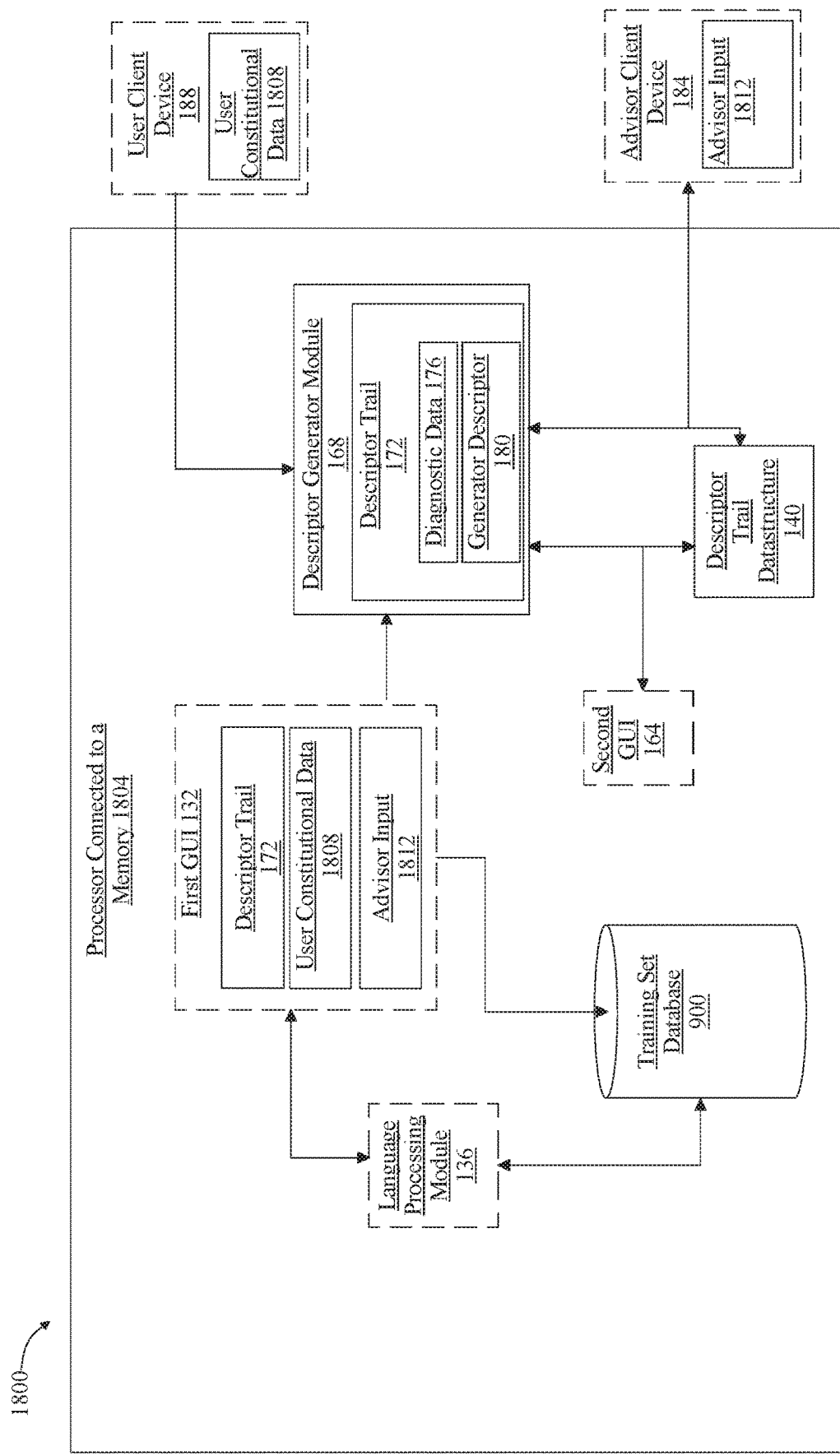
FIG. 18 is a block diagram illustrating an exemplary embodiment of a system for updating a descriptor trail using artificial intelligence.

Referring now to FIG. 18, an exemplary embodiment of a system 1800 for updating a descriptor trail using artificial intelligence is illustrated. System 1800 includes a processor connected to a memory. Processor includes any of the processors as described herein. Memory includes any of the memory as described herein.

With continued reference to FIG. 18, system 1800 includes a graphical user interface. Graphical user interface includes any graphical user interface suitable for use as first graphical user interface 132 as described above in reference to FIGS. 1-17. Graphical user interface 132 is configured to display a descriptor trail wherein the descriptor trail includes an element of diagnostic data pertaining to a user wherein the element of diagnostic data includes a prognostic output and a correlated ameliorative output and an element of machine-learning data. Descriptor trail includes any of the descriptor trails as described above in reference to FIGS. 1-17. Diagnostic data includes any of the diagnostic data as described above in reference to FIGS. 1-17. Prognostic output includes any of the prognostic outputs as described above in reference to FIGS. 1-18. Ameliorative output includes any of the ameliorative outputs as described above in reference to FIGS. 1-18. An "element of machine-learning data" as used in this disclosure, includes any data describing any machine-learning process and/or any data utilized to generate any machine-learning process including prognostic output and/or ameliorative output. Machine learning, includes any algorithm and/or statistical model that processor connected to memory utilizes to perform any task without using explicit instructions, and instead relying on patterns and inferences. Machine learning may include generating machine-learning models utilizing sample data or training data. Machine learning models may include artificial neural networks, decision trees, support vector machines, Bayesian networks, genetic algorithms and the like. Training data may include any of the training data as described above. Machine learning may include supervised learning, unsupervised learning, clustering, dimensionality reduction, structured prediction, anomaly detection, artificial neural networks, reinforcement learning, machine-learning venues, lazy learning, feature learning, sparse dictionary learning, association rules, and the like. Machine-learning may include training models that include federated learning. An element of machine-learning data may include any data element utilized in any machine-learning including any of the above. For instance and without limitation, an element of machine-learning data may include a particular training set selected from training set database 900 and utilized by prognostic label learner 112 to generate prognostic model 116. In yet another non-limiting example, an element of machine-learning data may include a particular lazy-learning algorithm utilized by ameliorative process label learner 144 to generate ameliorative output 1112. An element of machine-learning data may include a particular data entry contained within a training set. An element of machine-learning data is not limited to inputs or outputs generated by a machine-learning model. An element of machine-learning data may include a particular algorithm calculated by a label learner or a particular algorithm calculated by a machine-learning module. An element of machine-learning data may include equations utilized in an unsupervised machine-learning model. An element of machine-learning data may include variables used to minimize a loss function. An element of machine-learning data may include a graphical representation of clusters generated by a clustering algorithm. An element of machine-learning data may include calculations utilized to select a k value in a k-nearest neighbors algorithm. An element of machine-learning data may include classification labels generated by a lazy-learning process.

With continued reference to FIG. 18, an element of machine-learning data may be displayed in any suitable data and/or data type. For instance and without limitation, an element of machine-learning data may be displayed as textual data such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data may take. An element of machine-learning data may be displayed as image data, such as for example an image of particular equations utilized to generate a machine-learning algorithm. Image data may be stored in various forms including for example, joint photographic experts group (JPEG), exchangeable image file format (Exif), tagged image file format (TIFF), graphics interchange format (GIF), portable network graphics (PNG), netpbm format, portable bitmap (PBM), portable any map (PNM), high efficiency image file format (HEIF), still picture interchange file format (SPIFF), better portable graphics (BPG), drawn filed, enhanced compression wavelet (ECW), flexible image transport system (FITS), free lossless image format (FLIF), graphics environment manage (GEM), portable arbitrary map (PAM), personal computer exchange (PCX), progressive graphics file (PGF), gerber formats, 2 dimensional vector formats, 3 dimensional vector formats, compound formats including both pixel and vector data such as encapsulated postscript (EPS), portable document format (PDF), and stereo formats. An element of machine-learning data may be displayed as a graphical representation illustrating what a particular machine-learning model and/or machine-learning algorithm does. An element of machine-learning data may be displayed as a graphical representation illustrating particular selected training sets and/or nodes selected to be incorporated into a particular machine-learning model.

With continued reference to FIG. 18, displaying element of machine-learning data may include displaying a prognostic machine-learning model containing prognostic training data correlating biological extraction data to prognostic data. In an embodiment, a prognostic machine-learning model and prognostic training data may be utilized to generate an element of diagnostic data that may be displayed by a graphical user interface 132. Displaying element of machine-learning data may include displaying an ameliorative machine-learning model containing ameliorative training data correlating prognostic data to ameliorative data. In an embodiment, an ameliorative machine-learning model and ameliorative training data may be utilized to generate an element of diagnostic data that may be displayed by a graphical user interface 132.

With continued reference to FIG. 18, displaying element of machine-learning data may include displaying elements of machine-learning data that were not utilized to generate prognostic output and/or ameliorative output. For instance and without limitation, processor connected to memory may select a first element of machine-learning data, discard a second element of machine-learning data, and display the first element of machine-learning data and the second element of machine-learning data. For instance and without limitation, graphical user interface 132 may display a first selected training set from training set database 900 and display a discarded training set from training set database 900 that was not utilized to a machine-learning model. In yet another non-limiting example, graphical user interface 132 may display a first selected prognostic model utilized to generate a prognostic output and display a discarded second prognostic model that was not utilized to generate the prognostic output. In an embodiment, graphical user interface 132 may display a plurality of discarded training sets and/or models that were not selected to be utilized to generate a prognostic and/or ameliorative output. Graphical user interface 132 may display an element of machine-learning data utilizing any of the methodologies as described above in reference to FIGS. 1-17.

With continued reference to FIG. 18, processor connected to memory is configured to receive from a user client device an element of user constitutional data. User client device includes any of the user client devices as described above in reference to FIG. 1. An "element of user constitutional data" as used in this disclosure, includes any data describing any diagnosis, process, medical condition, ailment, disease, malaise, unwellness, weakness, sickliness, unhealthiness, adherence, and/or infection pertaining to a user's body. An element of constitutional data may include any data describing any current or future probable disease state of a user. An element of constitutional data may include a physically extracted sample analyzed and pertaining to a user including any of the biological extractions as described above in reference to FIGS. 1-17. An element of constitutional data may include findings created by a health professional after performing a physical examination of a user. For instance and without limitation, an element of constitutional data may include findings created by a medical professional such as a functional medicine doctor after performing a physical examination of a user and containing findings that indicate the user is pale in color and complaining of fatigue. In yet another non-limiting example, an element of constitutional data may include a genetic sequence showing a positive test result of the breast cancer gene 1 (BRCA1). In yet another non-limiting example, an element of constitutional data may include a blood result showing a high intracellular level of sodium. In yet another non-limiting example, an element of constitutional data may include a hair sample showing high levels of mercury.

With continued reference to FIG. 18, an element of user constitutional data 1808 may include a user genetic sample containing a genetic sequence linked to a prognosis. A "user genetic sample" as used herein is a sample including any sequence of nucleic acid identified in a user, including without limitation deoxyribonucleic acid (DNA) and/or ribonucleic acid (RNA). DNA may include chromosomal DNA, including without limitation sequences encoding particular genes as well as sequences of DNA disposed between or after gene sequences, including without limitation telomeres. Telomeres, as used in this description are caps (repetitive nucleotide sequences) at the end of linear chromosomes of a user. Telomeres are theorized to play a critical role in facilitating complete chromosome replication. Telomeres are characterized by noncoding tandem arrays of a "TTAGGG" DNA sequence that are located at the terminal ends of all vertebrate chromosomes, including those of humans. A G-rich single stranded 3-prime overhang is present at the end of human telomeres; this overhang, which may be important for telomere function folds back on itself forming a large loop structure called a telomere loop, or T-loop, that has a shape similar to that of a paper clip. A telomere may be stabilized by a six-protein complex, known as "shelterin," which may include telomeric repeat binding factor 1 and 2 (TRF1 and TRF2), protection of telomeres 1 (POT1), TRF1 and TRF2 interacting nuclear protein 2 (TIN2), the human ortholog of the yeast repressor/activator protein 1 (Rap1), and TPP1. Telomere lengths have been observed to reduce over a series of cellular mitotic divisions, such that telomere length and/or changes in telomere length appear to correlate with processes of cellular aging and senescence. It is therefore hypothesized that telomere length and/or changes thereto may be useful to predict life expectancy of a person; however, precise predictions have hitherto eluded researchers. A genetic sample may include mRNA, tRNA, or any other RNA sequence or strand. A user genetic sample may be linked to a prognosis where linked may indicate a known association between a particular genetic sample and a particular prognosis. A known association may include a genetic sample with a known cause for a particular prognosis, a genetic sample with a known contribution to cause a particular prognosis, a genetic sample with a known contributing factor to cause a particular prognosis, and/or a genetic sample with a known associated risk for later developing a particular prognosis. For instance and without limitation, a user genetic sequence such as G/G genotype for the MCM6 gene that controls production of lactase enzyme may be linked to a prognosis of lactose intolerance. In yet another non-limiting example, a user genetic sequence such as G/G genotype for APOA2 gene may be linked to a prognosis for increased risk of weight gain when consuming a diet rich in saturated fats. In yet another non-limiting example, a user genetic sequence such as D/D genotype for ADRA2B gene may be linked to a prognosis of increased risk for overly heightened fear and anxiety responses.

With continued reference to FIG. 18, user constitutional data 1808 may include an element of adherence data linked to an ameliorative output. "Adherence data" as used in this disclosure, includes any data describing the degree to which a user's behavior corresponds with a recommendation from a health care provider contained within an ameliorative output. Adherence data may be linked to an ameliorative output, whereby the adherence data may describe a user's adherence to a particular ameliorative output. Adherence data may indicate a user's compliance with a particular treatment contained within an ameliorative output. For instance and without limitation, adherence data may describe the number of times that a user practiced a particular yoga sequence that was contained within an ameliorative output over a certain period of time. In yet another non-limiting example, adherence data may describe the number of times that a user ingested a supplement over the past week. In yet another non-limiting example, adherence data may describe the number of times that a user missed consuming a dose of user's medication over a one month period. In yet another non-limiting example, adherence data may describe reasons why a user did not practice a particular meditation sequence before bed for two weeks during the previous month.

With continued reference to FIG. 18, processor connected to memory is configured to display on a graphical user interface 132 an element of user constitutional data 1808. This may be performed utilizing any methodology as described herein.

With continued reference to FIG. 18, processor connected to memory is configured to prompt an advisor input 1812. Processor connected to memory may prompt an advisor input 1812 by displaying a field on a graphical user interface 132 containing space for an advisor to enter input. In an embodiment, graphical user interface 132 may display free form textual fields that an advisor may enter text into. In an embodiment, graphical user interface 132 may display a drop down menu which may display multiple options from which an advisor may select an option. Prompt may include displaying the results of any of the above processes plus a field where an advisor can add information. In yet another non-limiting example, a prompt may be located in a separate window.

With continued reference to FIG. 18, processor connected to memory is configured to receive from an advisor client device an advisor input 1812 containing an element of advisory data wherein the advisory data is generated as a function of user constitutional data 1808. An "advisor input 1812" as used in this disclosure, includes a response generated by a user of advisor client device, such as without limitation an informed advisor, in reply to user constitutional data 1808 and/or a descriptor trail. An "informed advisor" as used in this disclosure, includes any medical professional as described above; input from advisor client device may be treated by system 1800 as having been input by an informed advisor, where the advisor client device is recorded in the system as used by and/or belonging to an informed advisor. A response, such as a response generated by an informed advisor, may reflect an informed advisor's thoughts, views, concerns, reflections, analysis, remedy, treatment, and/or alarms in response to an element of user constitutional data 1808. For instance and without limitation, user constitutional data 1808 such as a blood test showing elevated extracellular levels of potassium may cause an informed advisor to generate an advisor input 1812 that contains a new diagnosis of hyperkalemia. In yet another non-limiting example, user constitutional data 1808 that includes a description of an informed advisor's physical examination of a user may cause an informed advisor to generate an advisor input 1812 that includes a finding of a blistering rash on the back of a user's body. In yet another non-limiting example, an advisor input 1812 may include feedback about a particular machine-learning process used to generate diagnostic data about a particular user.

With continued reference to FIG. 18, receiving an advisor input 1812 may include receiving an advisor input 1812 describing feedback about particular prognostic models utilized to generate a prognostic output. Receiving an advisor input 1812 may include displaying on the graphical user interface 132 a plurality of prognostic models and prognostic training sets; receiving from a user client device an element of user constitutional data 1808 containing a user genetic sequence; filtering the plurality of prognostic models and the prognostic training data as a function of the user genetic sequence; selecting a first prognostic model and a first prognostic training set from the plurality of prognostic models and the prognostic training data; displaying on the graphical user interface 132 the selected first prognostic model and the selected first prognostic training set; receiving from an advisor input 1812 an element of advisory data generated as a function of the selected prognostic model and the selected prognostic training set; discarding the first prognostic model and the first prognostic training set as a function of the advisor input 1812; selecting a second prognostic model and a second prognostic training set as a function of the advisor input 1812; and generating an updated descriptor training utilizing the selected second prognostic model and the second prognostic training set.

With continued reference to FIG. 18, receiving an advisor input 1812 may include receiving an advisor input 1812 describing feedback about particular ameliorative models utilized to generate an ameliorative output. Receiving an advisor input 1812 may include displaying on the graphical user interface 132 a plurality of ameliorative outputs; receiving from a user client device an element of user constitutional data 1808 containing an element of adherence data; selecting a first ameliorative output as a function of the element of adherence data; displaying on the graphical user interface 132 the selected first ameliorative output; receiving from an advisor input 1812 an element of advisory data modifying the selected first ameliorative output; generating a second ameliorative output as a function of the element of advisory data modifying the selected first ameliorative output; and displaying the second ameliorative output on the graphical user interface 132.

With continued reference to FIG. 18, processor connected to a memory 1804 is configured to generate an updated descriptor trail as a function of an advisor input 1812. Generating an updated descriptor trail may include receiving an advisor input 1812 containing an element of user physical data. "User physical data" as used in this disclosure, includes any data describing any findings from a physical examination of a user by an informed advisor. Physical examination may include observations about a user that an informed advisor may make such as an examination of a user's eyes, ears, nose, throat, skin color, lesions, nails, hygienic issues and the like. Observations may include the use of certain instruments such as an otoscope that may be used to examine a user's ear canal. Physical examination may include palpitation or touch to certain areas of a user's body to feel for unusual lumps, check organ size, check organ shape, and check a user's response. Physical examination may include percussion such as having an informed advisor place one hand over a user's abdomen and tap it with the other to determine organ location, identify blockages, and pinpoint any problem areas. Physical examination may include acoustic observations such as when an informed advisor may use a stethoscope to listen to a user's heart, lungs, and bowels. Physical examination may include measurement of a user's vital signs including temperature, respiratory rate, pulse, blood pressure, pain levels, menstrual cycle observations, blood glucose, blood oxygen saturation and the like. Physical examination may include a user's report of how a user feels and any changes such as improvements or deterioration to a user's health.

With continued reference to FIG. 18, processor connected to a memory 1804 may select an element of machine-learning data as a function of user physical data. For instance and without limitation, processor connected to a memory 1804 may select a first training set 120 that may be utilized to generate a prognostic output that contains an element of data containing the same element of data contained within user physical data. In yet another non-limiting example, processor connected to a memory 1804 may select an ameliorative model 148 that may be used to treat a particular condition contained within user physical data. Processor connected to a memory 1804 may discard an element of machine-learning data as a function of user physical data. For instance and without limitation, processor connected to a memory 1804 may discard a particular training set that does not contain data entries related to user physical data. In yet another non-limiting example, processor connected to a memory 1804 may discard a particular machine-learning model. Discarded elements of machine-learning data may be recorded in descriptor trail data structure. A particular machine-learning model may be discarded based on an advisor input. For instance and without limitation, an advisor input may indicate that a particular training set does not match user physical data and should be discarded. In yet another non-limiting example, an advisor input may indicate that a particular machine-learning model does not generate ameliorative outputs that are economical for a patient and as such a different machine-learning model needs to be utilized that will generate more price sensitive outputs. Advisor input may be utilized to generate updated prognostic and/or ameliorative outputs. In an embodiment, advisor input may be recorded in descriptor trail.

Processor connected to a memory 1804 is configured to record a selected element of machine-learning data and discarded element of machine-learning data in a descriptor trail data structure. Such entries may then be utilized by processor connected to a memory 1804 to generate an updated descriptor trail. Updated descriptor trail may be displayed on a graphical user interface 132.

With continued reference to FIG. 18, generating an updated descriptor trail may include recording an element of user constitutional data 1808 and an advisor input 1812 in descriptor trail data structure. Processor connected to a memory 1804 may extract at least an element of descriptor data from descriptor trail data structure. An "element of descriptor data" as used in this disclosure, includes any data entry contained within descriptor trail data structure. Data entries contained within descriptor trail data structure may include any element of data describing any step, process, calculation, algorithm, method, and/or data utilized to generate prognostic output and/or ameliorative output. For instance and without limitation, data entries may include a particular prognostic label generated by prognostic label learner 112. In yet another non-limiting example, data entries may include a particular training set discarded by ameliorative process label learner 144 and not utilized to generate ameliorative output. Data entries may include an audit of particular data entries contained within a particular training set utilized to generate an ameliorative output. Data entries may include any entries receive from user client device 188 and/or advisor client device 184 including for example user constitutional data 1808 and/or advisor input 1812. Updated descriptor trail may be generated using the element of descriptor data.

Figure 19:
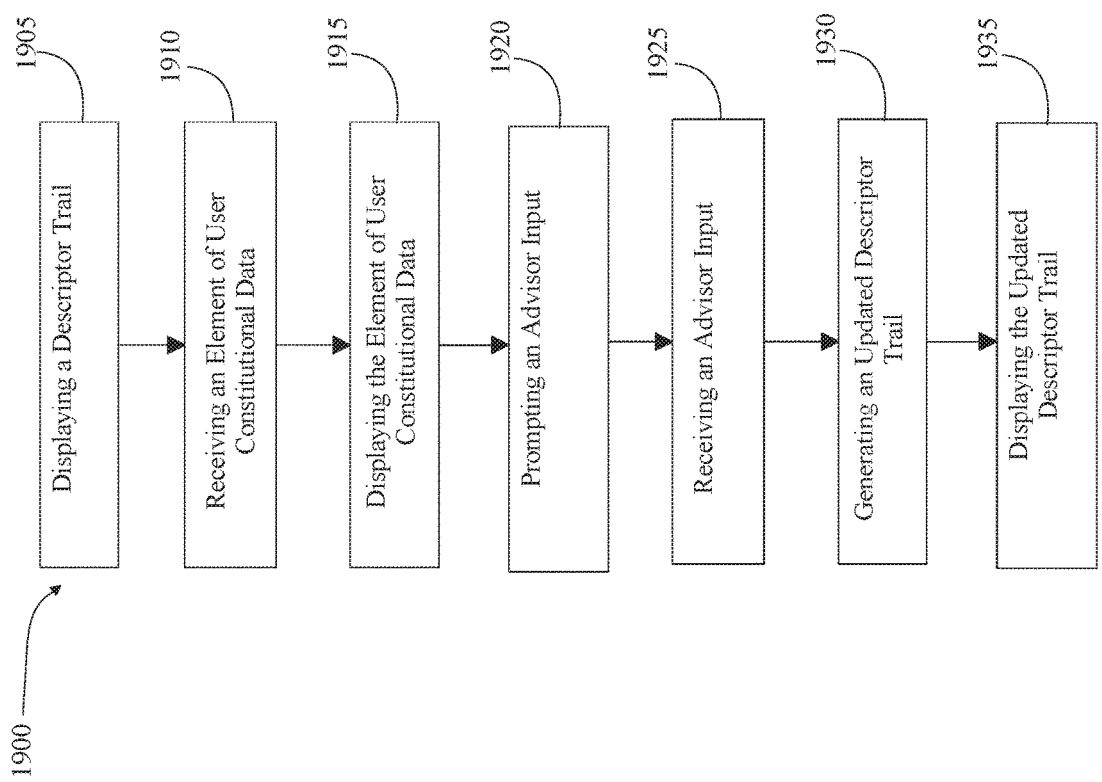
FIG. 19 is a process flow diagram illustrating an exemplary embodiment of a method for updating a descriptor trail using artificial intelligence.

Referring now to FIG. 19, an exemplary embodiment of a method 1900 of updating a descriptor trail using artificial intelligence is illustrated. At step 1905 a processor connected to a memory 1804 displays on a graphical user interface 132 a descriptor trail wherein the descriptor trail includes an element of diagnostic data pertaining to a user including a prognostic output and a correlated ameliorative output and an element of machine-learning data. Processor connected to a memory 1804 may display descriptor trail on a graphical user interface 132 including any of the graphical user interface 132 as described above in reference to FIGS. 1-18. Element of diagnostic data includes any of the diagnostic data as described above in reference to FIGS. 1-18. Prognostic output includes any of the prognostic outputs as described above in reference to FIGS. 1-18. Ameliorative output includes any of the ameliorative outputs as described above in reference to FIGS. 1-18. Element of machine-learning data, includes any data describing any machine-learning process and/or any data utilized to generate any machine-learning process including prognostic output and/or ameliorative output as described above in more detail in reference to FIG. 18.

With continued reference to FIG. 19, displaying an element of machine-learning data may include displaying any machine-learning data utilized to generate a prognostic output and/or ameliorative output. Processor connected to a memory 1804 may display a prognostic machine-learning model containing prognostic training data correlating biological extraction data to prognostic data wherein the prognostic machine-learning model and the prognostic training data are utilized to generate an element of diagnostic data such as prognostic output. Processor connected to a memory 1804 may display a particular prognostic machine-learning model and/or prognostic training data utilized to generate a prognostic output. Processor connected to a memory 1804 may display an ameliorative machine-learning model containing ameliorative training data correlating prognostic data to ameliorative data and the ameliorative machine-learning model and the ameliorative training data are utilized to generate an element of diagnostic data such as ameliorative output.

With continued reference to FIG. 19, processor connected to a memory 1804 may display on a graphical user interface 132 elements of machine-learning data that is not utilized to generate an element of diagnostic data. Processor connected to a memory 1804 may select a first element of machine-learning data, discard a second element of machine-learning data, and display the first element of machine-learning data and the second element of machine-learning data on a graphical user interface 132. For instance and without limitation, processor connected to a memory 1804 may select a first prognostic training set and a second prognostic training set from training set database 900. Processor connected to a memory 1804 may select first prognostic training set to be utilized to generate prognostic output and discard the second prognostic training set. Processor connected to a memory 1804 may display the selected first prognostic training set and the discarded second prognostic training set on a graphical user interface 132. In yet another non-limiting example, processor connected to a memory 1804 may select a first ameliorative machine-learning model such as a supervised machine-learning model and a second ameliorative machine-learning model such as a lazy-learning model. Processor connected to a memory 1804 may select the first supervised ameliorative learning model and discard the second lazy-learning ameliorative model. Processor connected to a memory 1804 may display the first supervised machine-learning model and the second lazy-learning model on a graphical user interface 132.

With continued reference to FIG. 19, at step 1910 a processor connected to a memory 1804 receives from a user client device an element of user constitutional data 1808. User client device may include any of the user client devices as described above in reference to FIGS. 1-18. Element of user constitutional data 1808 describes any diagnosis, process, medical condition, ailment, disease, malaise, unwellness, weakness, sickliness, unhealthiness, adherence, and/or infection pertaining to a user's body. For instance and without limitation, element of user constitutional data 1808 may include a description of a user's subjective feelings about how a user is feeling from a medical point of view. Element of user constitutional data 1808 may include a particular physically extracted sample that was analyzed such as a hair sample analyzed for heavy metal toxicity or a urine sample analyzed for microbial species. Element of user constitutional data 1808 may include a biological extraction including any of the biological extractions as described above in reference to FIGS. 1-18. Element of user constitutional data 1808 may include a description of a particular ailment that a user believes to be suffering from such as a complaint of shortness of breath with exercise. Element of user constitutional data 1808 may include a user genetic sample containing a genetic sequence linked to a prognosis. User genetic sample may include any of the user genetic samples as described above in reference to FIG. 18. For instance and without limitation, element of user constitutional data 1808 may include a user genetic sequence such as the C/T genotype of the methylenetetrahydrofolate reductase (MTHFR) linked to a prognosis of low cellular methylation and increased risk of B vitamin deficiencies. In yet another non-limiting example, element of user constitutional data 1808 may include a user genetic sequence such as A/C genotype of CYP1A2 gene linked to a prognosis of increased risk of caffeine toxicity and high blood pressure and cardiovascular disease. Element of user constitutional data 1808 may include an element of adherence data linked to an ameliorative output. Adherence data may include any of the adherence data as described above in reference to FIG. 18. For instance and without limitation, adherence data may include a description of how a user practiced and/or implemented a particular ameliorative output over a certain period of time. For instance and without limitation, element of user constitutional data 1808 may include a description of how many times a user practiced a particular meditation sequence over a two-week period linked to an ameliorative output that included implementing a nightly meditation sequence before bed. In yet another non-limiting example, element of user constitutional data 1808 may include a description of how many times a user was unable to attend church over the preceding eight weeks linked to an ameliorative output that included developing a religious practice. Processor connected to a memory 1804 receives element of user constitutional data 1808 from a user client device utilizing any network methodology as described herein.

With continued reference to FIG. 19, at step 1915 processor connected to a memory 1804 displays on a graphical user interface 132 an element of user constitutional data 1808. An element of user constitutional data 1808 may be displayed utilizing any methodology as described herein.

With continued reference to FIG. 19, at step 1920 processor connected to a memory 1804 prompts an advisor input 1812 on a graphical user interface 132. Processor connected to a memory 1804 may prompt an advisor input 1812 by displaying a message on graphical user interface 132 for an advisor input 1812. In an embodiment, processor connected to a memory 1804 may display free form text fields that may prompt an advisor input 1812 to type an advisor input 1812 into a free form text field. In an embodiment, processor connected to a memory 1804 may display a drop-down list with auto-generated advisor input 1812 that may prompt an informed advisor to select one or more advisor input 1812 from auto-generated list.

With continued reference to FIG. 19, at step 1925 processor connected to a memory 1804 receives from an advisor client device an advisor input 1812 containing an element of advisory data wherein the advisory data is generated as a function of user constitutional data 1808. Advisor client device may include any of the advisor client devices as described above in reference to FIG. 1. Advisor input 1812, may include an informed advisor's thoughts, views, concerns, reflections, analysis, remedy, treatment, and/or alarms in response to an element of user constitutional data 1808 and/or a descriptor trail as described above in more detail in reference to FIG. 18. For instance and without limitation, advisor input 1812 may include a response generated by an informed advisor in regard to a particular prognostic model selected and utilized to generate a prognostic output. In yet another non-limiting example, advisor input 1812 may include a response generated by an informed advisor in reference to a particular training set utilized to generate an ameliorative output.

With continued reference to FIG. 19, advisor input 1812 may contain an advisor response regarding descriptor trail and particular elements of machine-learning data utilized to generate a descriptor trail. Processor connected to a memory 1804 may display on the graphical user interface 132 a plurality of prognostic models and prognostic training sets. Processor connected to a memory 1804 may receive from a user client device an element of user constitutional data 1808 containing a user genetic sequence. Genetic sequence includes any of the genetic sequences as described above in reference to FIG. 18. Processor connected to memory may filter the plurality of prognostic models and the prognostic training data as a function of the user genetic sequence. Filtering may include matching a user genetic sequence to a prognostic training set containing user genetic sequence. For instance and without limitation, filtering may include matching a user genetic sequence containing A/A genotype for CYP17A1 gene responsible for converting progesterone into androgens to a prognostic training set containing a data entry that includes an A/A genotype for CYP17A1 gene and an associated prognosis. Filtering may include discarding a prognostic training set that does not contain a matched user genetic sequence. For instance and without limitation, filtering may include discarding a prognostic training set that does not contain A/A genotype for CYP17A1 gene and only contains the G/G genotype for CYP17A2 gene. Processor connected to a memory 1804 selects a first prognostic model and a first prognostic training set from the plurality of prognostic models and the prognostic training data. Processor connected to a memory 1804 displays on the graphical user interface 132 the selected first prognostic model and the selected first prognostic training set. Processor connected to a memory 1804 receives from an advisor input 1812 an element of advisory data generated as a function of the selected prognostic model and the selected prognostic training set. Advisor input 1812 may include an informed advisor's thoughts about a particular selected prognostic model and/or prognostic training set. For example, an informed advisor may generate an advisor input 1812 that includes a recommendation for a different prognostic model to be selected. Advisor input may include a point and click selection where an advisor may click on, tap on, or otherwise interact with a displayed machine-learning element and indicate that it should be deleted or altered. In yet another non-limiting example, processor may display other possible machine-learning models or algorithms that may be selected and as such an advisor may select one to be utilized so that another one can be discarded. Processor connected to a memory 1804 may discard the first prognostic model and the first prognostic training set as a function of the advisor input 1812. Processor connected to a memory 1804 may select a second prognostic model and a second prognostic training set as a function of the advisor input 1812. Processor connected to a memory 1804 may generate an updated descriptor training utilizing the selected second prognostic model and the second prognostic training set. Processor connected to a memory 1804 may generate an updated descriptor by recording the selected and/or discarded training sets and/or machine learning models and record them in descriptor trail data structure.

With continued reference to FIG. 19, receiving by processor connected to a memory 1804 an advisor input 1812 includes displaying on a graphical user interface 132 a plurality of ameliorative outputs. Processor connected to a memory 1804 receives from a user client device an element of user constitutional data 1808 containing an element of adherence data. Adherence data may include any of the adherence data as described above in reference to FIG. 18. Processor connected to a memory 1804 selects a first ameliorative output as a function of the element of adherence data. In an embodiment, processor connected to a memory 1804 may generate a category label for an element of adherence data. Processor connected to a memory 1804 may assign a category label such as "complete adherent" to an element of adherence data that includes a report of adhering to all or almost all of an ameliorative output. Processor connected to a memory 1804 may assign a category label such as "mostly adherent" to an element of adherence data that includes a report of adhering to some of an ameliorative output. Processor connected to a memory 1804 may assign a category label such as "not adherent" to an element of adherence data that includes a report of not adhering to most of an ameliorative output. Category label may be utilized by processor connected to a memory 1804 to select a first ameliorative output. For instance and without limitation, processor connected to a memory 1804 may not select a first ameliorative output that requires a great degree of effort and time for an element of user adherence data that has been labeled "not adherent." In yet another non-limiting example, processor connected to a memory 1804 may select a first ameliorative output that does not require a great degree of time or effort for an element of user adherence data that has been labeled "mostly adherent." Processor connected to a memory 1804 displays on the graphical user interface 132 the selected first ameliorative output. Processor connected to a memory 1804 receives from an advisor input 1812 an element of advisory data modifying the selected first ameliorative output. For instance and without limitation, an informed advisor may evaluate an element of user adherence data and a first ameliorative output and generate an advisor input 1812 that includes the informed advisor's opinion about how to best adjust the first ameliorative output based on the informed advisor's knowledge and experience with working with a particular user. For example, an informed advisor may not have personal experiences, observations, thoughts, and knowledge that informed advisor may utilize to generate an advisor input 1812 that reflects the experience of the informed advisor. Processor connected to a memory 1804 generates a second ameliorative output as a function of the element of advisory data modifying the selected first ameliorative output. Generating a second ameliorative output may be done utilizing any of the methods as described above in reference to FIGS. 1-18. Processor connected to a memory 1804 displays the second ameliorative output on the graphical user interface 132.

With continued reference to FIG. 19, at step 1930 processor connected to a memory 1804 generates an updated descriptor trail as a function of advisor input 1812. Generating an updated descriptor trail may include recording any of the processes described in FIG. 19 in descriptor trail data structure. Generating an updated descriptor trail may include receiving an advisor input 1812 containing an element of user physical data. Element of user physical data may include any user physical data as described above in reference to FIG. 18. Element of user physical data may include for example, findings from a physical exam such as a finding of an enlarged and red swollen throat or a discoloration of a patch of skin located on a user's left elbow. Processor connected to a memory 1804 selects an element of machine-learning data as a function of the user physical data. Processor connected to a memory 1804 may select an element of machine-learning data that may match a particular element of user physical data. For instance and without limitation, processor connected to a memory 1804 may select a training set that contains the same element of user physical data. For example, an element of user physical data that includes a red patch on user's nose may be utilized to select a training set that includes a data entry that contains a red patch on user's nose. Processor connected to a memory 1804 discards an element of machine-learning data as a function of the user physical data. For instance and without limitation, processor connected to a memory 1804 may discard an element of machine-learning data such as a machine-learning model that does not include user physical data. Processor connected to a memory 1804 records the selected element of machine-learning data and the discarded element of machine-learning data in a descriptor trail data structure. This may be performed utilizing any of the methods as described above in reference to FIGS. 1-18. Processor connected to a memory 1804 generates an updated descriptor trail. Generating an updated descriptor trail may include recording an element of user constitutional data 1808 and an advisor input 1812 in a descriptor trail data structure. This may be performed utilizing any method as described above in reference to FIGS. 1-19. Processor connected to a memory 1804 extracts at least an element of descriptor data from descriptor trail data structure. Descriptor data may include any of the descriptor data as described above in reference to FIGS. 1-18. Processor connected to a memory 1804 generates an updated descriptor trail using element of descriptor data.

With continued reference to FIG. 19, at step 1935 a processor connected to a memory 1804 displays an updated descriptor trail on a graphical user interface 132. This may be performed utilizing any of the methods as described above in reference to FIGS. 1-19.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 20:
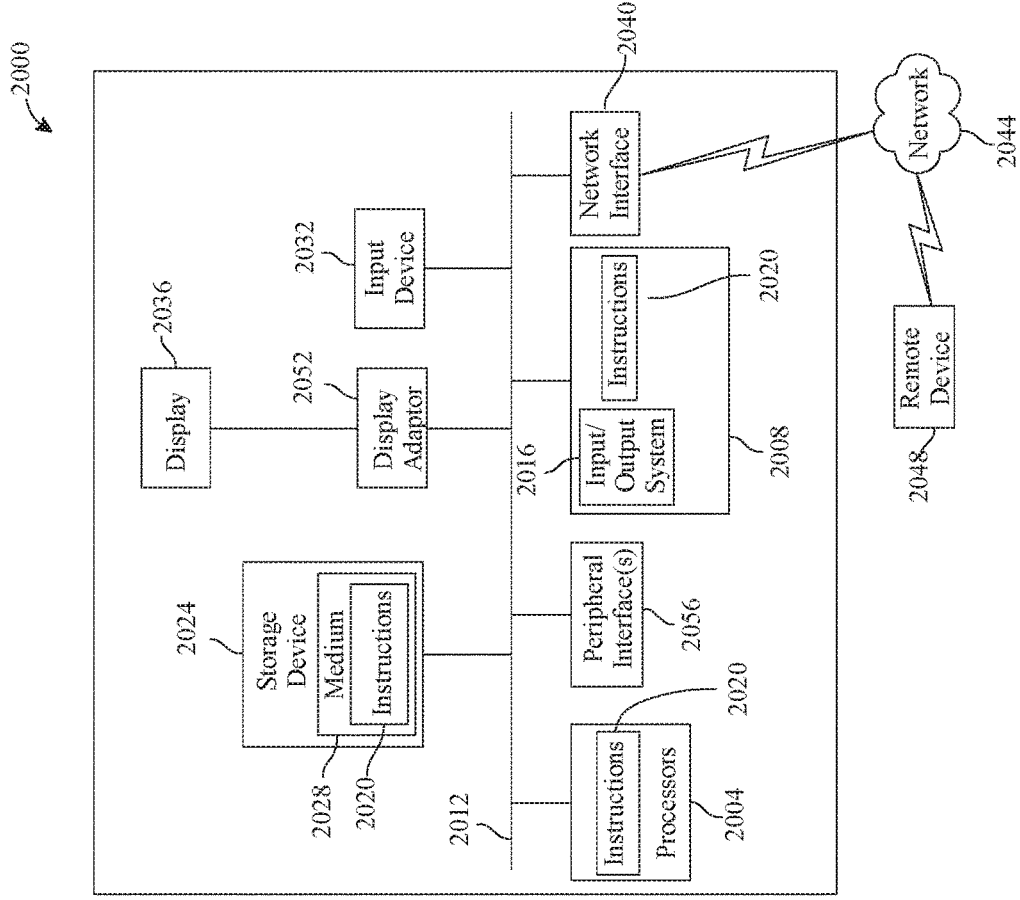
FIG. 20 is a block diagram of a computing system that can be used to implement any one or more of the methodologies disclosed herein and any one or more portions thereof.

FIG. 20 shows a diagrammatic representation of one embodiment of a computing device in the exemplary form of a computer system 2000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 2000 includes a processor 2004 and a memory 2008 that communicate with each other, and with other components, via a bus 2012. Bus 2012 may include any of several types of bus structures including, but not limited to, a memory bus, a memory controller, a peripheral bus, a local bus, and any combinations thereof, using any of a variety of bus architectures.

Memory 2008 may include various components (e.g., machine-readable media) including, but not limited to, a random access memory component, a read only component, and any combinations thereof. In one example, a basic input/output system 2016 (BIOS), including basic routines that help to transfer information between elements within computer system 2000, such as during start-up, may be stored in memory 2008. Memory 2008 may also include (e.g., stored on one or more machine-readable media) instructions (e.g., software) 2020 embodying any one or more of the aspects and/or methodologies of the present disclosure. In another example, memory 2008 may further include any number of program modules including, but not limited to, an operating system, one or more application programs, other program modules, program data, and any combinations thereof.

Computer system 2000 may also include a storage device 2024. Examples of a storage device (e.g., storage device 2024) include, but are not limited to, a hard disk drive, a magnetic disk drive, an optical disc drive in combination with an optical medium, a solid-state memory device, and any combinations thereof. Storage device 2024 may be connected to bus 2012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 2024 (or one or more components thereof) may be removably interfaced with computer system 2000 (e.g., via an external port connector (not shown)). Particularly, storage device 2024 and an associated machine-readable medium 2028 may provide nonvolatile and/or volatile storage of machine-readable instructions, data structures, program modules, and/or other data for computer system 2000. In one example, software 2020 may reside, completely or partially, within machine-readable medium 2028. In another example, software 2020 may reside, completely or partially, within processor 2004.

Computer system 2000 may also include an input device 2032. In one example, a user of computer system 2000 may enter commands and/or other information into computer system 2000 via input device 2032. Examples of an input device 2032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 2032 may be interfaced to bus 2012 via any of a variety of interfaces (not shown) including, but not limited to, a serial interface, a parallel interface, a game port, a USB interface, a FIREWIRE interface, a direct interface to bus 2012, and any combinations thereof. Input device 2032 may include a touch screen interface that may be a part of or separate from display 2036, discussed further below. Input device 2032 may be utilized as a user selection device for selecting one or more graphical representations in a graphical interface as described above.

A user may also input commands and/or other information to computer system 2000 via storage device 2024 (e.g., a removable disk drive, a flash drive, etc.) and/or network interface device 2040. A network interface device, such as network interface device 2040, may be utilized for connecting computer system 2000 to one or more of a variety of networks, such as network 2044, and one or more remote devices 2048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 2044, may employ a wired and/or a wireless mode of communication. In general, any network topology may be used. Information (e.g., data, software 2020, etc.) may be communicated to and/or from computer system 2000 via network interface device 2040.

Computer system 2000 may further include a video display adapter 2052 for communicating a displayable image to a display device, such as display device 2036. Examples of a display device include, but are not limited to, a liquid crystal display (LCD), a cathode ray tube (CRT), a plasma display, a light emitting diode (LED) display, and any combinations thereof. Display adapter 2052 and display device 2036 may be utilized in combination with processor 2004 to provide graphical representations of aspects of the present disclosure. In addition to a display device, computer system 2000 may include one or more other peripheral output devices including, but not limited to, an audio speaker, a printer, and any combinations thereof. Such peripheral output devices may be connected to bus 2012 via a peripheral interface 2056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for updating a descriptor trail using artificial intelligence the system comprising a processor connected to a memory, wherein the processor is designed and configured to:
    display on a graphical user interface a descriptor trail wherein the descriptor trail includes an element of diagnostic data pertaining to a user including a prognostic output and a correlated ameliorative output and an element of machine-learning data,
        wherein displaying the element of machine-learning data further comprises:
        selecting a first element of machine-learning data;
        discarding a second element of machine-learning data; and
        displaying the first element of machine-learning data and the discarded second element of machine-learning data on the graphical user interface;
    receive from a user client device an element of user constitutional data;
    display on the graphical user interface the element of user constitutional data;
    prompt an advisor input on the graphical user interface;
    receive from an advisor client device an advisor input containing an element of advisory data wherein the advisory data is generated as a function of the user constitutional data; and
    display the updated descriptor trail on the graphical user interface.

2. The system of claim 1, wherein displaying the element of machine-learning data further comprises displaying a prognostic machine-learning model containing prognostic training data correlating biological extraction data to prognostic data wherein the prognostic machine-learning model and the prognostic training data are utilized to generate the element of diagnostic data.

3. The system of claim 1, wherein displaying the element of machine-learning data further comprises displaying an ameliorative machine-learning model containing ameliorative training data correlating prognostic data to ameliorative data and the ameliorative machine-learning model and the ameliorative training data are utilized to generate the element of diagnostic data.

4. The system of claim 1, wherein receiving the element of user constitutional data further comprises receiving a user genetic sample wherein the user genetic sample further comprises a genetic sequence linked to a prognosis.

5. The system of claim 1, wherein receiving the element of user constitutional data further comprises receiving an element of adherence data linked to an ameliorative output.

6. The system of claim 1, wherein receiving an advisor input further comprises:
    displaying on the graphical user interface a plurality of prognostic models and prognostic training sets;
    receiving from a user client device an element of user constitutional data containing a user genetic sequence;
    filtering the plurality of prognostic models and the prognostic training data as a function of the user genetic sequence;
    selecting a first prognostic model and a first prognostic training set from the plurality of prognostic models and the prognostic training data;
    displaying on the graphical user interface the selected first prognostic model and the selected first prognostic training set;
    receiving from an advisor client device an advisor input containing an element of advisory data generated as a function of the selected first prognostic model and the selected first prognostic training set;
    discarding the first prognostic model and the first prognostic training set as a function of the advisor input;
    selecting a second prognostic model and a second prognostic training set as a function of the advisor input; and
    generating an updated descriptor training utilizing the selected second prognostic model and the second prognostic training set.

7. The system of claim 1, wherein receiving an advisor input further comprises:
    displaying on the graphical user interface a plurality of ameliorative outputs;
    receiving from a user client device an element of user constitutional data containing an element of adherence data;
    selecting a first ameliorative output as a function of the element of adherence data;
    displaying on the graphical user interface the selected first ameliorative output;
    receiving from an advisor input an element of advisory data modifying the selected first ameliorative output;
    generating a second ameliorative output as a function of the element of advisory data modifying the selected first ameliorative output; and
    displaying the second ameliorative output on the graphical user interface.

8. The system of claim 1, wherein generating an updated descriptor trail further comprises:
    selecting an element of machine-learning data as a function of the user physical data;
    discarding an element of machine-learning data as a function of the user physical data;
    recording the selected element of machine-learning data and the discarded element of machine-learning data in a descriptor trail data structure; and
    generating an updated descriptor trail.

9. The system of claim 1, wherein generating an updated descriptor trail further comprises:
    recording the element of user constitutional data and the advisor input in a descriptor trail data structure;
    extracting at least an element of descriptor data from the descriptor trail data structure; and
    generating the updated descriptor trail using the at least an element of descriptor data.

10. A method of updating a descriptor trail using artificial intelligence the method comprising:
    displaying by a processor connected to a memory on a graphical user interface a descriptor trail wherein the descriptor trail includes an element of diagnostic data pertaining to a user including a prognostic output and a correlated ameliorative output and an element of machine-learning data, wherein displaying the element of machine-learning data further comprises:
        selecting a first element of machine-learning data;
        discarding a second element of machine-learning data; and
        displaying the first element of machine-learning data and the discarded second element of machine-learning data on the graphical user interface;
    receiving by the processor from a user client device an element of user constitutional data;
    displaying by the processor on the graphical user interface the element of user constitutional data;
    prompting by the processor an advisor input on the graphical user interface;

receiving by the processor from an advisor client device an advisor input containing an element of advisory data wherein the advisory data is generated as a function of the user constitutional data; and displaying by the processor the updated descriptor trail on the graphical user interface.

11. The method of claim 10, wherein displaying the element of machine-learning data further comprises displaying a prognostic machine-learning model containing prognostic training data correlating biological extraction data to prognostic data wherein the prognostic machine-learning model and the prognostic training data are utilized to generate the element of diagnostic data.

12. The method of claim 10, wherein displaying the element of machine-learning data further comprises displaying an ameliorative machine-learning model containing ameliorative training data correlating prognostic data to ameliorative data and the ameliorative machine-learning model and the ameliorative training data are utilized to generate the element of diagnostic data.

13. The method of claim 10, wherein receiving the element of user constitutional data further comprises receiving a user genetic sample wherein the user genetic sample further comprises a genetic sequence linked to a prognosis.

14. The method of claim 10, wherein receiving the element of user constitutional data further comprises receiving an element of adherence data linked to an ameliorative output.

15. The method of claim 10, wherein receiving an advisor input further comprises:
displaying on the graphical user interface a plurality of prognostic models and prognostic training sets;
receiving from a user client device an element of user constitutional data containing a user genetic sequence;
filtering the plurality of prognostic models and the prognostic training data as a function of the user genetic sequence;
selecting a first prognostic model and a first prognostic training set from the plurality of prognostic models and the prognostic training data;
displaying on the graphical user interface the selected first prognostic model and the selected first prognostic training set;
receiving from an advisor input an element of advisory data generated as a function of the selected prognostic model and the selected prognostic training set;
discarding the first prognostic model and the first prognostic training set as a function of the advisor input;
selecting a second prognostic model and a second prognostic training set as a function of the advisor input; and
generating an updated descriptor training utilizing the selected second prognostic model and the second prognostic training set.

16. The method of claim 10, wherein receiving an advisor input further comprises:
displaying on the graphical user interface a plurality of ameliorative outputs;
receiving from a user client device an element of user constitutional data containing an element of adherence data;
selecting a first ameliorative output as a function of the element of adherence data;
displaying on the graphical user interface the selected first ameliorative output;
receiving from an advisor input an element of advisory data modifying the selected first ameliorative output;
generating a second ameliorative output as a function of the element of advisory data modifying the selected first ameliorative output; and
displaying the second ameliorative output on the graphical user interface.

17. The method of claim 10, wherein generating an updated descriptor trail further comprises:
receiving an advisor input containing an element of user physical data;
selecting an element of machine-learning data as a function of the user physical data;
discarding an element of machine-learning data as a function of the user physical data;
recording the selected element of machine-learning data and the discarded element of machine-learning data in a descriptor trail data structure; and
generating an updated descriptor trail.

18. The method of claim 10, wherein generating an updated descriptor trail further comprises:
recording the element of user constitutional data and the advisor input in a descriptor trail data structure;
extracting at least an element of descriptor data from the descriptor trail data structure; and
generating the updated descriptor trail using the element of descriptor data.

\* \* \* \* \*